(12) United States Patent
Adang et al.

(10) Patent No.: US 7,345,229 B1
(45) Date of Patent: *Mar. 18, 2008

(54) INSECT RESISTANT COTTON PLANTS

(75) Inventors: Michael J. Adang, Athens, GA (US); John D. Kemp, Las Cruces, NM (US); Ebrahim Firoozabady, Pleasant Hill, CA (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/478,153

(22) Filed: Jun. 7, 1995

Related U.S. Application Data

(60) Continuation of application No. 08/151,615, filed on Nov. 12, 1993, now abandoned, which is a division of application No. 07/713,624, filed on Jun. 10, 1991, now Pat. No. 6,943,282, which is a continuation of application No. 07/260,574, filed on Oct. 21, 1988, now abandoned, which is a continuation-in-part of application No. 06/848,733, filed on Apr. 4, 1986, now abandoned, which is a continuation-in-part of application No. 06/535,354, filed on Sep. 26, 1983, now abandoned.

(51) Int. Cl.
C12N 15/82 (2006.01)
A01H 5/00 (2006.01)
C12N 15/32 (2006.01)

(52) U.S. Cl. .................. 800/314; 800/288; 800/302; 536/23.71

(58) Field of Classification Search ............... None
See application file for complete search history.

(56) References Cited

OTHER PUBLICATIONS

Dandekar et al. Plant Science 96(1-2): 151-162 (1994).*
Pang et al. Gene 116: 165-172 (1992).*
Bevan, M.W. et al. (1983) "A chimaeric antibiotic resistance gene as a selectable marker for plant cell transformation" Nature 304:184-187.
Fraley, R.T. et al. (1983) "Expression of bacterial genes in plant cells" Proc. Natl. Acad. Sci. USA 80:4803-4807.
Held, G.A. et al. (1982) "Cloning and localization of the lepidopteran protoxin gene of *Bacillus thuringiensis* subsp. *kurstaki*" Proc. Natl. Acad. Sci. USA 79:6065-6069.

Herrera-Estrella et al. (1983) "Expression of chimaeric genes transferred into plant cells using a Ti-plasmid-derived vector" Nature 303:209-213.
Klier, A. et al. (1982) "Cloning and expression of the crystal protein genes from *Bacillus thuringiensis* strain *berliner* 1715" EMBO J. 1:791-799.
Schnepf, H.E., H.R. Whiteley (1981) "Cloning and expression of the *Bacillus thuringiensis* crystal protein gene in *Escherichia coli*" Proc. Natl. Acad. Sci. USA 78:2893-2897.
Whiteley, H.R. et al. (1982) "Cloning the Crystal Protein Gene of *B. thuringiensis* in *E. coli*" in Molecular Cloning and Gene Regulation in Bacilli, pp. 131-144.
Barton, K.A. et al. (1983) "Regeneration of Intact Tobacco Plants Containing Full Length Copies of Genetically Engineered T-DNA, and Transmission of T-DNA to R1 Progeny" Cell 32:1033-1043.
Barton, K.A., W.J. Brill (1983) "Prospects in Plant Genetic Engineering" Science 219:671-676.
Umbeck Motion 2, Filed in Patent Interference No. 105,367 on Jan. 11, 2006.
Adang, M.J., Kemp, J.D., and Firoozabady, E., v. Umbeck, P.F., Before the Board of Patent Appeals and Interferences, United States Patent and Trademark Office, Patent Interference No. 105,367, Paper No. 86, Sep. 18, 2006, pp. 1-42.
Adang, M.J., Kemp, J.D., and Firoozabady, E., v. Umbeck, P.F., "Opening Brief of Appellants Michael J. Adang, John D. Kemp, and Ebrahim Firoozabady", Appeal from the United States Patent and Trademark Office, Board of Patent Appeals and Interferences, Patent Interference No. 105,367, Mar. 5, 2007, pp. i-iv, 1-54, and A1-A2011.
Adang, Michael J., Kemp, John D., and Firoozabady, Ebrahim v. Umbeck, Paul F., United States Court of Appeals for the Federal Circuit, "Judgment", On Appeal from the United States Patent and Trademark Office, Board of Patent Appeals and Interferences, Patent Interference No. 105,367, Oct. 25, 2007.

* cited by examiner

*Primary Examiner*—David T Fox
(74) *Attorney, Agent, or Firm*—Saliwanchik, Lloyd & Saliwanchik

(57) ABSTRACT

A method for expressing insecticidal protein structural genes in cotton plant genomes is provided. In the preferred embodiments this invention comprises placing a structural gene for the *Bacillus thuringiensis* crystal protein under control of a plant or a T-DNA promoter and ahead of a polyadenylation site followed by insertion of said promoter/structural gene combination into a plant genome by utilizing an *Agrobacterium tumefaciens* Ti plasmid-based transformation system. The modified Ti plasmid is then used to transform recipient plant cells. Also provided are the plants and tissues produced by this method and bacterial strains, plasmids, and vectors useful for execution of this invention.

2 Claims, 8 Drawing Sheets

```
aagtggattt tatatataag tataaaaagt aataagactt taaaataagt taacggaata    60 caaacccttta atgcattggt taaacattgt aaagtctaaa gcatggataa tgggcgagaa   120
gtaagtagat tgttaacacc ctgggtcaaa aattgatatt tagtaaaatt agttgcactt   180
tgtgcatttt ttgataagat gagtcatatg ttttaaattg tagtaatgaa aacagtatt    240 atatcataat gaattggtat cttaataaaa gagatggagg taactt atg gat aac      295
                                                  Met Asp Asn
                                                   1
```

| | | | | | | | | | | | | | | |
|---|---|---|---|---|---|---|---|---|---|---|---|---|---|---|
| aat | ccg | aac | atc | aat | gaa | tgc | att | cct | tat | aat | tgt | tta | agt | aac | cct | 343 |
| Asn | Pro | Asn | Ile | Asn | Glu | Cys | Ile | Pro | Tyr | Asn | Cys | Leu | Ser | Asn | Pro |
| | | 5 | | | | 10 | | | | | 15 | | | | |

| gaa | gta | gaa | gta | tta | ggt | gga | gaa | aga | ata | gaa | act | ggt | tac | acc | cca | 391 |
| Glu | Val | Glu | Val | Leu | Gly | Gly | Glu | Arg | Ile | Glu | Thr | Gly | Tyr | Thr | Pro |
| 20 | | | | | 25 | | | | | 30 | | | | | 35 |

| atc | gat | att | tcc | ttg | tcg | cta | acg | caa | ttt | ctt | ttg | agt | gaa | ttt | gtt | 439 |
| Ile | Asp | Ile | Ser | Leu | Ser | Leu | Thr | Gln | Phe | Leu | Leu | Ser | Glu | Phe | Val |
| | | | | 40 | | | | | 45 | | | | | 50 | |

| ccc | ggt | gct | gga | ttt | gtg | tta | gga | cta | gtt | gat | ata | ata | tgg | gga | att | 487 |
| Pro | Gly | Ala | Gly | Phe | Val | Leu | Gly | Leu | Val | Asp | Ile | Ile | Trp | Gly | Ile |
| | | | 55 | | | | | 60 | | | | | 65 | | |

| ttt | ggt | ccc | tct | caa | tgg | gac | gca | ttt | ctt | gta | caa | att | gaa | cag | tta | 535 |
| Phe | Gly | Pro | Ser | Gln | Trp | Asp | Ala | Phe | Leu | Val | Gln | Ile | Glu | Gln | Leu |
| | | | 70 | | | | | 75 | | | | | 80 | | |

| att | aac | caa | aga | ata | gaa | gaa | ttc | gct | agg | aac | caa | gcc | att | tct | aga | 583 |
| Ile | Asn | Gln | Arg | Ile | Glu | Glu | Phe | Ala | Arg | Asn | Gln | Ala | Ile | Ser | Arg |
| | | | 85 | | | | | 90 | | | | | 95 | | |

| tta | gaa | gga | cta | agc | aat | ctt | tat | caa | att | tac | gca | gaa | tct | ttt | aga | 631 |
| Leu | Glu | Gly | Leu | Ser | Asn | Leu | Tyr | Gln | Ile | Tyr | Ala | Glu | Ser | Phe | Arg |
| 100 | | | | | 105 | | | | | 110 | | | | | 115 |

| gag | tgg | gaa | gca | gat | cct | act | aat | cca | gca | tta | aga | gaa | gag | atg | cgt | 679 |
| Glu | Trp | Glu | Ala | Asp | Pro | Thr | Asn | Pro | Ala | Leu | Arg | Glu | Glu | Met | Arg |
| | | | | 120 | | | | | 125 | | | | | 130 | |

| att | caa | ttc | aat | gac | atg | aac | agt | gcc | ctt | aca | acc | gct | att | cct | ctt | 727 |
| Ile | Gln | Phe | Asn | Asp | Met | Asn | Ser | Ala | Leu | Thr | Thr | Ala | Ile | Pro | Leu |
| | | | | 135 | | | | | 140 | | | | | 145 | |

| ttt | gca | gtt | caa | aat | tat | caa | gtt | cct | ctt | tta | tca | gta | tat | gtt | caa | 775 |
| Phe | Ala | Val | Gln | Asn | Tyr | Gln | Val | Pro | Leu | Leu | Ser | Val | Tyr | Val | Gln |
| | | | | 150 | | | | | 155 | | | | | 160 | |

FIGURE 1-1

```
gct gca aat tta cat tta tca gtt ttg aga gat gtt tca gtg ttt gga        823
Ala Ala Asn Leu His Leu Ser Val Leu Arg Asp Val Ser Val Phe Gly
    165             170             175 caa agg tgg gga ttt gat gcc gcg act agc aat agt cgt tat aat gat        871
Gln Arg Trp Gly Phe Asp Ala Ala Thr Ser Asn Ser Arg Tyr Asn Asp
180             185             190             195 tta act agg ctt att ggc aac tat aca gat tat gct gta cgc tgg tac        919
Leu Thr Arg Leu Ile Gly Asn Tyr Thr Asp Tyr Ala Val Arg Trp Tyr
                200             205             210 aat acg gga tta gaa cgt gta tgg gga ccg gat tct aga gat tgg gta        967
Asn Thr Gly Leu Glu Arg Val Trp Gly Pro Asp Ser Arg Asp Trp Val
        215             220             225 agg tat aat caa ttt aga aga gaa tta aca cta act gta tta gat atc       1015
Arg Tyr Asn Gln Phe Arg Arg Glu Leu Thr Leu Thr Val Leu Asp Ile
        230             235             240 gtt gct ctg ttc ccg aat tat gat agt aga aga tat cca att cga aca       1063
Val Ala Leu Phe Pro Asn Tyr Asp Ser Arg Arg Tyr Pro Ile Arg Thr
        245             250             255 gtt tcc caa tta aca aga gaa att tat aca aac cca gta tta gaa aat       1111
Val Ser Gln Leu Thr Arg Glu Ile Tyr Thr Asn Pro Val Leu Glu Asn
260             265             270             275 ttt gat ggt agt ttt cga ggc tcg gct cag ggc ata gaa aga agt att       1159
Phe Asp Gly Ser Phe Arg Gly Ser Ala Gln Gly Ile Glu Arg Ser Ile
                280             285             290 agg agt tca cat ttg atg gat ata ctt aac agt ata acc atc tat acg       1207
Arg Ser Ser His Leu Met Asp Ile Leu Asn Ser Ile Thr Ile Tyr Thr
        295             300             305 gat gct cat agg ggt tat tat tat tgg tca ggg cat caa ata atg gct       1255
Asp Ala His Arg Gly Tyr Tyr Tyr Trp Ser Gly His Gln Ile Met Ala
        310             315             320 tct cct gta ggg ttt tcg ggg cca gaa ttc act ttt ccg cta tat gga       1303
Ser Pro Val Gly Phe Ser Gly Pro Glu Phe Thr Phe Pro Leu Tyr Gly
        325             330             335 act atg gga aat gca gct cca caa caa cgt att gtt gct caa cta ggt       1351
Thr Met Gly Asn Ala Ala Pro Gln Gln Arg Ile Val Ala Gln Leu Gly
340             345             350             355 cag ggc gtg tat aga aca tta tcg tcc act tta tat aga aga cct ttt       1399
Gln Gly Val Tyr Arg Thr Leu Ser Ser Thr Leu Tyr Arg Arg Pro Phe
                360             365             370
```

FIGURE 1-2

```
aat ata ggg ata aat aat caa caa cta tct gtt ctt gac ggg aca gaa    1447
Asn Ile Gly Ile Asn Asn Gln Gln Leu Ser Val Leu Asp Gly Thr Glu
            375                 380                 385 ttt gct tat gga acc tcc tca aat ttg cca tcc gct gta tac aga aaa    1495
Phe Ala Tyr Gly Thr Ser Ser Asn Leu Pro Ser Ala Val Tyr Arg Lys
        390                 395                 400 agc gga acg gta gat tcg ctg gat gaa ata ccg cca cag aat aac aac    1543
Ser Gly Thr Val Asp Ser Leu Asp Glu Ile Pro Pro Gln Asn Asn Asn
    405                 410                 415 gtg cca cct agg caa gga ttt agt cat cga tta agc cat gtt tca atg    1591
Val Pro Pro Arg Gln Gly Phe Ser His Arg Leu Ser His Val Ser Met
420                 425                 430                 435 ttt cgt tca ggc ttt agt aat agt agt gta agt ata ata aga gct cct    1639
Phe Arg Ser Gly Phe Ser Asn Ser Ser Val Ser Ile Ile Arg Ala Pro
                440                 445                 450 atg ttc tct tgg ata cat cgt agt gct gaa ttt aat aat ata att gca    1687
Met Phe Ser Trp Ile His Arg Ser Ala Glu Phe Asn Asn Ile Ile Ala
            455                 460                 465 tcg gat agt att act caa atc cct gca gtg aag gga aac ttt ctt ttt    1735
Ser Asp Ser Ile Thr Gln Ile Pro Ala Val Lys Gly Asn Phe Leu Phe
        470                 475                 480 aat ggt tct gta att tca gga cca gga ttt act ggt ggg gac tta gtt    1783
Asn Gly Ser Val Ile Ser Gly Pro Gly Phe Thr Gly Gly Asp Leu Val
    485                 490                 495 aga tta aat agt agt gga aat aac att cag aat aga ggg tat att gaa    1831
Arg Leu Asn Ser Ser Gly Asn Asn Ile Gln Asn Arg Gly Tyr Ile Glu
500                 505                 510                 515 gtt cca att cac ttc cca tcg aca tct acc aga tat cga gtt cgt gta    1879
Val Pro Ile His Phe Pro Ser Thr Ser Thr Arg Tyr Arg Val Arg Val
                520                 525                 530 cgg tat gct tct gta acc ccg att cac ctc aac gtt aat tgg ggt aat    1927
Arg Tyr Ala Ser Val Thr Pro Ile His Leu Asn Val Asn Trp Gly Asn
            535                 540                 545 tca tcc att ttt tcc aat aca gta cca gct aca gct acg tca tta gat    1975
Ser Ser Ile Phe Ser Asn Thr Val Pro Ala Thr Ala Thr Ser Leu Asp
        550                 555                 560 aat cta caa tca agt gat ttt ggt tat ttt gaa agt gcc aat gct ttt    2023
Asn Leu Gln Ser Ser Asp Phe Gly Tyr Phe Glu Ser Ala Asn Ala Phe
    565                 570                 575
```

FIGURE 1-3

```
aca tct tca tta ggt aat ata gta ggt gtt aga aat ttt agt ggg act    2071
Thr Ser Ser Leu Gly Asn Ile Val Gly Val Arg Asn Phe Ser Gly Thr
580             585             590             595 gca gga gtg ata ata gac aga ttt gaa ttt att cca gtt act gca aca    2119
Ala Gly Val Ile Ile Asp Arg Phe Glu Phe Ile Pro Val Thr Ala Thr
            600             605             610 ctc gag gct gaa tat aat ctg gaa aga gcg cag aag gcg gtg aat gcg    2167
Leu Glu Ala Glu Tyr Asn Leu Glu Arg Ala Gln Lys Ala Val Asn Ala
        615             620             625 ctg ttt acg tct aca aac caa cta ggg cta aaa aca aat gta acg gat    2215
Leu Phe Thr Ser Thr Asn Gln Leu Gly Leu Lys Thr Asn Val Thr Asp
    630             635             640 tat cat att gat caa gtg tcc aat tta gtt acg tat tta tcg gat gaa    2263
Tyr His Ile Asp Gln Val Ser Asn Leu Val Thr Tyr Leu Ser Asp Glu
645             650             655 ttt tgt ctg gat gaa aag cga gaa ttg tcc gag aaa gtc aaa cat gcg    2311
Phe Cys Leu Asp Glu Lys Arg Glu Leu Ser Glu Lys Val Lys His Ala
660             665             670             675 aag gca ctc agt gat gaa cgc aat tta ctc caa gat tca aat ttc aaa    2359
Lys Ala Leu Ser Asp Glu Arg Asn Leu Leu Gln Asp Ser Asn Phe Lys
            680             685             690 gac att aat agg caa cca gaa cgt ggg tgg gcc gga agt aca ggg att    2407
Asp Ile Asn Arg Gln Pro Glu Arg Gly Trp Gly Gly Ser Thr Gly Ile
        695             700             705 acc atc caa gga ggg gat gac gta ttt aaa gaa aat tac gtc aca cta    2455
Thr Ile Gln Gly Gly Asp Asp Val Phe Lys Glu Asn Tyr Val Thr Leu
    710             715             720 tca ggt acc ttt gat gag tgc tat cca aca tat ttg tat caa aaa atc    2503
Ser Gly Thr Phe Asp Glu Cys Tyr Pro Thr Tyr Leu Tyr Gln Lys Ile
725             730             735 gat gaa tca aaa tta aaa gcc ttt acc cgt tat caa tta aga ggg tat    2551
Asp Glu Ser Lys Leu Lys Ala Phe Thr Arg Tyr Gln Leu Arg Gly Tyr
740             745             750             755 atc gaa gat agt caa gac tta gaa atc tat tta att cgc tac aat gca    2599
Ile Glu Asp Ser Gln Asp Leu Glu Ile Tyr Leu Ile Arg Tyr Asn Ala
            760             765             770 aaa cat gaa aca gta aat gtg cca ggt acg ggt tcc tta tgg ccg ctt    2647
Lys His Glu Thr Val Asn Val Pro Gly Thr Gly Ser Leu Trp Pro Leu
        775             780             785
```

FIGURE 1-4

```
tca gcc caa agt cca atc gga aag tgt gga cag ccg aat cga tgc gcg    2695
Ser Ala Gln Ser Pro Ile Gly Lys Cys Gly Glu Pro Asn Arg Cys Ala
        790             795             800 cca cac ctt gaa tgg aat cct gac tta gat tgt tcg tgt agg gat gga    2743
Pro His Leu Glu Trp Asn Pro Asp Leu Asp Cys Ser Cys Arg Asp Gly
    805             810             815 gaa aag tgt gcc cat cat tcg cat cat ttc tcc tta gac att gat gta    2791
Glu Lys Cys Ala His His Ser His His Phe Ser Leu Asp Ile Asp Val
820             825             830             835 gga tgt aca gac tta aat gag gac cta ggt gta tgg gtg atc ttt aag    2839
Gly Cys Thr Asp Leu Asn Glu Asp Leu Gly Val Trp Val Ile Phe Lys
            840             845             850 att aag acg caa gat ggg cac gca aga cta ggg aat cta gag ttt ctc    2887
Ile Lys Thr Gln Asp Gly His Ala Arg Leu Gly Asn Leu Glu Phe Leu
        855             860             865 gaa gag aaa cca tta gta gga gaa gcg cta gct cgt gtg aaa aga gcg    2935
Glu Glu Lys Pro Leu Val Gly Glu Ala Leu Ala Arg Val Lys Arg Ala
    870             875             880 gag aaa aaa tgg aga gac aaa cgt gaa aaa ttg gaa tgg gaa aca aat    2983
Glu Lys Lys Trp Arg Asp Lys Arg Glu Lys Leu Glu Trp Glu Thr Asn
885             890             895 atc gtt tat aaa gag gca aaa gaa tct gta gat gct tta ttt gta aac    3031
Ile Val Tyr Lys Glu Ala Lys Glu Ser Val Asp Ala Leu Phe Val Asn
900             905             910             915 tct caa tat gat caa tta caa gcg gat acg aat att gcc atg att cat    3079
Ser Gln Tyr Asp Gln Leu Gln Ala Asp Thr Asn Ile Ala Met Ile His
        920             925             930 gcg gca gat aaa cgt gtt cat agc att cga gaa gct t                  3116
Ala Ala Asp Lys Arg Val His Ser Ile Arg Glu Ala
    935             940
```

FIGURE 1-5

INSECT RESISTANT COTTON PLANTS

CROSS-REFERENCE TO RELATED APPLICATIONS

This application is a continuation of Ser. No. 08/151,615, filed Nov. 12, 1993, now abandoned; which is a division of Ser. No. 07/713,624, filed Jun. 10, 1991, now U.S. Pat. No. 6,943,282; which is a file-wrapper-continuation of Ser. No. 07/260,574, filed Oct. 21, 1988, now abandoned; which was a continuation-in-part of Ser. No. 06/848,733, filed Apr. 4, 1986, now abandoned; which was a continuation-in-part of the first filed application in this chain, Ser. No. 06/535,354, filed Sep. 26, 1983, now abandoned, through which the benefit of priority is hereby claimed pursuant to 35 U.S.C. §120.

FIELD OF THE INVENTION

The present invention is in the fields of genetic engineering, plant husbandry, and bacterial bio-affecting compositions, especially those derived from the genus *Bacillus*.

BACKGROUND OF THE INVENTION

Insecticidal Protein. *Bacillus thuringiensis*, a species of bacteria closely related to *B. cereus*, forms a proteinaceous crystalline inclusion during sporulation. This crystal is parasporal, forming within the cell at the end opposite from the developing spore. The crystal protein, often referred to as the δ-endotoxin, has two forms: a nontoxic protoxin of approximate molecular weight (MW) of 130 kilodaltons (kD), and a toxin having an approximate MW of 67 kD. The crystal contains the protoxin protein which is activated in the gut of larvae of a number of insect species. Klowden, M. J. et al. (1983) *Appl. Environ. Microbiol.* 46:312-315, have shown solubilized protoxin from *B. thuringiensis* var. *israelensis* is toxic to *Aedes aegypti* adults. During activation, the protoxin is cleaved into two polypeptides, one or both of which are toxic. In vivo, the crystal is activated by being solubilized and converted to toxic form by the alkalinity and proteases of the gut. In vivo the protoxin may be solubilized by extremely high pH (e.g., pH 12), by reducing agents under moderately basic conditions (e.g., pH 10), or by strong denaturants (guanidium, urea) under neutral conditions (pH 7), and once solubilized, may be activated by the action of the protease trypsin. The crystal protein is reported to be antigenically related to proteins within both the spore coat and the vegetative cell wall. Carbohydrate is not involved in the toxic properties of the protein.

*B. thuringiensis* and its crystalline endotoxin are useful because the crystal protein is an insecticidal protein known to be poisonous to the larvae of over a hundred species of insects, most commonly those from the orders Lepidoptera and Diptera. Insects susceptible to the action of the *B. thuringiensis* crystal protein include, but need not be limited to, those listed in Table 1. Many of these insect species are economically important pests. Plants which can be protected by application of the crystal protein include, but need not be limited to, those listed in Table 2. Different varieties of *B. thuringiensis*, which include, but need not be limited to, those listed in Table 3, have different host ranges (Faust, R. M. et al. [1982] in *Genetic Engineering in the Plant Sciences*, Panapolous, N.J. (ed.), pp. 225-254); this probably reflects the toxicity of a given crystal protein in a particular host. The crystal protein is highly specific to insects; in over two decades of commercial application of sporulated *B. thuringiensis* cells to crops and ornamentals, there has been no known case of effects to plants or non-insect animals. The efficacy and safety of the endotoxin have been reviewed by Faust, R. M. et al., supra. Other useful reviews include those by Fast, P. G. (1981) in *Microbial Control of Pests and Plant Diseases,* 1970-1980, Burges, H. D. (ed.), pp. 223-248; and Huber, H. E., P. Luthy (1981) in *Pathogenesis of Invertebrate Microbial Diseases*, Davidson, E. W. (ed.), pp. 209-234.

The crystal protein gene usually can be found on one of several large plasmids that have been found in *Bacillus thuringiensis*, though in some strains it may be located on the chromosome (Kronstad, J. W. et al. [1983] *J. Bacteriol.* 154:419-428). Several of the genes have been cloned into plasmids that can grow in *E. coli* Whiteley's group (Whiteley, H. R. et al. [1982] in *Molecular Cloning and Gene Regulation in Bacilli*, Ganesan, A. T. et al. (eds.), pp. 131-144; Schnepf, H. E., H. R. Whiteley [1981] *Proc. Natl. Acad. Sci USA* 78:2893-2897; and European patent application 63,949) reported the cloning of the toxin from *B. thuringiensis* var. *kurstaki* strains HD-1-Dipel and HD-73, using the enzymes Sau3AI (under partial digest conditions) and BglII, respectively, to insert large gene-bearing fragments having approximate sizes of 12 kilobasepairs (kbp) and 16 kbp into the BamHI site of the *E. coli* plasmid vector pBR322. The HD-1 crystal protein was observed to be located on a 6.6 kbp HindIII fragment. Crystal protein from the HD-1-Dipel gene which was toxic to larvae, immunologically identifiable, and the same size as the authentic protoxin, was observed to be produced by transformed *E. coli* cells containing pBR322 clones or subclones. This indicated that the *Bacillus* gene was transcribed, probably from its own promoter, and translated in *E. coli*. Additionally, this suggests that the toxic activity of the protein product is independent of the location of its synthesis. That the gene was expressed when the fragment containing it was inserted into the vector in either orientation suggests that transcription was controlled by its own promoter. The transcriptional and translational start sites, as well as the deduced sequence for the amino-terminal 333 amino acids of the HD-1-Dipel protoxin, have been determined by nucleic acid sequence (Wong, H. C. et al. [1983] *J. Biol. Chem.* 258:1960-1967). The insecticidal gene was found to have the expected bacterial ribosome binding and translational start (ATG) sites along with commonly found sequences at −10 and −35 (relative to the 5'-end of the mRNA) that are involved in initiation of transcription in bacteria such as *B. subtilis*. Klier, A. et al. (1982) *EMBO J.* 1:791-799, have reported the cloning of the crystal protein gene from *B. thuringiensis* strain berliner 1715 in pBR322. Using the enzyme BamHI, a large 14 kbp fragment carrying the crystal protein gene was moved into the vector pHV33, which can replicate in both *E. coli* and *Bacillus*. In both *E. coli* and sporulating *B. subtilis*, the pHV33-based clone directed the synthesis of full-size (130 kD) protoxin which formed cytoplasmic inclusion bodies and reacted with antibodies prepared against authentic protoxin. Extracts of *E. coli* cells harboring the pBR322 or pHV33-based plasmids were toxic to larvae. In further work, Klier, A et al. (1983) *Nucl. Acids Res.* 11:3973-3987, have transcribed the berliner crystal protein gene in vitro and have reported on the sequence of the promoter region, together with the first 11 codons of the crystal protein. The bacterial ribosome binding and translational start sites were identified. Though the expected "−10" sequence was identified, no homology to other promoters has yet been seen near −35. Held et al. (1982) *Proc. Natl. Acad. Sci. USA* 77:6065-6069, reported the cloning of a crystal protein gene from the variety kurstaki in the phage g-based cloning vector Charon4A *E. coli* cells infected with one of the Charon clones produced antigen that was the same size as the protoxin (130 kD) and was toxic to larvae. A 4.6 kbp EcoRI fragment of this Charon clone was moved into pHV33 and an *E. coli* plasmid vector, pBR328. Again, 130 kD antigenically identifiable crystal protein was produced by both *E. coli* and *B. subtilis* strains harboring the appropriate plasmids. A *B. thuringiensis* chromosomal sequence which cross-hybridized with the cloned crystal protein gene was identified in *B. thuringiensis* strains which do not produce crystal protein during sporulation.

In addition to the crystal protein, *B. thuringiensis* produces at least three other toxins. Two of them, the α-exotoxin and γ-exotoxin, are phospholipase elements that degrade lipids. *B. cereus* is also known to produce phospholipases (or lecithinases) which are toxic to insect larvae. Other bacterial enzymes which are involved in insect pathogenesis include, but need not be limited to, hyaluronidases, phosphatases, and proteases. Protease produced by *Pseudomonas aeruginosa* has been shown to have a specific affinity to proteins of *Galleria mellonella* larvae (see Lysenko, O., M. Kucera [1971] in *Microbial Control of Insects and Mites*, Burges, H. D., N. W. Hussey (eds.), pp. 205-277).

Chang, S. (1983) *Trends Biotechnol.* 1:100-101, reported that the DNA sequence of a complete HD-1 gene had been publicly presented (ref. 5 therein), and that the HD-1 toxin moiety resides in the amino-terminal 67 kD peptide.

Shuttle Vectors. Shuttle vectors, developed by Ruvidn, G. B., F. M. Ausubel (1981) *Nature* 298:85-88, provide a way to insert foreign genetic materials into position of choice in a large plasmid, virus, or genome. There are two main problems encountered when dealing with large plasmids or genomes. First, the large plasmids may have many sites for each restriction enzyme. Unique site-specific cleavage reactions are not reproducible, and multi-site cleavage reactions followed by ligation lead to great difficulties due to the scrambling of the many fragments whose order and orientation one does not want changed. Second, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell, typically a bacterium of the family Rhizobiaceae (which contains the genus *Agrobacterium*), by a tri-parental mating (Ruvkin and Ausubel, supra), direct transfer of a self-mobilizable vector in a bi-parental mating, direct uptake of exogenous DNA by *Agrobacterium* cells ("transformation," using the conditions of Holsters, M. et al. [1978] *Mol. Gen. Genet.* 163:181-187), by spheroplast fusion of *Agrobacterium* with another bacterial cell, by uptake of liposome-encapsulated DNA, or by infection with a shuttle vector that is based on a virus that is capable of being packaged in vitro. A tri-parental mating involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g., the Ti or Ri plasmids of *Agrobacterium* strains.

After the shuttle vector is introduced into the recipient cell, possible events include a double crossover with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance market. Therefore, when one selects for resistance to both drugs, the only surviving cells are those in which the marker on the shuttle vector has recombined with the recipient genome. If the shuttle vector carries an extra marker, one can then screen for and discard cells that contain plasmids resulting from a single crossover event between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

If the shuttle vector is used to introduce a phenotypically dominant trait (e.g., a novel expressible insecticide structural gene, but not an inactivated oncogenic T-DNA gene), one need not only rely on a double homologous recombination. The cells resulting from a single cross-over event resulting in cointegrate plasmids can transfer the desired trait into plant cells. One may even use a variant shuttle vector having a single uninterrupted sequence of T-DNA. However, as the resulting T-DNA will now contain a tandem duplication, one must be vigilant regarding a possible rare deletion of the shuttle vector by a single homologous recombination event occurring between the two homologous sequences in either the *Agrobacterium* or plant cells.

Shuttle vectors have proved useful in manipulation of *Agrobacterium* plasmids: see Garfinkel, D. J. et al. (1981) *Cell* 27:143-153; Matzke, A. J. M., M.-D. Chilton (1981) *J. Mol. Appl. Genet.* 1:39-49; and Leemans, J. et al. (1981) *J. Mol. Appl. Genet.* 1:149-164, who referred to shuttle vectors by the term "intermediate vectors."

A recently disclosed variation of the shuttle vector system for inserting changes into large DNA molecules is the "suicide vector." In this system, as described by Puhler, A. et al., U.S. Pat. No. 4,626,504, and Simon, R. et al. (November 1983) "A Broad Host Range Mobilization System for In Vivo Genetic Engineering: Transposon Mutagenesis in Gram-Negative Bacteria," *Biotechnology*, pp. 784-791, the shuttle vector is incapable of being maintained within the recipient cell. This property eliminates the need to introduce an incompatible plasmid into the recipient cell in order to exclude the shuttle vector as is commonly done during a triparental mating. All vectors which do not integrate into some already present DNA effectively "commit suicide" by not being replicated. As can be done with traditional types of shuttle vectors, one may distinguish between double and single homologous recombination by screening for an antibiotic resistance gene which is not between the two regions of homology. Use of a pBR322-based suicide vector to transfer DNA sequences into a Ti plasmid has been reported by Van Haute, E. et al. (1983) *EMBO J.* 2:411-417, and Comai, L. et al. (1982) *Plant Mol. Biol.* 1:291-300.

An alternative to the use of shuttle vectors for introduction of novel DNA sequences into T-DNA by means of homologous recombination involves bacterial transposons. As described in the section *Agrobacterium*-Genes on the TIP Plasmids, transposons can "jump" into the T-DNA of a TIP plasmid (e.g., see Garfinkel, D. J. et al. [1981] *Cell* 27:143-153). Should the transposon be modified in vitro by the insertion of the novel sequence, that novel DNA can be transferred into the TIP plasmid's T-DNA by the transposon. The TIP can then transfer the novel DNA/transposon/T-DNA combination to a plant cell where it will be stably integrated.

*Agrobacterium* —Overview. Included within the Gram-negative bacterial family Rhizobiaceae in the genus *Agrobacterium* are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tissue usually produces one or more amino acid derivatives, known as opines, not normally produced by the plant, which are catabolized by the infecting bacteria. Known opines have been classified into three main families whose type members are octopine, nopaline, and agropine. The cells of inappropriately growing tissues can be grown in culture and, under appropriate conditions, be regenerated into whole plants that retain certain transformed phenotypes.

Virulent strains of *Agrobacterium* harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, tms, respectively, result in large tumors (in tobacco), a propensity to generate roots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes both Ti and Ri plasmids. The integrated segment of a TIP is termed herein "T-DNA" (transferred DNA), whether derived from a Ti plasmid or a Ri plasmid.

Chilton, M.-D. (June 1983) *Sci. Amer.* 248(6):50-59, has recently provided an introductory article on the use of Ti plasmids as vectors. Recent general reviews of *Agrobacterium*-caused disease include those by Merlo, D. J. (1982) *Adv. Plant Pathol.* 1:139-178; Ream, L. W., Gordon, M. P. (1982) *Science* 218:854-859; Bevan, M. W.; M.-D. Chilton (1982) *Ann. Rev. Genet.* 16:357-384; Kahl, G., J. Schnell (1982) *Molecular Biology of Plant Tumors*; and Barton, K. A., M.-D. Chilton (1983) *Methods Enzymol.* 101:527-539.

*Agrobacterium* —Infection of Plant Tissues. Plant cells can be transformed by *Agrobacterium* in a number of methods known in the art which include, but are not limited to, co-cultivation of plant cells in culture with *Agrobacterium*, direct infection of a plant, fusion of plant protoplasts with *Agrobacterium* spheroplasts, direct transformation by uptake of free DNA by plant cell protoplasts, transformation of protoplasts having partly regenerated cell walls with intact bacteria, transformation of protoplasts by liposomes containing T-DNA, use of a virus to carry in the T-DNA, microinjection, and the like. Any method will suffice as long as the gene is reliably expressed and is stably transmitted through mitosis and meiosis.

The infection of plant tissue by *Agrobacterium* is a simple technique well known to those skilled in the art (for an example, see Butcher, D. N. et al. [1980] in *Tissue Culture Methods for Plant Pathologists*, Ingram, D. S., J. P. Helgeson (eds.), pp. 203-208). Typically, a plant is wounded by any of a number of ways, which include cutting with a razor, puncturing with a needle, or rubbing with an abrasive. The wound is then inoculated with a solution containing tumor-inducing bacteria. An alternative to the infection of intact plants is the inoculation of pieces of tissues such as potato tuber discs (Anand, D. K., G. T Heberlein [1977] *Amer. J. Both.* 64:153:158) or segments of tobacco stems (Barton, K. A. et al. [1983] *Cell* 32:1033-1043. After induction, the tumors can be placed in tissue culture on media lacking phytohormones. Hormone-independent growth is typical of transformed plant tissue and is in great contrast to the usual conditions of growth of such tissue in culture (Braun, A. C. [1956] *Cancer Res.* 16:53-56).

*Agrobacterium* is also capable of infecting isolated cells and cells grown in culture (Marton, L. et al. [1979] *Nature* 277:129-131) and isolated tobacco mesophyll protoplasts. In the latter technique, after allowing time for partial regeneration of new cell walls, *Agrobacterium* cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism. Other workers (Horsch, R. B., R. T. Fraley [18 Jan. 1983] 15th Miami Winter Symposium) have reported transformations by co-cultivation, leading to a high rate (greater than 10%) of calli displaying hormone-independent growth, with 95% of those calli making opines. Davey, M. R. et al. (1980) in Ingram and Helgeson, supra, pp. 209-219, describe the infection of older cells that had been regenerated from protoplasts.

Plant protoplasts can be transformed by the direct uptake of TIP plasmids. Davey, M. R. et al. (1980) *Plant Sci Lett.* 18:307-313, and Davey, M. R. et al. (1980) in Ingram and Helgeson, supra, were able to transform Petunia protoplasts with the Ti plasmid in the presence of poly-L-α-ornithine to a phenotype of opine synthesis and hormone-independent growth in culture. It was later shown (Draper, J. et al. [1982]

Plant and Cell Physiol 23:451-458; Davey, M. R. et al. [1982] in *Plant Tissue Culture*, Fujiwara, A. (ed.), pp. 515-516) that polyethylene glycol stimulated Ti plasmid uptake and that some T-DNA sequences were integrated into the genome. Krens, F. A. et al. (1982) *Nature* 296:72-74, reported similar results using polyethylene glycol followed by a calcium shock, though their data suggests that the integrated T-DNA included flanking Ti plasmid sequences.

An alternative method to obtain DNA uptake involves the use of liposomes. The preparation of DNA containing liposomes is taught by Papahadjopoulos in U.S. Pat. Nos. 4,078,052 and 4,235,871. Preparations for the introduction of Ti-DNA via liposomes have been reported (Nagata, T. et al. [1982] in Fujiwara, supra, pp. 509-510; and Nagata, T. [1981] *Mol. Gen. Genet.* 184:161-165). An analogous system involves the fusion of plant and bacterial cells after removal of their cell walls. An example of this technique is the transformation of *Vinca* protoplast by *Agrobacterium* spheroplasts reported by Hasezawa, S. et al. (1981) *Mol. Gen. Genet.* 182:206-210. Plant protoplasts can take up cell wall delimited *Agrobacterium* cells (Hasezawa, S. et al. [1982] in Fujiwara, supra, pp. 517-518).

T-DNA can be transmitted to tissue regenerated from a fusion of two protoplasts, only one of which had been transformed (Wullens, G. J. et al. [1980] *Theor. Appl. Genet.* 56:203-208). As detailed in the section on Regeneration of Plants, T-DNA can pass through meiosis and be transmitted to progeny as a simple Mendelian trait.

*Agrobacterium* —Regeneration of Plants. Differentiated plant tissues with normal morphology have been obtained from crown gall tumors. Braun, A. C., H. N. Wood (1976) *Proc. Natl. Acad. Sci. USA* 73:496-500, grafted tobacco teratomas onto normal plants and were able to obtain normally appearing shoots which could flower. The shoots retained the ability to make opines and to grow independently of phytohormones when placed in culture. In the plants screened, these tumorous phenotypes were not observed to be transmitted to progeny, apparently being lost during meiosis (Turgeon, R. et al. [1976] *Proc. Natl. Acad. Sci. USA* 73:3562-3564). Plants which had spontaneously lost tumorous properties, or which were derived from teratoma seed, were initially shown to have lost all their T-DNA (Yang, F.-M. et al. [1980] *In Vitro* 16:87-92; Yang, F. et al. [1980] *Mol. Gen. Genet.* 177:707-714; Lemmers, M. et al. [1980] *J. Mol. Biol.* 144:353-376). However, later work with plants that had become revertants after hormone treatment (1 mg/1 kinetin) showed that plants that had gone through meiosis, though losing T-DNA genes responsible for the transformed phenotype, could retain sequences homologous to both ends of T-DNA (Yang, F., R. B. Simpson [1981] *Proc. Natl. Acad. Sci. USA* 78:4151-4155). Wullems, G. J. et al. [1981] *Cell* 24:719-724, further demonstrated that genes involved in opine anabolism were capable of passing through meiosis though the plants were male sterile and that seemingly unaltered T-DNA could be inherited in a Mendelian fashion (Wullems, G. J. [1982] in Fujiwara, supra). Otten, L. et al. (1981) *Mol. Gen. Genet.* 183:209-213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. In further experiments, DeGreve, H. et al. (1982) *Nature* 300:752-755, have found that octopine synthase can be inherited as a single dominant Mendelian gene. However, the T-DNA had sustained extensive deletions of functions other than ocs while undergoing regeneration from callus. Similar experiments with a tmr (root-inducing) mutant showed that full-length T-DNA could be transmitted through meiosis to progeny, that in those progeny nopaline genes could be expressed, though at variable levels, and that co-transformed yeast alcohol dehydrogenase I gene was not expressed (Barton, K. A. et al. [1983] *Cell* 32:1033-1043. It now appears that regenerated tissues which lack T-DNA sequences are probably descended from untransformed cells which "contaminate" the tumor (Ooms, G. et al. [1982] *Cell* 30:589-597). Recent work by Binns, A. N. (1983) *Planta* 158:272-279, indicates that tumorigenic genes, in this case tmr, can be "shut off" during regeneration and "turned back on" by placing regenerated tissue in culture.

Roots resulting from transformation from *A. rhizogenes* have proven relatively easy to regenerate directly into plantlets (Chilton, M.-D. et al. [1982] *Nature* 295:432-434).

*Agrobacterium* —Genes on the TIP Plasmids. A number of genes have been identified within the T-DNA of the TIP plasmids. About half a dozen octopine plasmid T-DNA transcripts have been mapped (Gelvin, S. B. et al. [1982] *Proc. Natl. Acad. Sci. USA* 79:76-80; Willmitzer, L. et al. [1982] *EMBO J.* 1:139-146) and some functions have been assigned (Leemans, J. et al. [1982] *EMBO J.* 1:147-152). Some of these transcripts, specifically those in the region encoding tmr and tms, can also be transcribed in prokaryotic cells (Schroder, G. et al. [1983] *EMBO J.* 2:403-409). The four genes of an octopine type plasmid that have been well defined by transposon mutagenesis include tms, tmr, and tml (Garfinkel, D. J. et al. [1981] *Cell* 27:143-153). Ti plasmids which carry mutations in these genes respectively incite tumorous calli of *Nicotiana tabacum* which generate shoots, proliferate roots, and are larger than normal. In other hosts, mutants of these genes can induce different phenotypes (see Bevan, M. W., M.-D. Chilton [1982] *Ann. Rev. Genet.* 16:357-384). The phenotypes of tms and tmr are correlated with differences in the phytohormone levels present in the tumor. The differences in cytokinin:auxin ratios are similar to those which in culture induce shoot or root formation in untransformed callus tissue (Aidyoshi, D. E. et al. [1983] *Proc. Natl. Acad. Sci. USA* 80:407-411). T-DNA containing a functional gene for either tms or tmr alone, but not functional tml alone, can promote significant tumor growth. Promotion of shoots and roots is respectively stimulated and inhibited by functional tml (Ream, L. W. et al. [1983] *Proc. Natl. Acad. Sci. USA* 80:1660-1664). Mutations of T-DNA genes do not seem to affect the insertion of T-DNA into the plant genome (Leemans et al. [1982] supra; Ream et al. [1983] supra). The ocs gene encodes octopine synthase, which has been sequenced by De Greve, H. et al. (1982) *J. Mol. Appl. Genet.* 1:499-511. It does not contain introns (intervening sequences commonly found in eukaryotic genes which are post-transcriptionally spliced out of the messenger precursor during maturation of the mRNA). It does have sequences that resemble a eukaryotic transcriptional signal ("TATA box") and a polyadenylation site. All of the signals necessary for expression of the ocs gene are found within 295 bp of the ocs transcriptional start site (Koncz, C. et al. [1983] *EMBO J.* 2:1597-1603).

Nopaline Ti plasmids encode the nopaline synthase gene (nos), which has been sequenced by Depicker, A et al. (1982) *J. Mol. Appl. Genet.* 1:561-573. As was found with the ocs gene, nos is not interrupted by introns. It has two putative polyadenylation sites and a potential "TATA box." In contrast to ocs, nos is preceded by a sequence which may be a transcriptional signal known as a "CAT box." All of the signals necessary for expression of the nos gene are found within 261 bp of the nos transcriptional start site (Koncz, C.

et al., supra). A gene for agrocinopine synthase and genes equivalent to tms and tmr have been identified on a nopaline-type plasmid (Joos, H. et al. [1983] *Cell* 32:1057-1067), and a number of transcripts have been mapped (Willmitzer, L. et al. [1983] *Cell* 32:1045-1056). McPhersson, J. C. et al. (1980) *Proc. Natl. Acad. Sci. USA* 77:2666-2670, reported the in vitro translation of T-DNA-encoded mRNAs from crown gall tissues.

Transcription from hairy root T-DNA has also been detected (Willmitzer, L. et al. [1982] *Mol. Gen. Genet.* 186:16-22). Functionally, the hairy root syndrome appears to be the equivalent of a crown gall tumor incited by a Ti plasmid mutated in tmr (White, F. F., E. W. Nester [1980] *J. Bacteriol.* 144:710-720).

In eukaryotes, methylation (especially of cytosine residues) of DNA is correlated with transcriptional inactivation; genes that are relatively under-methylated are transcribed into mRNA. Gelvin, S. B. et al. (1983) *Nucl. Acids Res.* 11:159-174, has found that the T-DNA in crown gall tumors is always present in at least one unmethylated copy. That the same genome may contain numerous other copies of T-DNA which are methylated suggests that the copies of T-DNA in excess of one may be biologically inert (see also Ooms, G. et al. [1982] *Cell* 30:589-597).

The Ti plasmid encodes other genes which are outside of the T-DNA region and are necessary for the infection process (see Holsters, M. et al. [1980] *Plasmid* 3:212-230, for nopaline plasmids; and De Greve, H. et al. [1981] *Plasmid* 6:235-248; Garfinkel, D. J., E. W. Nester [1980] *J. Bacteriol.* 144:732-743; and Ooms, G. [1980] *J. Bacteriol.* 144:82-91, for octopine plasmids). Most important are the one genes, which, when mutated, result in Ti plasmids incapable of oncogenicity. (These loci are also known as vir, for virulence.) Several one genes have been accurately mapped and have been found to be located in regions conserved among various Ti plasmids (Klee, H. J. et al. [1983] *J. Bacteriol.* 153:878-883; Iyer, V. N. et al. [1982] *Mol. Gen. Genet.* 188:418-424). The one genes function in trans, being capable of causing the transformation of plant cells with T-DNA of a different plasmid type and physically located on another plasmid (Hille, J. et al. [1982] *Plasmid* 7:107-118); Klee, H. J. et al. [1982] *J. Bacteriol.* 150:327-331; de Framond, A-J. et al. [1983] *Biotechnol.* 1:262-269). Nopaline Ti DNA has direct repeats of about 25 base pairs immediately adjacent to the left and right borders of the T-DNA which might be involved in either excision from the Ti plasmid or integration into the host genome (Yadav, N. S. et al. [1982] *Proc. Natl. Acad. Sci. USA* 79:6322-6326), and a homologous sequence has been observed adjacent to an octopine T-DNA border (Simpson, R. B. et al. [1982] *Cell* 29:1005-1014). Opine catabolism is specified by the occ and noc genes, respectively, of octopine- and nopaline-type plasmids. The Ti plasmid also encodes functions necessary for its own reproduction including an origin of replication. Ti plasmid transcripts have been detected in *A. tumefaciens* cells by Gelvin, S. B. et al. (1981) *Plasmid* 6:17-29, who found that T-DNA regions were weakly transcribed along with non-T-DNA sequences. Ti plasmid-determined characteristics have been reviewed by Merlo, supra (see especially Table II), and Ream and Gordon, supra.

*Agrobacterium* —TIP Plasmid DNA. Different octopine-type Ti plasmids are nearly 100% homologous to each other when examined by DNA hybridization (Currier, T. C., E. W. Nester [1976] *J. Bacteriol.* 126:157-165) or restriction enzyme analysis (Sciaky, D. et al. [1978] *Plasmid* 1:238-253). Nopaline-type Ti plasmids have as little as 67% homology to each other (Currier and Nester, supra). A survey revealed that different Ri plasmids are very homologous to each other (Costantino, P. et al. [1981] *Plasmid* 5:170-182). Drummond, N. H., M.-D. Chilton (1978) *J. Bacteriol.* 136:1178-1183, showed that proportionally small sections of octopine- and nopaline-type Ti plasmids were homologous to each other. These homologies were mapped in detail by Engler, G. et al. (1981) *J. Mol. Biol.* 152:183-208. They found that three of the four homologous regions were subdivided into three (overlapping the T-DNA), four (containing some one genes), and nine (having one genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of *Rhizobium*, a different genus in the family Rhizobiaceae (Prakash, R. K. et al. [1982] *Plasmid* 7:271-280). The order of the four regions is not conserved, though they are all oriented in the same direction. Part of the T-DNA sequences is very highly conserved between nopaline and octopine plasmids (Chilton, M.-D. et al. [1978] *Nature* 275:147-149; Depicker, A et al. [1978] *Nature* 275:150-153). Ri plasmids have been shown to have extensive homology among themselves, and to both octopine (White, F. F., E. W. Nester [1980] *J. Bacteriol.* 144:710-720) and nopaline (Risuleo, G. et al. [1982] *Plasmid* 7:45-51) Ti plasmids, primarily in regions encoding one genes. Ri T-DNA contains extensive though weak homologies to T-DNA from both types of Ti plasmid (Willmitzer, L. et al. [1982] *Mol. Gen. Genet.* 186:16-22). Plant DNA from uninfected *Nicotiana glauca* contains sequences, referred to as cT-DNA (cellular T-DNA), that show homology to a portion of the Ri T-DNA (White, F. F. et al. [1983] *Nature* 301:348-350; Spano, L. et al. [1982] *Plant Mol. Biol.* 1:291-300). Huffman, G. A. et al. (1983) *J. Bacteriol.*, have mapped the region of cross-hybridization and have shown that Ri plasmid, pRiA4b, is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA.

It has been shown that a portion of the Ti (Chilton, M.-D. et al. [1977] *Cell* 11:263-271) or Ri (Chilton, M.-D. [1982] *Nature* 295:432-434; White, F. F. et al. [1982] *Proc. Natl. Acad. Sci. USA* 79:3193-3197; Willmitzer, L. [1982] *Mol. Gen. Genet.* 186:16-22) plasmid is found in the DNA of tumorous plant cells. The transferred DNA is known as T-DNA. T-DNA is integrated into the host DNA (Thomashow, M. F. et al. [1980] *Proc. Natl. Acad. Sci. USA* 77:6448-6452; Yadav, N. S. et al. [1980] *Nature* 287:458-461) in the nucleus (Nuti, M. P. et al. [1980] *Plant Sci. Lett.* 18:1-6; Willmitzer, L. et al. [1980] *Nature* 287:359-361; Chilton M.-D. et al. [1980] *Proc. Natl. Acad. Sci. USA* 77:4060-4064).

Thomashow, M. F. (1980) supra, and Thomashow, M. F. et al. (1980) *Cell* 19:729-739, found the T-DNA from octopine-type Ti plasmids to have been integrated in two separate sections, TL-DNA and TR-DNA, left and right T-DNAs, respectively. The copy numbers of TR and TL can vary (Merlo, D. J. et al. [1980] *Mol. Gen. Genet.* 177:637-643). A core of T-DNA is highly homologous to nopaline T-DNA (Chilton et al. [1978] supra; and Depicker et al. [1978] supra), is required for tumor maintenance, is found in TL, is generally present in one copy per cell, and codes for the genes tms, tmr, and tml. On the other hand, TR can be totally dispensed with (De Beuckeleer, M. et al. [1981] *Mol.*

Gen. Genet. 183:283-288; Ooms, G. et al. [1982] *Cell* 30:589-597), though found in a high copy number (Merlo et al. [1980] supra). Ooms, G. et al. (1982) *Plasmid* 7:15-29, hypothesized that TR is involved in T-DNA integration, though they find that when TR is deleted from the Ti plasmid, *A. tumefaciens* does retain some virulence. Ooms, G. et al. (1982) *Cell*, supra, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (Simpson, R. B. et al. [1982] *Cell* 29:1005-1014).

In contrast to the situation in octopine-type tumors, nopaline T-DNA is integrated into the host genome in one continuous fragment (Lemmers, M. et al. [1980] *J. Mol. Biol.* 144:353-376; Zambryski, P. et al. [1980] *Science* 209:1385-1391). Direct tandem repeats were observed. T-DNA of plants regenerated from teratomas had minor modifications in the border fragments of the inserted DNA (Lemmers et al., supra). Sequence analysis of the junction between the right and left borders revealed a number of direct repeats and one inverted repeat. The latter spanned the junction (Zambryski et al. [1980] supra). The left junction has been shown to vary by at least 70 base pairs while the right junction varies no more than a single nucleotide (Zambryski, P. et al. [1982] *J. Mol. Appl. Genet.* 1:361-370). Left and right borders in junctions of tandem arrays were separated by spacers which could be over 130 bp. The spacers were of unknown origin and contained some T-DNA sequences. T-DNA was found to be integrated into both repeated and low copy number host sequences. H. Joos et al. (1983) *Cell* 32:1057-1067, have shown that virulence is not eliminated after deletion of either of the usual nopaline T-DNA borders.

Simpson et al. (1982) supra, and Zambryski et al. (1980) supra, have suggested that direct repeats in the border regions are involved in integration of T-DNA into plant DNA. That T-DNA having borders from two different Ti plasmids are less specifically integrated than are homologous borders supports this suggestion (Ooms, G. et al. [1982] *Plant Mol. Biol.* 1:265-276).

Yadav, N. S. et al. (1982) *Proc. Natl. Acad. Sci. USA* 79:6322-6326, have found a chi site, which in the bacteriophage (Greek symbol) augments general recombination in the surrounding DNA as far as 10 kilobases away, in a nopaline Ti plasmid just outside the left end of the T-DNA. Simpson, R. B. et al. (1982) *Cell* 29:1005-1014, have not observed a chi sequence in an octopine Ti plasmid, though the possible range of action does not eliminate the possibility of one being necessary and present but outside of the region sequenced. The significance of the chi in the Ti plasmid is not known. If the chi has a function, it is probably used in *Agrobacterium* cells and not in the plants, as chi is not found within the T-DNA.

*Agrobacterium*—Manipulations of the TIP Plasmids. As detailed in the section on Shuttle Vectors, technology has been developed for the introduction of altered DNA sequences into desired locations on a TIP plasmid. Transposons can be easily inserted using this technology (Garfinkel, D. J. et al. [1981] *Cell* 27:143-153). Hernalsteen, J.-P. et al. (1980) *Nature* 287:645-656, have shown that a DNA sequence (here a bacterial transposon) inserted into T-DNA in the Ti plasmid is transferred and integrated into the recipient plant's genome. Though insertion of foreign DNA has been done with a number of genes from different sources, to date foreign genes have not usually been expressed under control of their own promoters. Sources of these genes include alcohol dehydrogenase (Adh) from yeast (Barton, K. A. et al. [1983] *Cell* 32:1033-1043), AdhI (Bennetzen, J., unpublished) and zein from corn, interferon and globin from mammals, and the mammalian virus SV40 (Schell, J., unpublished). However, when the nopaline synthase gene was inserted into octopine T-DNA and transformed into plant tissue, it was found to be fully functional (Fink, C. L. [1982] M. S. thesis, University of Wisconsin-Madison). The gene encoding phaseolin, the storage protein found in seeds of the bean *Phaseolus vulgaris* L., has been transferred into and expressed in sunflower tumors. This latter work constitutes the first example of a transferred plant gene being expressed under control of its own promoter in foreign plant tissue. Transcription started and stopped at the correct positions, and introns were post-transcriptionally processed properly (Hall, T. C. et al., U.S. application Ser. No. 06/485,613, which is hereby incorporated by reference). Hosters, M. et al. (1982) *Mol. Gen. Genet.* 185:283-289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (Cohen and Boyer, U.S. Pat. No. 4,237,224). Deletions with one predetermined end can be created by the improper excision of transposons (Koekman, B. P. et al. [1979] *Plasmid* 2:343-357, and Ooms, G. et al. [1982] *Plasmid* 7:15-29). Hille, J., R. Schilperoot (1981) *Plasmid* 6:151-154, have demonstrated that deletions having both ends at predetermined positions can be generated by the use of two transposons. The technique can also be used to construct "recombinant DNA" molecules in vivo.

The nopaline synthase gene has been used for insertion of DNA segments coding for drug resistance that can be used to select for transformed plant cells. In plant cells, the kanamycin resistance gene from Tn5 is not transcribed under control of its own promoter (Kemp, J. D. et al. [18 May 1982] Beltsville Symp. VII, Beltsville, Md. [1983] in *Genetic Engineering: Applications to Agriculture*, Owens, L. D. (ed.); and Fink, C. L. [1982] supra). Bevan, M. W. et al. (1983) *Nature* 340:184-187 and Fraley, R. T. et al. (1983) *Proc. Natl. Acad. Sci. USA* 80:4803-4807, have inserted the kanamycin resistance gene (neomycin phosphotransferase II) from Tn5 behind (i.e., under control of) the nopaline promoter. The construction was used to transform plant cells which in culture displayed resistance to kanamycin and its analogs such as G418. Schell, J. et al. (18 Jan. 1983) 15th Miami Winter Symp. (see also Marx, J. L. [1983] *Science* 219:830), reported a similar construction, in which the methotrexate resistance gene (dihydrofolate reductase) from Tn7 was placed behind the nopaline synthase promoter. Transformed cells were resistant to methotrexate. Similarly, Hererra-Estrella, L. et al. (1983) *Nature* 303:209-213, have obtained expression in plant cells of enzymatic activity for octopine synthase and chloramphenicol acetyltransferase, an enzyme which in bacteria confers resistance to chloramphenicol, by placing the structural genes for these two enzymes under control of nos promoters.

Hall, T. C. et al., U.S. application Ser. No. 06/485,614, which is hereby incorporated by reference, have fused the ocs promoter and the 5' end of the octopine synthase structural gene to the structural gene for the bean seed protein phaseolin. A fusion protein having the amino terminus of octopine synthase and lacking the amino terminus of phaseolin was produced under control of the T-DNA promoter. The introns, which were contributed by the phaseolin sequences, were post-transcriptionally processed properly.

de Framond, A. J. et al. (1983) *Biotechnol.* 1:262-269, have reported on the construction of a "mini-Ti plasmid." In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumefaciens* and lacked almost all non-T-DNA Ti sequences. By itself, this plasmid was not able to transform plant cells. However, when placed in an *A. tumefaciens* strain containing an octopine Ti plasmid, tumors were induced which synthesized both octopine and nopaline. The mini-Ti plasmid has also been transferred into plant cells when complemented with a Ti plasmid deleted for its own T-DNA. These results indicated that the non-T-DNA functions acted in trans with T-DNA, that the missing nopaline Ti plasmid functions were complemented by the octopine Ti plasmid, and that the nopaline "mini-Ti" was functional in the transformation of plant cells. A similar pair of complementing plasmids, each containing either octopine T-DNA or one genes, has been constructed by Hoekema, A. et al. (1983) *Nature* 303:179-180.

Chilton et al. (18 Jan. 1983) 15th Miami Winter Symp., also reported on the construction of a "micro-Ti" plasmid made by resectioning the mini-Ti with SmaI to delete essentially all of T-DNA but the nopaline synthase gene and the left and right borders. The micro-Ti was inserted into a modified pRK290 plasmid that was missing its SmaI site, and was employed in a manner similar to mini-Ti, with comparable results.

BRIEF SUMMARY OF THE INVENTION

One object of this invention is to confer pest resistance, specifically insect resistance, to a plant. In pursuance of this goal, other objects are to stably insert a gene coding for an insecticidal protein into the genome of the plant cell, to have this gene expressed in plant tissues, for the expression to be either regulated or constitutive, and for the plant tissues to be in a normal plant. Another object is to provide novel specialized insecticidal tissues for a plant, in particular to provide a means for producing on a normal plant, preferably a dicot, a gall which contains within its tissue an insecticidal protein. Other objects and advantages will become evident from the following description.

The invention disclosed herein provides a plant comprising a genetically modified plant cell having an insecticide structural gene introduced and expressed therein under control of a plant expressible promoter Further, the invention provides plant tissue comprising a plant cell whose genome includes T-DNA comprising an insecticide structural gene inserted in such orientation and spacing with respect to a plant expressible promoter as to be expressible in the plant cell under control of that promoter. Also provided are novel strains of bacteria containing and replicating T-DNA, as defined herein, the T-DNA being modified to contain an inserted insecticide structural gene in such orientation and spacing with respect to a plant expressible promoter as to be expressible in a plant cell under control of said promoter. Further, the invention provides novel plasmids having the ability to replicate in *E. coli* and comprising T-DNA, and further comprising an insecticide structural gene inserted within T-DNA contained within the plasmid, in such manner as to be expressible in a plant cell under control of a plant expressible promoter. Additionally, this invention discloses novel plasmids wherein the insecticide structural gene is capable of expression in *E. coli* or *Bacillus subtilis*, and furthermore discloses strains of bacteria harboring said bacterial expression plasmids.

The invention is exemplified in one of its embodiments by the insertion of the full length structural gene of *Bacillus thuringiensis* insect toxic protein into a sub-Ti plasmid so that the toxin gene is placed under the control of T-DNA plant active regulation sequences (ORF24). The sub-Ti plasmid containing the plant expressible crystal protein gene was introduced into tobacco cells. Tobacco and tomato plants regenerated from these transformed cells were found to express crystal protein at levels measurable by enzyme-linked immunosorbent assay (ELISA) techniques, but also the leaves of these plants were found to be toxic to insect larvae.

The present invention comprises an insecticide structural gene under control of a promoter expressible in plant cells, said promoter/gene combination being inserted into a plant cell by any means known in the art. More specifically, in its preferred embodiment, the invention disclosed herein further comprises expression in plant cells of an insecticide structural gene under control of a plant expressible promoter, after introduction via T-DNA, that is to say, by inserting the insecticide structural gene into T-DNA under control of a plant expressible promoter and introducing the T-DNA containing the insert into a plant cell using known means.

The invention is useful for genetically modifying plant tissues and whole plants by inserting useful insecticide structural genes from various bacterial species or strains. Such useful insecticide structural genes include, but are not limited to, the genes coding for insecticidal proteins as defined below, especially the crystal protein of *Bacillus thuringiensis*, related proteins, and the like. Truncated and modified genes, for example as described in U.S. patent application Ser. No. 06/617,321, incorporated herein by reference, and synthetic genes, for example as described in U.S. patent application Ser. No. 06/242,482, incorporated herein by reference, may also be used. The invention is exemplified by introduction and expression of structural genes for a crystal protein from *B. thuringiensis* var. *kurstaki* HD-73 or *B. thuringiensis* var. *tenebrionis* into cotton, tobacco, potato, tomato, and maize plant cells. Once plant cells expressing an insecticide structural gene under control of a plant expressible promoter are obtained, plant tissues and whole plants can be regenerated therefrom using methods and techniques well known in the art. The regenerated plants are then reproduced by conventional means, and the introduced genes can be transferred to other strains and cultivars by conventional plant breeding techniques.

The introduction and expression of the structural gene for an insecticidal protein can be used to protect a crop from infestation with insect larvae such as hornworm (*Manduca* sp.) or European corn borer (*Ostrinia nubilalis*). Other uses of the invention exploiting the properties of other insecticide structural genes introduced into other plant species will be readily apparent to those skilled in the art. The invention in principle applies to any introduction of an insecticide structural gene into any plant species into which foreign DNA (in the preferred embodiment, T-DNA) can be introduced and in which said DNA can remain stably replicated. In general these taxa presently include, but are not limited to, gymnosperms and dicotyledonous plants, such as sunflower (family Compositeae), tobacco (family Solanaceae), alfalfa, soybeans and other legumes (family Leguminoseae), cotton (family Malvaceae), and most vegetables as well as monocotyledonous plants. The useful plants produced by the method of this invention comprise tissues toxic to insects when ingested. Pests which may be controlled by means of the present invention and the crops that may be protected from them include, but are not limited to, those listed in Tables 1 and 2, respectively. Because of its susceptibility to a number of larvae, cotton is an ideal choice for the insertion of an insecticidal protein gene. Each of the following is a major cotton pest and is also susceptible to the *B. thuringiensis* insecticidal protein: *Heliothis zea* (cotton bollworm), *Pectinophora gossypiella* (pink bollworm), *Heliothis virescens* (tobacco budworm), *Trichoplusia ni* (cabbage looper). Application of insecticidal protein prepared from sporulating *B. thuringiensis* does not control insects such as the pink bollworm in the field because of their particular life cycles and feeding habits. A plant containing in its tissues insecticidal protein will control this recalcitrant type of insect, thus providing advantage over prior insecticidal uses of *B. thuringiensis*. By incorporation of the insecticidal protein into the tissues of a plant, the present invention additionally provides advantage over such prior uses by eliminating instances of nonuniform application and the costs of buying and applying insecticidal preparations to a field. Also, the present invention eliminates the need for careful timing of application of such preparations since small larvae are most sensitive to insecticidal protein and the protein is always present, minimizing crop damage that would otherwise result from preapplication larval foraging.

BRIEF DESCRIPTION OF THE DRAWINGS

FIG. 1 presents the sequence of the crystal protein gene of p123/58-10, described in Example 1.

DETAILED DESCRIPTION OF THE INVENTION

Figure 2:
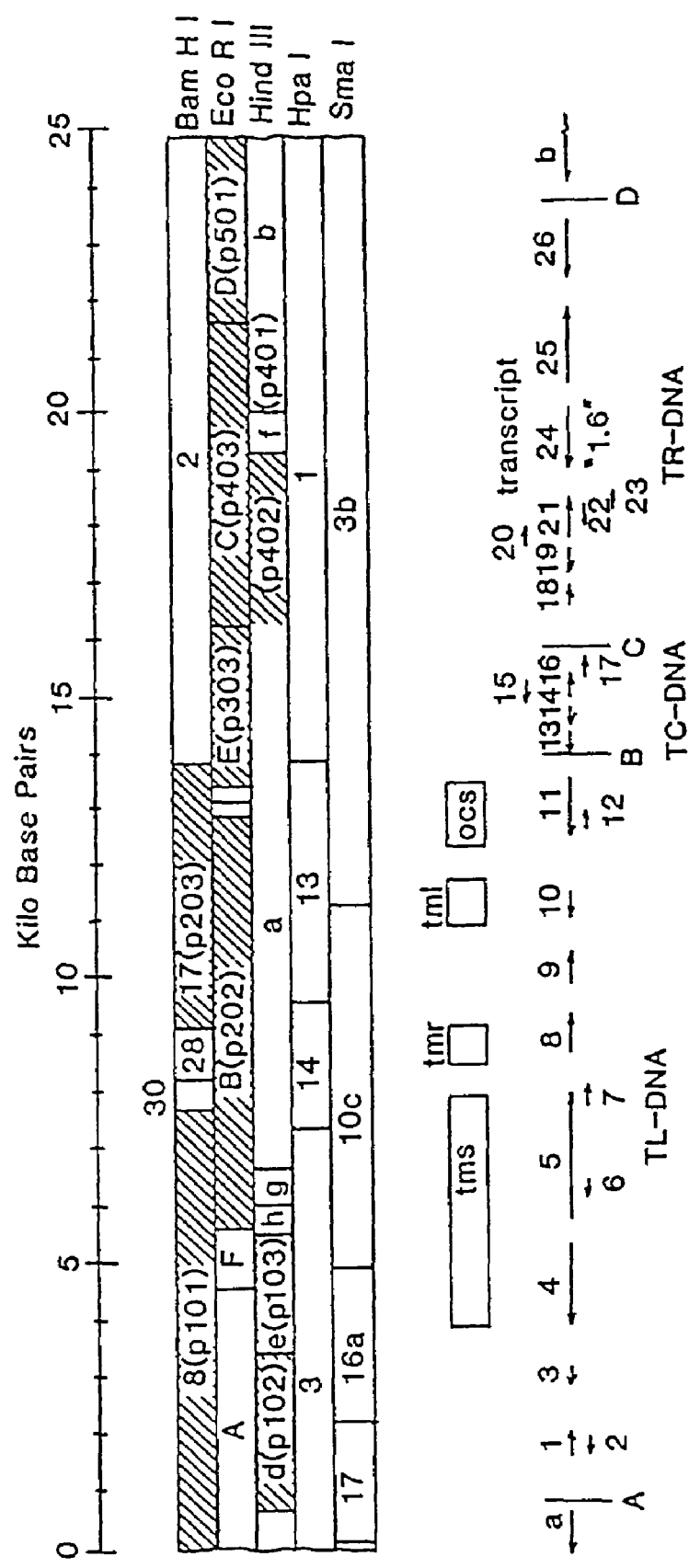
FIG. 2 presents a map of restriction sites and transcripts of the T-DNA of pTi15955.

The following definitions are provided in order to remove ambiguities to the intent or scope of their usage in the specification and claims.

T-DNA: a segment of DNA derived from the transformation-inducing principle (TIP) which becomes integrated in the plant genome. As used herein, the term includes DNA originally derived from any tumor-inducing strain of *Agrobacterium* including *A. tumefaciens* and *A. rhizogenes*, the inserted segment of the latter sometimes referred to in the prior art as R-DNA. In addition, as used herein the term T-DNA includes any alterations, modifications, mutations, substitutions, insertions, and deletions, either naturally occurring or introduced by laboratory procedures, a principal structural requirement, and limitation to such modifications being that sufficient of the right and left ends of naturally-occurring T-DNAs be present to insure the expected formation of stable integration in the transformed plant cell genome which is characteristic of T-DNA. The T-DNA may itself be a composite of segments derived from a plurality of sources, naturally occurring or synthetic. In addition, the T-DNA must contain at least one plant expressible promoter, 5' or "upstream" from the site of insertion of the insecticide structural gene, in sufficiently complete form to control initiation of transcription and initiation of translation of an inserted insecticide structural gene. This promoter may be derived from a T-DNA gene, a plant gene, or any other gene having a promoter that is functional within a plant cell in at least one tissue and at least one developmental stage. Preferably, an insertion site will be provided "downstream" in the direction of transcription and translation initiated by the promoter (3' to the promoter), so located with respect to the promoter to enable an insecticide structural gene inserted therein to be expressed under control of the promoter, either directly or as a fusion protein. The T-DNA may also include a 3'-untranslated region downstream from the site of insertion of the insecticide structural gene, which may function to regulate termination of transcription, polyadenylation, and post-transcriptional RNA processing. Optionally, a fusion protein may also be formed between the insecticide structural gene and the 3' end of the structural gene donating the 3'-untranslated region. The promoter and 3'-untranslated region elements may be derived from the same or different pre-existing genes, and may be derived from the same or different plant, T-DNA, or other sources. For example, an insecticide structural gene, as exemplified herein, could be nested between a plant gene promoter and 3' sequence from the same gene, or it could be a construct comprising the 3'-untranslated region of one gene and the promoter of another, derived from the same or different plant species of T-DNA. The coding region of a plant gene, as defined herein, may include a cDNA copy of the structural portion of a plant gene. The promoter and 3'-untranslated regions may also include modifications, either naturally or artificially induced, and may include chemically synthesized segments.

Plant promoter: As used herein includes regulatory elements of a plant gene and may further include structural elements of a plant gene, said elements being exogenous to the genes of T-DNA itself. These include, but are not limited to, promoters of the genes for phaseolin and the small subunit of ribulose-1,5-biphosphate carboxylase. Furthermore, a plant gene promoter is a region of the gene which provides for and may regulate the initiation of transcription and the initiation of translation. Additionally, the plant structural gene sequences (the region which codes for a protein in part or in whole and which may or may not contain one or more introns) may be introduced into T-DNA. (An intron is a region of a gene transcript which is post-transcriptionally removed before the mRNA is translated.) Expression under control of a plant promoter may take the form of direct expression in which the structural gene normally controlled by the promoter is removed in part or in whole and replaced by the inserted insecticide structural gene, a start codon being provided either as a remnant of the plant structural gene or as part of the inserted insecticide structural gene, or by fusion protein expression in which part or all of the insecticide structural gene is inserted in correct reading frame phase within the existing plant structural gene. In the latter case, the expression product is referred to as a fusion protein. The promoter segment may itself be a composite of segments derived from a plurality of sources, naturally occurring or synthetic. Sources of a plant promoter include, but are not limited to, plants listed in Table 2.

T-DNA promoter: Refers to any of the naturally occurring promoters commonly associated with T-DNA. These include, but are not limited to, promoters of the "1.6" transcript, octopine synthase gene (ocs), nopaline synthase gene (nos), tms, tml, and tmr genes, and may depend in part on the TIP source of the T-DNA. Expression under control of a T-DNA promoter may take the form of direct expression in which the structural gene normally controlled by the promoter is removed in part or in whole and replaced by the inserted insecticide structural gene, a start codon being provided either as a remnant of the T-DNA structural gene or as part of the inserted insecticide structural gene, or by fusion protein expression in which part or all of the plant structural gene is inserted in correct reading frame phase within the existing T-DNA structural gene. In the latter case, the expression product is referred to as a fusion protein. The promoter segment may itself be a composite of segments derived from a plurality of sources, naturally occurring or synthetic.

Plant expressible promoter: As used herein includes the definitions for T-DNA promoter and plant promoter, supra. However, an essential aspect of the promoter component of the present invention is that the insecticide structural gene be under control of a promoter expressible in a plant cell. Therefore, plant expressible promoter additionally refers to any promoter expressible in a plant cell which is expressed in at least one tissue during at least one developmental stage. Sources might include, but need not be limited to, plant viruses (e.g., the promoters of the 35S and 19S transcripts of cauliflower mosaic virus, CaMV), animal viruses, non-plant eukaryotes (e.g., animals, yeast), or plastids (e.g., a chloroplast or prokaryotic promoter if the insecticide gene is to be inserted into chloroplast DNA). Properties and components of a promoter that is derived from a source that is not a plant DNA or T-DNA (e.g., "TATA boxes," ATG translational start sites, intron splicing sites, etc.) are the same as described supra for T-DNA promoters, and plant promoters are also included within the present definition. The promoter segment may itself be a composite of segments derived from a plurality of sources, naturally occurring or synthetic.

Insecticide structural gene: As used herein includes that portion of an insecticide gene comprising a DNA segment coding for an insecticidal protein, polypeptide, or portion thereof, possibly including a translational start codon, but lacking other functional elements of a bacterial gene that regulate initiation of transcription and initiation of translation, commonly referred to as the promoter region. (Note that in the present invention such bacterial functional elements may be present after transfer of the insecticide structural gene into T-DNA. However, because they are not functional within a plant cell, such elements are not referred to by the term "insecticide structural gene.") An insecticide structural gene may be derived in whole or in part from plasmid DNA, genomic DNA, cDNA, and chemically synthesized DNA. It is further contemplated that an insecticide structural gene may contain one or more modifications in either the coding segments or untranslated regions which could affect the biological activity or chemical structure of the expression product, the rate of expression, or the manner of expression control. Such modifications could include, but are not limited to, mutations, insertions, deletions, substitutions, and "silent" modifications that do not alter the chemical structure of the expression product but which affect intercellular localization, transport, excretion, or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being insecticidal or being derived in part from an insecticidal protein.

Insecticidal protein: As used herein includes a bacterial protein toxic in any way to insects. This includes a protein or peptide that is directly or indirectly toxic or growth inhibitory under any circumstances to any insect. This also includes proteins that are toxic upon contact, ingestion, or respiration, where alone or in combination with other material, at any time within the life cycle of an insect, including egg, larva, pupa, nymph, and adult stages. This includes proteins toxic to insects, especially those of the families Lepidoptera and Diptera, and those of the genus *Ostrinia, Heliothis, Pectinophora*, and *Trichoplusia*, e.g., *M. sexta, O. nubilalis, H. zea, H. virescens, P. gossypiella*, and *T. ni*. Other taxa that might be chosen as targets include, but are not limited, those listed in Table 1. Examples of insecticidal proteins include, but are not limited to various varieties, listed in Table 3, of *Bacillus thuringiensis*, or in other species of *Bacillus*, e.g., *B. cereus, B. popilliae*, and *B. sphericus*. Genes that are used to construct or otherwise encode sequences encoding proteins toxic to insects include, but are not limited to, phospholipases, hyaluronidases, phosphatases, proteases, and the various crystal proteins of *B. thuringiensis*. The term crystal protein should be understood to refer to both the full-length protoxin and toxin forms, to toxic proteins related to the protein which is found in the crystalline inclusion bodies of *Bacillus thuringiensis*, and to artificial modifications of naturally occurring crystal proteins. Related proteins might be identified by nucleic acid or protein structural or sequence homology, immunological cross-reactivity, or cross-hybridization of nucleic acids.

Plant tissue: Includes differentiated and undifferentiated tissues of plants including, but not limited to, roots, shoots, pollen, seeds, tumor tissue, such as crown galls, and various forms of aggregations of plant cells in culture, such as embryos and calli. The plant tissue may be in planta or in organ, tissue, or cell culture, and may be derived from plants which include, but are not limited to, those listed in Table 2.

Plant cell: As used herein includes plant cells in planta and plant cells and protoplasts in culture, and may be derived from plants which include, but are not limited to, those listed in Table 2.

Production of a genetically modified plant expressing an insecticide structural gene introduced via T-DNA combines the specific teachings of the present disclosure with a variety of techniques and expedients known in the art. In most instances, alternative expedients exist for each stage of the overall process. The choice of expedients depends on variables such as the choice of the basic TIP or other vector systems for the introduction and stable maintenance of the expressible insecticide structural gene, the plant species to be modified and the desired regeneration strategy, and the particular insecticide structural gene to be used, all of which present alternative process steps which those of ordinary skill are able to select and use to achieve a desired result. For instance, although the starting point for obtaining an insecticide structural gene is exemplified in the present application by DNA isolated from *B. thuringiensis* var. *kurstaki* HD-73, DNA of other insecticidal protein gene-carrying bacterial strains or recombinant DNA molecules might be substituted as long as appropriate modifications are made to the gene isolation and manipulation procedures. As novel means are developed for the controlled expression and/or stable insertion of foreign genes in plant cells, those of ordinary skill in the art will be able to select among those alternate process steps to achieve a desired result. The fundamental aspects of the invention are the nature and structure of the insecticide structural gene and its means of insertion and expression in a plant genome. The remaining steps of the preferred embodiment for obtaining a genetically modified plant include inserting the promoter/insecticide structural gene combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

A principal feature of the present invention in its preferred embodiment is the construction of T-DNA having an inserted insecticide structural gene under control of a plant-expressible promoter or, most preferably, a T-DNA promoter, as these terms have been defined, supra. The insecticide structural gene must be inserted in correct position and orientation with respect to the desired promoter. Position has two aspects. The first relates to the side of the promoter on which the structural gene is inserted. It is known that the majority of promoters control initiation of transcription and translation in one direction only along the DNA. The region of DNA lying under promoter control is said to lie "downstream" or, alternatively, "behind" or "3' to" the promoter. Therefore, to be controlled by the promoter, the correct position of the plant structural gene insertion must be "downstream" from the promoter. (It is recognized that a few known promoters exert bi-directional control, in which case either side of the promoter could be considered to be "downstream" therefrom.) The second aspect of position refers to the distance, in base pairs, between known functional elements of the promoter, for example, the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the gene is similar to the distance between the promoter and the T-DNA gene it normally controls. Orientation refers to the directionality of the structural gene. That portion of a structural gene which ultimately codes for the amino terminus of the plant protein is termed the 5'-end of the structural gene, while that end which codes for the amino acid near the carboxyl end of the protein is termed the 3'-end of the structural gene. Correct orientation of the insecticide structural gene is with the 5'-end thereof proximal to the promoter. An additional requirement in the case of constructions leading to fusion protein expression is that the insertion of the insecticide structural gene into the promoter-donated structural gene sequence must be such that the coding sequences of the two genes are in the same reading frame phase, a structural requirement which is well understood in the art. An exception to this requirement, of relevance to the present invention, exists in the case where an intron separates coding sequences derived from an insecticidal protein gene from the first coding segment of the insecticide structural gene. In that case, the insecticide structural gene must be provided with a splice site compatible with the upstream splice junction contributed by the noninsecticidal coding sequences, and the intron splice sites must be so positioned that the correct reading frame for the promoter-donated structural gene and the insecticide structural gene are restored in phase after the intron is removed by post-transcriptional processing. Differences in rates of expression or developmental control may be observed when a given insecticide structural gene is inserted under control of different plant expressible promoters. Different properties including, but not limited to, such properties as stability, intercellular or intracellular localization or excretion, solubility, target specificity, and other functional properties of the expressed protein itself may be observed in the case of fusion proteins depending upon the insertion site, the length and properties of the segment of T-DNA protein included within the fusion protein and mutual interactions between the components of the fusion protein that effect folded configuration thereof, all of which present numerous opportunities to manipulate and control the functional properties of the insecticidal protein product, depending upon the desired physiological properties within the plant cell, plant tissue, and whole plant.

Location of the promoter/insecticide structural gene combination insertion site is not critical as long as the transfer function sequences immediately surrounding the T-DNA borders are not disrupted, since these regions appear from prior art studies to be essential for insertion of the modified T-DNA into the plant genome. Preferred insertion sites are those which lie in areas that are most actively transcribed, in particular the tml gene and an area designated "1.6" lying in the HindIII-f fragment, and equivalent to transcript 24, as shown in FIG. 2. The term "1.6" is used herein to designate this actively transcribed region of T-DNA. The T-DNA into which the promoter/insecticide gene combination is inserted, is obtained from any of the TIP plasmids. The insecticide gene is inserted by standard techniques well known to those skilled in the art. The orientation of the inserted plant gene, with respect to the direction of transcription and translation of endogenous T-DNA genes is not critical; either of the two possible orientations is functional. Differences in rate of expression may be observed when a given gene is inserted at different locations within T-DNA, possibly because of such factors as DNA methylation chromatin structure. Readily detectable levels of expression of a plant promoter from the phaseolin gene have been obtained where that gene was inserted into pTi15955, an octopine-type plasmid of *A. tumefaciens* at a SmaI site found within the tml gene or a HpaI site found within tmr.

A convenient means for inserting a promoter/insecticide structural gene combination into T-DNA involves the use of a shuttle vector, as described supra, having segments of T-DNA (those segments between which insertion is desired) incorporated into a plasmid capable of replicating in *E. coli*. The T-DNA segment contains a restriction site, preferably one which is unique within the shuttle vector. The insecticide structural gene can be inserted at the unique site in the T-DNA sequences, and the shuttle vector is transferred into cells of the appropriate *Agrobacterium* strain, preferably one whose T-DNA is homologous with the T-DNA segments of the shuttle vector. The transformed *Agrobacterium* strain is preferably grown under conditions which permit selection of a double-homologous recombination event which results in replacement of a pre-existing segment of the Ti plasmid with a segment of T-DNA of the shuttle vector. However, it should be noted that the present invention is not limited to the introduction of the promoter/insecticide structural gene combination into T-DNA by a double homologous recombinant mechanism; a homologous recombination event with a shuttle vector (perhaps having only a single continuous region of homology with the T-DNA) at a single site or an insertion of a promoter/gene-carrying bacterial transposon will also prove an effective means for inserting that combination into T-DNA.

Following the strategy just described, the modified T-DNA can be transferred to plant cells by any technique known in the art. For example, this transfer is most conveniently accomplished either by direct infection of plants with the novel strain containing an insecticide gene incorporated within T-DNA, or by co-cultivation of the *Agrobacterium* strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of co-cultivation, a certain proportion of the plant cells are transformed, that is to say, have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the insecticide structural gene. Examples include either dihydrofolate reductase or neomycin phosphotransferase expressed under control of a nopaline synthase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthase. Screening methods well known to those skilled in the art include assays for opine production, specific hybridization to characteristic RNA or T-DNA sequences, or immunological assays for specific proteins, including ELISAs, radioimmune assays and "Western" blots. Additionally, the toxic properties of expressed insecticidal protein can be used to identify transformed tissue.

An alternative to the shuttle vector strategy involves the use of plasmids comprising T-DNA or modified T-DNA, into which an insecticide structural gene is inserted, said plasmids being capable of independent replication in an *Agrobacterium* strain. Recent evidence reviewed in the Background indicates that the T-DNA of such plasmids can be transferred from an *Agrobacterium* strain to a plant cell, provide the *Agrobacterium* strain contains certain transacting genes whose function is to promote the transfer of T-DNA to a plant cell. Plasmids that contain T-DNA and are able to replicate independently in an *Agrobacterium* strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but the minimum amount of DNA surrounding the T-DNA border is deleted, the remaining portions being the minimum necessary to be transferable and integratable in the host cell. Such plasmids are termed "micro-TIP." Sub-TIP plasmids are advantageous in that they are small and relatively easy to manipulate directly, eliminating the need to transfer the gene to T-DNA from a shuttle vector by homologous recombination. After the desired structural gene has been inserted, they can easily be introduced directly into a plant cell containing the trans-acting genes that promote T-DNA transfer. Introduction into an *Agrobacterium* strain is conveniently accomplished either by transformation of the *Agrobacterium* strain or by conjugal transfer from a donor bacterial cell, the techniques for which are well-known to those of ordinary skill. For purposes of introduction of novel DNA sequences into a plant genome, TIP plasmids and sub-TIP plasmids should be considered functionally equivalent.

Although the preferred embodiment of this invention incorporates a T-DNA-based *Agrobacterium*-mediated system for incorporation of the insecticide gene into the genome of the plant which is to be made insect resistant, other means for transferring and incorporating the gene are also included within the scope of this invention. Other means for the stable incorporation of the insecticide gene into a plant genome additionally include, but are not limited to, use of vectors based on viral genomes, minichromosomes, transposons, and homologous or non-homologous recombination into plant chromosomes. Alternate forms of delivery of these vectors into a plant cell additionally include, but are not limited to, direct uptake of nucleic acid, fusion with vector-containing liposomes, microinjection, and encapsidation in viral coat protein followed by an infection-like process. Systems based on *Agrobacterium* cells and TIPs can be used to transform dicots and gymnosperms by transfer of DNA from a bacterium to a plant cell; systems based on alternate vectors or means for vector delivery may be used to transform all gymnosperms and all angiosperms, including both monocots and dicots.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto, and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. Inactivation of these genes returns the hormone balance in the transformed tissue toward normal and greatly expands the ease and manipulation of the tissue's hormone levels in culture, leading to a plant that is readily regenerated because of its more normal hormone physiology. It is important to note that if the mutations in tmr and tms are introduced into T-DNA by double homologous recombination with a shuttle vector, the incorporation of the mutations must be selected in a different manner than the incorporation of the promoter/insecticide structural gene. For example, in the former instance one might select for chloramphenicol resistance while the latter selection might be for resistance to kanamycin. The inactivation of the tms and tmr loci may be accomplished by an insertion, deletion, or substitution of one or more nucleotides within the coding regions or promoters of these genes, the mutation being designed to inactivate the promoter or disrupt the structure of the protein. (The construction of suitable mutations has been exemplified by Hall, T. C. et al., U.S. patent application Ser. Nos. 06/485,613 and 06/485,614.) In some instances, tumor cells are able to regenerate shoots which carry integrated T-DNA and express T-DNA genes, such as nopaline synthase, and which also express an inserted insecticide structural gene.

The shoots can be maintained vegetatively by grafting to rooted plants and can develop fertile flowers. The shoots thus serve as parental plant material for normal progeny plants carrying T-DNA and expressing the insecticide structural gene inserted therein.

The genotype of the plant tissue transformed is often chosen for the ease with which its cells can be grown and regenerated in in vitro culture. Should a cultivar of agronomic interest be unsuitable for these manipulations, a more amenable variety is first transformed. After regeneration, the newly introduced foreign insecticidal protein gene is readily transferred to the desired agronomic cultivar by techniques well-known to those skilled in the art of plant breeding and plant genetics. Sexual crosses of transformed plants with the agronomic cultivars yielded initial hybrids. These hybrids can then be backcrossed with plants of the desired genetic background. Progeny are continuously screened and selected for the continued presence of integrated T-DNA or for the new phenotype resulting from expression of the inserted insecticidal protein gene. In this manner, after a number of rounds of backcrossing and selection, plants can be produced having a genotype essentially identical to the agronomically desired parents with the addition of the inserted insecticidal protein gene.

In an alternative method for conferring insect resistance to a crop, one may infect plants within a field which is to be protected with an *Agrobacterium* cell harboring a TIP plasmid having undisabled T-DNA which carries an expressible insecticidal protein gene. We have found that larvae will feed on crown gall tissue. When insect larvae infesting the field eat transformed tissue containing an insecticide gene, they will be affected by the insecticidal protein within that tissue. The *Agrobacterium* and TIP might additionally encode genes for insect attractants. The presence of such attractants in transformed tissue will increase the insects' preference for such tissue as a food source relative to the rest of the crop material in the field.

EXAMPLES

The following Examples utilize many techniques well known and accessible to those skilled in the arts of molecular biology and manipulation of TIPs and *Agrobacterium*; such methods are fully described in one or more of the cited references if not described in detail herein. Enzymes are obtained from commercial sources and are used according to the vendor's recommendations or other variations known to the art. Reagents, buffers, and culture conditions are also known to those in the art. Reference works containing such standard techniques include the following: Wu, R. (ed.) (1979) *Methods Enzymol.* 68; Wu, R. et al. (eds.) (1983) *Methods Enzymol.* 100 and 101; Grossman, L., K. Moldave (eds.) (1980) *Methods Enymol.* 65; Miller, J. H. (1972) *Experiments in Molecular Genetics*; Davis, R. et al. (1980) *Advanced Bacterial Genetics*; Schleif, R. F., P. C. Wensink (1982) *Practical Methods in Molecular Biology*; and Maniatis, T. et al. (1982) *Molecular Cloning*. Additionally, Lathe, R. F. et al. (1983) *Genet. Eng.* 4:1-56, make useful comments on DNA manipulations.

Textual use of the name of the name of a restriction endonuclease in isolation, e.g., "BclI," refers to use of that enzyme in an enzymatic digestion, except in a diagram where it can refer to the site of a sequence susceptible to action of that enzyme, e.g., a restriction site. In the text, restriction sites are indicated by the additional use of the word "site," e.g., "BclI site." The additional use of the word "fragment," e.g., "BclI fragment," indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "blunt" or "sticky" (i.e., having a single-stranded protuberance capable of base-pairing with a complementary single-stranded oligonucleotide) and that the sequence of a sticky-end will be determined by the specificity of the enzyme which produces it.

In these Examples, special symbols are used to make sequences more easily understood. Sequences that code for proteins are underlined, and codons are separated with slashes (/). The positions of cuts or gaps in each strand caused by restriction endonucleases or otherwise are indicated by the placement of asterisks (*).

Plasmids, and only plasmids, are prefaced with a "p," e.g., pTi15955 or pKS-4, and strains parenthetically indicate a plasmid harbored within, e.g., *A. tumefaciens* (pTi15955) or K802(pKS-4). Table 4 provides an index useful for identifying plasmids and their interrelationships. Table 5 provides a list of deposited strains.

Example 1

The first step in developing an insect-resistant crop was to clone the insecticidal protein gene of *B. thuringiensis* var. *kurstaki* HD-73, which is on deposit with the Agricultural Research Culture Collection, Northern Regional Research Laboratory, Peoria, Ill., and has NRRL number B-4488.

1.1 Cloning the *Bacillus thuringiensis* insecticidal protein gene. The 50 megadalton (MD) plasmid was enriched from HD-73 using sucrose gradient centrifugation. An HD-73 library was constructed by first digesting this plasmid with HindIII. The resulting fragments were mixed with and ligated to HindIII-linearized pRB322 (Bolivar, F. et al. [1978] *Gene* 2:95-113) and transformed into *E. coli* HB101. Ampicillin-resistant tetracycline-sensitive transformants were screened by digesting isolated plasmid DNA with HindIII and choosing those clones with 6.6 kilobase pair (kbp) inserts. Colonies containing plasmids p123/58-3 and p123/58-10 were selected from the HD-73 library for further analysis using an insect bioassay (see Example 8). These clones were grown in L-broth and a 250-fold concentrated cell suspension was sonicated and the extract applied to the surface of insect diet. Neonatal *Manduca sexta* (tobacco hornworm) larvae were placed on the diet for one week. Insect larvae fed extracts of strains harboring p123/58-3 or p123/58-10 did not grow, and all larvae died in 2 to 5 days. There was no apparent difference between the larvae fed these extracts and those fed insecticidal protein purified from cells of *B. thuringiensis.*

Restriction enzyme analysis of p123/58-3 and p123/58-10 showed that the two plasmids were identical except for having the 6.6 kbp *B. thuringiensis* DNA fragment inserted into the pBR322 vector in opposite orientations. Note that either of these two plasmids can be converted to the other by digestion with HindIII, religation, and transformation into HB101 followed by appropriate selection and screening steps.

p123/58-10 was used to further probe the transformants from the HD-73 plasmid library. Sixteen of the 572 colonies hybridized to the insert of clone p123/58-10 and all had the characteristic 6.6 kbp HindIII fragment. Further restriction enzyme analysis showed these clones to all be one of the two possible orientations in pBR322 of the same DNA fragment.

This suggested there could be a single crystal protein gene in strain HD-73. That these clones represent the only insecticidal protein gene in HD-73 was confirmed by hybridizing labeled p123/58-10 probe to Southern blots of HD-73 plasmid DNA digested with HindIII, BglIII, or SalI. None of these enzymes has a restriction site in our cloned crystal protein gene. Hybridization results showed a single band of B. thuringiensis cellular DNA hybridized with p123/58-10 and further indicated that HD-73 has a single insecticidal crystal protein gene. We have identified a number of other clones by hybridization with a probe made from p123/58-10. Restriction mapping has shown that these clones are all identical to either p123/58-3 or p123/58-10, further supporting the conclusion that the HD-73 has a single crystal protein gene.

1.2 Immunological analysis. Analyses on the protein produced in the E. coli clones shows that p123/58-3 and p123/58-10 encoded protein that formed a precipitin band with antiserum to B. thuringiensis insecticidal protein in Ouchterlony diffusion slides. Cell extracts were analyzed on 10% sodium docecyl sulfate (SDS) polyacrylamide gels, transferred to nitrocellulose, and immunological reactions were done with antibody and $^{125}$I-protein A (Western blots, Example 7). No band was found at 130 kD (kilodalton) where denatured protoxin is observed; however, a peptide of about 67 kD was seen that binds crystal protein antibody (Western blots as done in Example 7), and was identical in size to activated toxin. This peptide accounted for approximately 1% of the total E. coli protein.

1.3 Sequence analysis. We compared our DNA sequence results (FIG. 1), obtained by methods well known to those skilled in the art of DNA sequencing (e.g., see Maxam, A. M., W. Gilbert [1980] *Methods Enyzmol.* 65:499-560), with published sequences (see Background). The published sequences showed only partial homology with our own sequence. An open reading frame of about 2.8 kbp was observed which bounded at the 5'-end by a translational start signal (ATG) and did not stop before encountering the HindIII site at the junction between the B. thuringiensis DNA and the pBR322 vector. The size of the protein encoded by this open reading frame from the ATG to the HindIII site is greater than that of the 67 kD protein that we observed to be translated in E. coli cells but less than what is needed to encode the 130 kD native crystal protein. That the exact means of translational termination in the pBR322 encoded read-through peptide was not important was suggested by the finding that insecticidal activity was encoded by B. thuringiensis DNA inserts having either orientation within the pBR322 vector. Presumably the initially translated amino acid residues carboxy-terminal to the ultimate carboxy-terminus of the translated polypeptide were removed in E. coli by a proteolytic process similar to that which naturally activates the crystal protein.

Example 2

This example teaches the insertion of the *Bacillus thuringiensis* insecticide gene between a T-DNA gene promoter and a polyadenylation (poly(A) addition) signal, the transfer of the insecticide gene to various plant species via a Ti plasmid, and the regeneration of plants expressing this gene under control of the T-DNA promoter. A large part of the strategy used in this construction is diagrammed in FIG. 3, which represents plasmids schematically and is not necessarily drawn to scale.

2.1 Introduction of BamHI site into the insecticidal protein gene. A BamHI site is introduced into the insecticidal protein gene of p123/58-10 at a location just 5' to the start of the coding sequence. The wild-type base sequence (b) and the changed bases in an oligonucleotide primer (a) are as follow:

```
                      BamHI
(a) 5'    AGATGGAG*GATCCTT ATG GAT AAC AAT 3'

(b) . . . AGATGGAG GTAACTT/ATG/GAT/AAC/. . .
                           Met Asp Asn Asn
```

The changed bases are the underlined ATC sequence in (a). Note that good hybridization properties are insured because only three out of 27 base pairs are changed.

p123/58-10 is digested with HindIII and is mixed with and ligated to HindIII-linearized mWB2344 RF (replicative form) DNA. The mixture is transformed into JM103, and transformed colonies are screened by plasmid isolation followed by restriction analysis for the presence of insertion of a single copy of the insecticidal protein gene-bearing fragment. Vectors containing the two possible orientations are labeled M13-Bt-A and M13-Bt-S. They have the antisense and sense strands, respectively, of the insecticide structural gene when in viral form. M13-Bt-A is hybridized with the oligonucleotide primer, 5'-AGATGGAGGATCCT-TATGGA TAACAAT-3', previously synthesized as described in Example 10.1. The oligonucleotide: M13-Bt-A hybrid is incubated with the Klenow fragment of E. coli DNA polymerase I, covalently closed circular DNA (cccDNA) is enriched, and the mixture is transformed into JM103. The virions produced by transformants are isolated and used to infect cells at a low multiplicity of infection. RF DNA is isolated from a number of the infected colonies and is characterized by restriction mapping. Clones derived from the mutant oligonucleotide-primed strand are identified by the presence of a novel BamHI site at the 5'-end of the insecticide structural gene, and one such vector is designated M13-Bt-A(Bam).

M13-Bt-A(Bam) RF DNA is digested with BamHI and HindIII, and is mixed with and ligated to a linker, synthesized as described in Example, 10.1, having the following structure:

```
         HindIII          BamHI
       5'AGCTAGCTGACTAG3'

3'TCGACTGATCCTAG5'
```

Note that this linker contains translational stop signals (underlined) in all three possible reading-phases. The linkers are trimmed by digestion with BamHI and an insecticide structural gene-bearing DNA fragment is purified by agarose gel electrophoresis.

2.2 Construction and modification of a promoter vehicle. The T-DNA "1.6" gene is summarized as follows:

```
            ClaI              960 bp  250 bp  ClaI  60 bp   50 bp
    5'...TACACCAAAT*CG/ATG/GAC/ATG/.../TGA/....AT*CGAT....AAATAA...AAATAA...3'
          promoter          Met Asp Met ....stop      polyadenylaction signals
```

By removing the ClaI fragment, the promoter region of the "1.6" gene can be brought next to the 3'-downstream region of the gene. This 3' region includes polyadenylation signals. The resulting structure is summarized as follows:

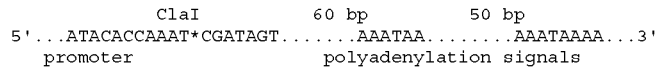
```
          ClaI          60 bp        50 bp
5'...ATACACCAAAT*CGATAGT.......AAATAA........AAATAAAA...3'
   promoter                  polyadenylation signals
``` pKS111, which is a pRK290 clone corresponding to the T-DNA clone p403 (which encodes the "1.6" gene which was described in the Detailed Description, transcript 24 in FIG. 2, see also Fink, C. F. [1982] M. S. thesis, University of Wisconsin-Madison), is digested with ClaI and then religated. The ligation mix is transformed into *E. coli* K802 (Wood, W. B. [1966] *J. Mol. Biol.* 16:118) and selected for tetracycline resistance. Plasmids are isolated by doing "minipreps" (plasmid preparations from small volume cell cultures), and restriction maps are obtained to prove the structure. The new vehicle, pKS-proI (see Hall, T. C. et al., U.S. application Ser. No. 06/485,614), can be linearized by ClaI.

pKS-proI grown in K802 was cut with ClaI. After converting sticky-ends to blunt-end with the Klenow fragment of *E. coli* DNA polymerase I, the DNA was mixed with and ligated to a BamHI linker. The resulting mixture was digested with ClaI to remove religated pKS-proI, and transformed into K802. Plasmids from tetracycline-resistant transformants are screened by restriction analysis, and a plasmid having the ClaI site at the ATG translational start replaced with a BamHI site is designated pKS-proI(Bam).

2.3 Introduction of a kanamycin resistance gene into pKS-proI(Bam). It is advantageous to have a kanamycin resistance (kan) resistance gene inserted next to the promoter/insecticide gene combination so as to allow selection of double homologous recombinants after a triparental mating. The source of kan was pKS-4 (Example 2.5). In pKS-4 the kan gene is flanked on one side by a ClaI site. In order to remove a kan gene-bearing fragment from pKS-4 with ClaI (i.e., on a ClaI/kan" fragment) it is necessary to introduce a ClaI site into that plasmid on the opposite side of kan from the existing ClaI site. This is accomplished by converting a conveniently positioned BamHI site (5' . . . G*GATCC . . . 3') to the specificity of ClaI (5' . . . AT*CGAT . . . 3').

pKS-4 is linearized by digestion with BamHI, thereby generating sticky-ends having the following structures:

```
     5'...G              GATCC...3'
     3'...CCTAG               C...5'
```

The recessed ends of this structure are filled in by incubation with the Klenow fragment of *E. coli* DNA polymerase I, forming the following blunt-ends:

```
     ...GGATC             GATCC...
     ...CCTAG             CTAGG...
```

When these ends were blunt and ligated together, the resulting suture has the following sequence:

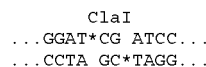
```
              ClaI
        ...GGAT*CG ATCC...
        ...CCTA GC*TAGG...
```

Note that the resulting structure is susceptible to the action of ClaI but not to that of BamHI.

Alternatively to the above construction, one may convert the BamHI site, or another conveniently located restriction site, into a ClaI site by use of the appropriate linkers. pKS-4 was digested with SmaI mixed with and ligated to ClaI/ blunt-ended linkers having the sequence 5'-CATCGATG-3', digested with ClaI, religated, and transformed into K802. Plasmids isolated from transformants resistant to kanamycin were screened for presence of a novel ClaI site in the position formally occupied by a SmaI site. A ClaI/kan fragment can be isolated from such a plasmid. The plasmid is designated pKS4.2.

Figure 3:
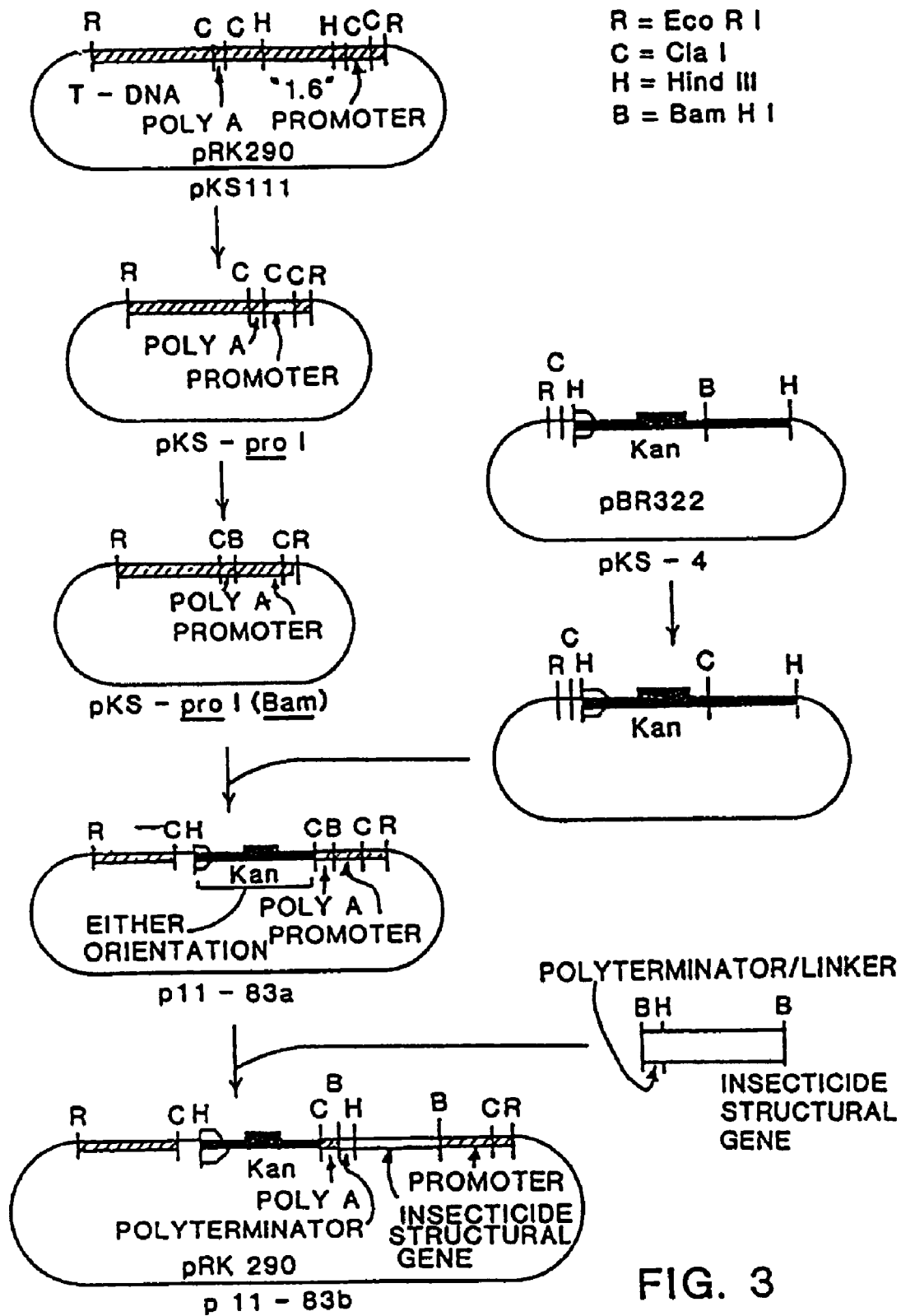
FIG. 3 is a diagram of a construction described in Example 2 of a recombinant DNA vector carrying an insecticidal structural gene under control of a plant expressible promoter.

When grown in *E. coli* K802, pKS-proI(Bam) is methylated at two remaining ClaI sites: one is about 145 bases from the promoter-polyadenylation junction (this is about 30 bases past the second polyadenylation site); the other is about 200 bases from the right hand p403 EcoRI site (see FIG. 2). Methylation blocks cutting by the ClaI restriction endonuclease at an otherwise susceptible site. Therefore, these methylations protect these sites and effectively direct action of the ClaI enzyme to other sites. pKS-proI(Bam) is transferred to and grown in *E. coli* GM33, a strain that does not methylate adenosine residues in DNA, so that the otherwise methylated ClaI sites can be cut. After purification of that plasmid from GM33 (pKS-proI(Bam)), a partial digestion is done with ClaI and the resulting mixture is ligated with the ClaI/kan fragment described above. After transformation into *E. coli* K802, transformants are selected on tetracycline and kanamycin containing media. After plasmid isolation and restriction mapping, a clone having the desired construction is identified, and the plasmid found in this clone is labeled p11-83a (FIG. 3).

p11-83a has a kan gene-bearing fragment ligated into the "middle" ClaI site about 30 bp past the second polyadenylation site. The BamHI fragment of the insecticide gene, isolated from the modified vector constructed in Example 2.1, is now ligated into the BamHI site of BamHI-linearized p11-83a that has been transferred to and grown in K802 and is methylated. After transformation into K802, tetracycline and kanamycin selection, plasmid isolation, and restriction enzyme mapping, the desired construction having the insecticide structural gene inserted between the pTi15955 "1.6" promoter and polyadenylation site is identified, and the plasmid harbored therein is labeled p11-83b (FIG. 3).

2.4 Introduction of p11-83b into Ti plasmids. p11-83b is introduced into pTi15955, pTiA66 (equivalent to pTi15955 but having a nonfunctional tms gene), and mutants deleted in genes affecting regeneration by homologous recombination (Example 10). Tobacco plants are transformed by a system described in Example 6, and transformants are identified by Southern and Northern blots (techniques well known to those skilled in the art) with appropriate probes and by the presence of octopine and crystal protein. Transformed tobacco tissue is lethal to tobacco hornworms. Tobacco plants are regenerated from transformed cells, as described in Example 6, and entered into breeding programs. Fields of regenerated plants and their insecticidal protein-containing descendants are resistant to infestation by larvae of insects such as tobacco hornworm by virtue of the toxic effect such larvae experience when eating tissue from such plants.

2.5 Cloning and isolation of a kanamycin resistance gene. pRZ102 (Jorgenson, R. A. et al. [1979] *Mol. Gen. Genet.* 177:65-72), a ColE1 plasmid carrying a copy of the transposon Tn5, was digested with BamHI and HindIII, mixed with pBR322 previously linearized with the same two enzymes, ligated, and transformed into K802. Plasmids isolated from transformants selected for resistance to both ampicillin and kanamycin were restriction mapped, and one having the structure shown in FIG. 3 was labeled pKS-4. pKS-4 DNA may be isolated from *E. coli* C600 (pKS-4), which has been deposited as NRRL B-15394.

Example 3

This example teaches another method of inserting an expressible gene for the *B. thuringiensis* insecticidal protein into a plant genome. The shuttle vector is similar to that used by Fink, C. L. (1982) M. S. thesis, University of Wisconsin-Madison, to put the nos gene into an octopine Ti plasmid. In the present invention, the protein coding sequences for nos are removed and replaced with an insecticidal gene before insertion into the Ti plasmid. The eventual result is an octopine-type Ti plasmid carrying an insecticide gene expressible in plant cells under control of a nopaline synthase promoter.

3.1 Moving the nos gene into M13mp7. pCF44 (Fink, supra) was digested with XhoI, religated to itself, and transformed back into K802. Plasmid DNA isolated from ampicillin-resistant transformants was analyzed with restriction enzymes. A plasmid having a single XhoI site within its Ti plasmid-derived DNA sequences was designated pCF44A. The single XhoI site was the result of the deletion of a DNA fragment between the two pCF44XhoI sites. Deletion of this XhoI fragment resulted in the complete removal of two inconvenient ClaI sites.

pCF44 DNA was digested with HindIII and BamHI, mixed with and ligated to a double-stranded circular replicative form (RF) of the single-stranded DNA vector M13mp7 which had been linearized with BamHI. After transformation of the mixture into JM103 and selection of white plaques, two colonies were identified by restriction mapping after RF isolation, designated M13-1 and M13-3, contained the sense and antisense strands, respectively, when in single-stranded form.

3.2 Placement of an NcoI site behind the nos promoter. An oligonucleotide primer having the sequence 5'-AGTCT-CATAC TCACTCTCAA TCCAAATAAT CTGCCATGGA T-3' was synthesized as described in Example 10.1. This oligonucleotide was changed at the underlined base from the naturally occurring sequence at the 5'-end of the nos structural gene. The change resulted in the introduction of an NcoI site, 5' . . . C*CATGG . . . 3', at the ATG translational start of the nos gene. The oligonucleotide was hybridized to circular single-stranded M13-3 DNA isolated from virions which had been sedimented out of culture medium. The oligonucleotide:M13-3 hybrid was incubated with DNA ligase and the Klenow fragment of *E. coli* DNA polymerase I, covalently closed circular DNA (cccDNA) was enriched, and the mixture was transformed into JM103. The virions produced by transformants were isolated and used to infect cells at a low multiplicity of infection. RF DNA was isolated from a number of these infected colonies and characterized by restriction mapping. Clones derived from the mutant oligonucleotide-primed strand were identified by the presence of a single NcoI site, which allowed them to be linearized by that enzyme. The mutated clones were further characterized to localize the NcoI site by digestion with ClaI, BamHI (to identify linearized molecules), and ClaI together with NcoI. The mutated M13-3 vector was labeled M13-3A/B18a.

3.3 Moving the insecticide gene into M13mp8. p123/58-10 DNA (Example 1.1) was digested with EcoRI and mixed with and ligated to EcoRI-linearized M13mp8 RF DNA. After transformation of the mixture into JM103 and selection of white plaques, two colonies having the insecticide gene-carrying fragment inserted in opposite orientations were identified by restriction mapping. They were labeled MBT14 and MBT3 and respectively had the sense and antisense strands when in single-stranded form.

3.4 Placement of an NcoI site at the insecticide gene translation start. An oligonucleotide primer having the sequence 5'-GAGGTAACCC ATGGATAACA AT-3' is synthesized as described in Example 10.1. This oligonucleotide is changed at the two underlined bases from the naturally occurring sequence at the 5'-end of the insecticide structural gene. The change results in the introduction of an NcoI site, 5' . . . C*CATGG . . . 3', at the ATG translational start of the insecticide gene. The oligonucleotide is hybridized to circular single-stranded MBT3 DNA isolated from virions which had been sedimented out of culture medium. The oligonucleotide:MBT3 hybrid is incubated with DNA ligase and the Klenow fragment of *E. coli* DNA polymerase II, cccDNA is enriched, and the mixture is transformed into JM103. The virions produced by the transformants are isolated and used to infect cells at a low multiplicity of infection. RF DNA is isolated from a number of these infected colonies and characterized by restriction mapping. Clones derived from the mutant oligonucleotide-primed strand are identified by the presence of a single NcoI site which allows them to be linearized by that enzyme. The mutated clone is further characterized by restriction enzyme analysis, and the presence of the mutant sequence is confirmed by sequencing. The plasmid having the desired sequence is labeled MBT3(Nco).

3.5 Assembly of a plant expressible insecticide gene in a shuttle vector. NcoI- and HindIII-digested MBT3(Nco) RF DNA is mixed with and ligated to a linker, synthesized as described in Example 11.1, having the following structure:

```
      HindIII-end       BamHI
    5'AGCTGACTAACTAG3'
       3'CTGATTGATCCTAG5'
```

This linker encodes stop codons (underlined) in all three reading phases, and is ended by a functional BamHI site and a HindIII compatible sticky-end incapable of reconstructing a HindIII site. The insecticide gene-bearing DNA fragment is then trimmed by digestion with NcoI and BamHI and is isolated by an agarose gel electrophoresis.

pKS111-N (Fink, supra) is a plasmid having a nos gene inserted in Tn5 DNA (from pKS-4) which has a functional kan gene, which is itself inserted in the T-DNA of pKS111. pKS111-N is linearized with SstII and digested to completion with BamHI. M13-3A/B18a is digested with NcoI and SstII and the SstII/NcoI promoter fragment is isolated by agarose gel electrophoresis. The SstII/NcoI promoter and NcoI/BamHI gene fragments are mixed with and ligated to the pKS111-N SstII/BamHI reaction products. The ligation mixture is then transformed into *E. coli* K802. Plasmids isolated from transformants resistant to kanamycin and tetracycline are subjected to restriction enzyme analysis, and colonies harboring plasmids identical to pKS111-N, except for replacement of a 5'-portion of the nos gene with an insecticide structural gene, are identified. Such a plasmid is designated pKS111-NpBt.

3.6 Insertion into TIP plasmids, plant infection, and regeneration. *E. coli* K802(pKS111-NpBt) is mated with *A. tumefaciens* as described in Example 9. The *Agrobacterium* strains chose harbor TIP plasmids, based on pTi15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the *Agrobacterium* strains are used to infect tobacco cells which are then regenerated. The resulting plants are used as breeding stock to be crossed with various commercial varieties for which insect resistance properties are desired. Regenerated plants and fields of their insecticidal protein-containing descendants are resistant to infestation by larvae of insects such as tobacco hornworm by virtue of the toxic effect such larvae experience when eating tissue from such plants.

Example 4

This example teaches another method of inserting an expressible gene for the *B. thuringiensis* insecticidal protein into a plant genome. The strategy is similar to that described in Example 3 but differs in that a plant promoter is used instead of a T-DNA promoter. The plant gene providing the promoter is phaseolin, which has been shown to be active in species other than its source, the bean *Phaseolus vulgaris* L.

4.1 Moving the phaseolin gene into M13mp7. BamHI linkers, having the sequence 5'-GGATCC-3', are annealed to form double-stranded structures and blunt-end ligated to form concatamers. These concatamers are partially digested with BamHI to expose 5'GATC . . . 3' sticky-ends, which are compatible with sticky-ends generated by the enzymes BamHI, BclI, MboI, Sau3AI, and XhoII (5'GATC . . . 3'). A Charon 24A phage clone of phaseolin, 177.4 (Sun, S. M. et al. [1981] *Nature* 289:37-41; Slightom, J. L. et al. [1983] *Proc. Natl. Acad. Sci. USA* 80:1897-1901, also designated AG-PVPh177.4) is digested with BglII and BamHI, mixed with and ligated to the concatenated linkers, and completely digested with BamHI to trim the linkers and expose the BamHI sticky-ends; a 3.8 kbp fragment containing the phaseolin gene and 5'- and 3"-flanking sequences is isolated by agarose gel electrophoresis followed by elution. This fragment has BamHI sites at either end as the BamHI/BglII linkage site is not susceptible to the action of either enzyme. The 3.8 kbp BglII/BamHI fragment can also be obtained from p8.8, a pBR322-based subclone of 177.4.

The 3.8 kbp fragment is mixed with and ligated to BamHI-linearized M13mp7 RF. After transformation of the mixture into JM103 and selection of white plaques, two colonies are selected after characterization by restriction and hybridization analysis of RFs and phage DNA. The viral forms of M13-3.8A and M13-3.8S are respectively found to be carrying the antisense and sense strands of the phaseolin gene.

4.2 Placement of an NcoI site behind the phaseolin promoter. The *Phaseolus* DNA of M13-3.8A has an NcoI site about 450 bp upstream from the phaseolin transcriptional start. The presence of this site will be inconvenient when one wishes to cleave the plasmid at the NcoI site to the introduced at the phaseolin translational start. Isolated M13-3.8A RF DNA is linearized with NcoI, and the 5'-protruding ends are filled in by the action of the Klenow fragment of *E. coli* DNA polymerase I. After blunt-end ligation and transformation into JM103, RF DNAs are isolated and characterized by restriction mapping. A colony is chosen which harbors a vector, labeled M13-3.8Ac, which is lacking the NcoI site of the *Phaseolus* DNA but is otherwise unchanged from M13-3.8A.

An oligonucleotide primer having the sequence 5'-ATACTACTCT ACCATGGTGA GAGCAAGGG-3' is synthesized as described in Example 10.1. This oligonucleotide is changed at the underlined bases from the naturally occurring sequence at the 5'-end of the phaseolin gene. The oligonucleotide is hybridized to circular single-stranded M13-3.8Ac DNA isolated from virions which had been sedimented out of culture medium. The oligonucleotide:M13-3.8Ac hybrid is incubated with DNA ligase and the Klenow fragment of *E. coli* DNA polymerase I, cccDNA is enriched, and the mixture is transformed into JM103. The virions produced by transformants are isolated and used to infect cells at a low multiplicity of infection. RF DNA is isolated from a number of these infected colonies and characterized by restriction mapping. Clones derived from the mutant oligonucleotide-primed strand are identified by the presence of a novel NcoI site positioned at the 5'-end of the coding sequence. The mutated clones are further characterized to localize the NcoI site by digestion with ClaI and ClaI together with NcoI. The mutated M13-3.8Ac vector is labeled M13-3.8Aa.

4.3 Placement of a Hind III site at the 3'-end of the phaseolin gene. To conveniently introduce the insecticide gene into the phaseolin gene, two additional changes must be made to that phaseolin gene. The first change involves addition of HindIII site (5' . . . A*AGCTT . . . 3') 5' to the polyadenylation site and near the 3'-end of the phaseolin gene. The other important change involves placing translational stop codons (e.g., TAA, TAG, or TGA, underlined below) in all three reading frames. When the oligonucleotide 5'-AGGGTGCATT TGAAGCTTGA ATAAGTAAGA ACTAAAATGC-3' (a) is compared with the 3'-end of the phaseolin gene coding sequence (b), it can be seen to have the desired properties as follows:

```
                       HindIII
(a) 5'AGGGTGCATTTGA*AGCTTGAATAAGTAAGAACTAAAATGC3'
(b) ..AGGGTGCATTTGT GTACTGAATAAGTATGAACTAAAATGC..
mismatches:            ↑ ↑↑↑↑          ↑
```

Note also that this 38-mer has only 6 mismatches, thus insuring good hybridization properties during priming.

The oligonucleotide 5'-AGGGTGCATT TGAAGCTTGA ATAAGTAAGA ACTAAAATGC-3', synthesized as described in Example 10.1, is hybridized to single-strand circular M13-3.8Aa DNA purified from virions isolated by centrifugation of culture medium. The oligonucleotide:M13-3.8Aa hybrid is incubated with DNA ligase and the Klenow fragment of *E. coli* DNA polymerase I, cccDNA is enriched, and the mixture is transformed into JM103. The virions produced by the transformants are isolated and used to infect cells at a low multiplicity of infection. RF DNA is isolated from a number of the infected colonies and characterized by restriction enzyme analysis. Clones derived from the mutant oligonucleotide-primed strand are identified by the presence of a HindIII site mapping at the 3'-end of the phaseolin gene, and the presence of mutant sequences at both ends of the structural gene is confirmed by sequencing. A vector containing the desired sequences is labeled M13-3.8Ab.

4.4 Inserting the insecticide gene. MBT3(Nco) RF DNA is digested with NcoI and HindIII and is mixed with and ligated to NcoI- and HindIII-digested M13-3.8Ab DNA. The mixture is transformed into K802, and plasmid DNA from kanamycin- and/or tetracycline-resistant transformants is isolated and characterized by restriction enzyme analysis. A plasmid having the insecticide structural gene inserted between the phaseolin promoter and polyadenylation site is labeled M13-PpBt, and a colony harboring it is chosen.

4.5 Moving the modified phaseolin gene into a shuttle vector. pKS111-K (Fink, supra) has the Tn5 kan gene from pKS-4 inserted between the HindIII sites of pKS111 T-DNA. M13-PpBt/RF DNA is digested with BamHI and mixed with and ligated to BamHI-linearized pKS111-K (Fink, supra). Plasmids from K802 transformants resistant to kanamycin and/or tetracycline are isolated and characterized by restriction mapping. A colony is selected which harbors a plasmid, labeled pKS111-PpBt, which contains the phaseolin promoter/insecticide structural gene/polyadenylation site combination which, together with a kan gene, is surrounded by octopine T-DNA.

4.6 Insertion into TIP plasmids, plant infection and regeneration. E. coli K802(pKS111-PpBt) is mated with A. tumefaciens as described in Example 9. The Agrobacterium strains chosen harbor TIP plasmids, based on pTi15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the Agrobacterium strains are used to infect tobacco cells which are then regenerated. The resulting plants are used as breeding stock to be crossed with various commercial varieties for which insect resistance properties are desired. Fields of regenerated plants and their insecticidal protein-containing descendants are resistant to infestation by larvae of insects such as tobacco hornworm by virtue of the toxic effect such larvae experience when eating tissue from such plants.

Example 5

Regeneration in this Example involves carrot tumors incited by Ri-based TIP plasmids and is effected essentially as described by Chilton, M.-D. et al. (1982) *Nature* 295: 423-434.

5.1 Infection with hairy root. Carrot discs are inoculated with about $10^9$ bacteria in 0.1 ml of water. One to 1.5 cm segments of the ends of the roots obtained are cut off, placed on solid (1-1.5% agar) Monier medium lacking hormones (Tepfer, D. A., J. C. Tempe [1981] *Cr. Hebd. Seanc. Acad. Sci. Paris* 295:153-156), and grown at 25° C. to 27° C. in the dark. Cultures uncontaminated by bacteria are transferred every 2 to 3 weeks and are subcultured in Monier medium lacking hormones and agar. Transformed roots can be recognized by their aberrant morphology and selected.

5.2 Regeneration of roots to plants. The cultured root tissue described in Example 5.1 is placed on solidified (0.8% agar) Monier medium supplemented with 0.36 µM 2,4-D and 0.72 µM kinetin. After 4 weeks, the resulting callus tissue is placed in liquid Monier medium lacking hormones. During incubation at 22 to 25° C. on a shaker (150 rpm) for one month, the callus disassociates into a suspension culture from which embryos differentiate, and which, when placed in Petri dishes containing Monier medium lacking hormones, develop into plantlets. These plantlets are grown in culture, and after "hardening" by exposure to atmospheres of progressively decreasing humidity, are transferred to soil in either a greenhouse or field plot.

5.3 Use of non-hairy root vectors. Ti-based vectors which do not have functional tmr genes are used instead of the Ri-based vectors as described by Hall, T. C. et al., U.S. application Ser. Nos. 06/485,613 and 06/485,614. Construction of suitable mutants can be done by those skilled in the art, and is reviewed in the Background.

Example 6

Regeneration in this Example involves tobacco leaves incited by a Ti-based TIP plasmid and is effected essentially as described by Barton, K. A. et al. (1983) *Cell* 32:1033-1043.

6.1 Infection with crown gall. Tobacco tissue is transformed using an approach utilizing inverted stem segments first described by Braun, A. C. (1956) *Canc. Res.* 16:53-56. Stems are surface sterilized with a solution of 7% commercial "CLOROX" and 80% ethanol, rinsed with sterile distilled water, cut into 1 cm segments, placed basal end up in Petri dishes containing agar-solidified MS medium (Murashige, T., F. Skoog [1962] *Physiol. Plant.* 15:473-497) lacking hormones. Inoculation is effected by puncturing the cut basal surface of the stem with a syringe needle and injecting bacteria. Stems are cultured at 25° C. with 16 hours of light per day. The calli which develop are removed from the upper surface of the stem segments, are placed on solidified MS medium containing 0.2 mg/ml carbenicillin and lacking hormones, are transferred to fresh MS-carbenicillin medium three times at intervals of about a month, and are tested to ascertain whether the cultures had been rid of bacteria. The axenic tissues are maintained on solidified MS media lacking supplements under the culture conditions (25° C.; 16 hr:8 hr light:dark) described above.

6.2 Culture of transformed tissue. Clones are obtained from the transformed axenic tissues as described by Binns, A, F. Meins (1979) *Planta* 145:365-369. Calli are converted into suspensions of cells by culturing in liquid MS having 0.02 mg/l naphthalene acetic acid (NAA) at 25° C. for 2 or 3 days while being shaken at 135 rpm, and filtering in turn through 543 and 213 µm stainless steel meshes. The passed filtrate is concentrated, plated in 5 ml of MS medium containing 0.5% melted agar, 2.0 mg/l NAA, 0.3 mg/l kinetin, and 0.4 g/l Difco yeast extract at a density of about $8 \times 10^3$ cells/ml. Colonies reaching a diameter of about 1 mm are picked by scalpel point, placed onto and grown on solidified MS medium having 2.0 mg/l NAA, 0.3 mg/l kinetin, and about 10 µg/ml S-(2-aminoethyl)-L-cysteine (AEC). (A range of concentrations of AEC, between about 2 µg/ml and about 30 µg/ml, is tried as the exact concentration effective for selection will depend on the variety of tobacco used and the growth conditions to which the source plant and tissues derived from it are subjected.) AEC has been shown to be an agent capable of selecting tissue containing octopine synthase (Dahl, Ga., J. Tempe [1983] *Theor. Appl. Genet.* 66:233-239). Alternatively, the filtrate is plated at low density (several hundred cells per ml) on a filter paper overlaying a feeder layer of tobacco cells growing on the solidified MS/NAA/kinetin/yeast extract medium. When 1 mm colonies have formed, the entire filter paper is transferred to a Petri dish containing the solidified MS/NAA/kinetin/AEC medium. The resulting calli which do not show the effects of AEC toxicity are selected, split into pieces, and tested for other transformed phenotypes such as production of octopine and hormone-independent growth.

6.3 Regeneration of plants. Transformed clones are placed onto solidified MS medium having 0.3 mg/l kinetin, and cultured as described in Example 6.1. The shoots which form are rooted by putting them on a solid (1.0% agar) medium containing 1/10 strength MS medium salts, 0.4 mg/l thiamine, lacking sucrose and hormones, and having a pH of 7.0. Rooted plantlets are grown in culture, hardened as described in Example 5.2, and are transferred to soil in either a greenhouse or field plot. Plants are screened for retention of the transformed phenotype by methods well known to those skilled in the art, such as Southern, Northern, and dot blots with appropriate probes, octopine assays, immunological (see Example 7) or biological (Example 8) assays for presence of crystal protein.

6.4 Vectors used. Constructions described by Hall, T. C. et al., U.S. application Ser. Nos. 06/485,613 and 06/485,614 are suitable Ti-based vectors lacking functional tmr genes. The method described in Example 6.1 for infection of inverted stem segments is often useful for the establishment of TIP-transformed plant cell lines.

Example 7

Anti-insecticidal protein antibody was produced by methods well known to those skilled in the art of immunology. "Western" blots, to detect antigens after SDS-polyacrylamide gel electrophoresis (SDS-PAGE), were done essentially as described by Legocki, R. P., D. P. S. Verma (1981) *Anal. Biochem.* 111:385-392.

Micro-ELISA assays are done using Immulon-2 type plates having 96 wells by the following steps:

7.1 Binding antibody to plates. On day one, the wells are coated with 1:1000 dilution of antibody (rabbit anti-insecticidal protein IgG) in coating buffer. 200 µl/well are incubated at 37° C. for 2-4 hours. The plates are covered with "SARAN WRAP" during this incubation. Afterwards the plates are rinsed three times with phosphate-buffered saline-"TWEEN" (PBS-Tween), allowing a five-minute waiting period between each rinse step. Then 1% bovine serum albumin (BSA) is added to rinse and, after addition to the well, left to sit for 20 minutes before discarding. Rinsing is repeated five times more with PBS-Tween.

7.2 Tissue homogenization. The tissue is sliced up into small pieces and then homogenized with a polytron using 1 gm of tissue/ml PBS-Tween-2% polyvinyl pyrrolidone-40 (PBS-Tween-2% PVP-40). All samples are kept on ice before and after grinding, and standard curves were obtained. One standard curve is done in tissue homogenates, and one standard curve is also done in buffer to check the recovery of insecticidal protein from homogenized tissue or cells. Following centrifugation of the homogenized samples, 100 µl of each sample is placed in a well and left overnight at 4° C. To avoid errors, duplicates of each sample are done. The plates are sealed during incubation. to the shuttle vector carrying strain and mobilized the shuttle vector for transfer to the *Agrobacterium*. Growth on a medium containing both streptomycin and the drug to which the shuttle vector is resistant, often either kanamycin or chloramphenicol, resulted in the selection of *Agrobacterium* cells containing shuttle vector sequences. A mating of these cells with *E. coli* (pPH1J1) resulted in the transfer of pPH1J1 to the *Agrobacterium* cells. pPH1J1 and pRK290-based shuttle vectors cannot coexist for long in the same cell. Growth on genta-mycin, to which pPH1J1 carries a resistance gene, resulted in selection of cells having lost the pRK290 sequences. The only cells resistant to streptomycin, gentamycin, and kanamycin are those which have Ti plasmids that have undergone double-homologous recombination with the shuttle vector and now carry the desired construction. pRK290 and pRK2013 were disclosed by Ditta, G. et al. (1980) *Proc. Natl. Acad. Sci. USA* 77:7347-7357, and pPH1J1 by Hirsh, P. R. (1978) Thesis, Univ. E. Anglia.

Example 10

This Example describes techniques for the synthesis and use of synthetic oligonucleotides. Other useful references can be found in the list of works cited in the section introductory to these Examples.

10.1 Oligonucleotide synthesis. The techniques for chemical synthesis of DNA fragments used in these Examples utilize a number of techniques well known to those skilled in the art of DNA synthesis. The modification of nucleosides is described by Schaller, H. et al. (1963) *J. Amer. Chem. Soc.* 85:3821-3827. The preparation of deoxynucleoside phosphoramidites is described by Beaucage, S. L., M. H. Caruthers (1981) *Tetrahedron Lett.* 22:1859. Preparation of solid phase resin is described by Adams, S. P. et al. (1983) *J. Amer. Chem. Soc.*. Hybridization procedures useful during the formation of double-stranded synthetic linkers are described by Rossi, J. J. et al. (1982) *J. Biol. Chem.* 257:9226-9229.

10.2 Use for oligonucleotides. Use of synthetic oligonucleotides to reconstruct a deleted segment of a gene has been exemplified by Hall et al., U.S. application Ser. No. 06/485,614. Use of synthetic oligonucleotides to link otherwise incompatible restriction site sticky-ends has been exemplified by Hall et al, U.S. application Ser. No. 06/485,614 and is well known to those skilled in the art of recombinant DNA manipulations.

10.3 Oligonucleotide-directed mutagenesis. General methods of directed mutagenesis have been reviewed recently by Shortle, D. et al. (1981) *Ann. Rev. Genet.* 15:265-294. Of special utility in manipulation of genes is oligonucleotide-directed site-specific mutagenesis, reviewed recently by Zoller, M. J., M. Smith (1983) *Methods Enzymol.* 100:468-500; Smith, M., S. Gillam (1981) in *Genetic Engineering: Principles and Methods*, Vol. 3, Setlow, J. K., A. Hollaender (eds.); Smith, M. (1982) *Trends in Biochem.* 7:440-442. This technique permits the change of one or more base pairs in a DNA sequence or the introduction of small insertions or deletions. Recent examples of use of oligonucleotide-directed mutagenesis include Zoller, M. J., M. Smith (1983) supra; Zoller, M. J., M. Smith (1982) *Nucl. Acids Res.* 10:6487-6500; Dalbadie-McFarland, G. et al. (1982) *Proc. Natl. Acad. Sci. USA* 79:6409-6413; Simons, G. F. M. et al. (1982) *Nucl. Acids Res.* 10:821-832; and Hutchinson, C. A., III et al. (1978) *J. Biol. Chem.* 253:6551-6560. Useful M13-based vectors (e.g., mWB2344) have been reported by Barnes, W. M. et al. (1983) *Meth. Enzymol.* 101:98-122; and Barnes, W. M., M. Bevan (1983) *Nucl. Acids Res.* 11:349-368.

The sequence to be modified usually is moved into a single-stranded bacteriophage vector, here one derived from M13, by standard techniques well known to those in the art. The vector DNA is generally in the double-stranded replicative form (RF), as the single-stranded viral form cannot ordinarily be "cut and spliced" by restriction enzymes and ligases. After in vitro ligation of the fragment into the RF, transformation into a suitable host, and production of single-stranded DNA (ssDNA) as part of the life cycle of the vector, ssDNA is isolated from phage particles and hybridized to an oligonucleotide having sufficient length and sequence homology to hybridize to the vector in the appropriate location. The oligonucleotide should have the sequence desired as an end product and otherwise differ in no way from the sequence to be changed. Once a hybrid is formed comprising a ssDNA circle base-paired to the oligonucleotide carrying the mutant sequence, the oligonucleotide primes synthesis of a complementary strand of DNA by the Klenow fragment of *E. coli* DNA polymerase I, a polymerase lacking a 5'-to-3' exonuclease activity. The vector is optionally incubated with DNA ligase, and the polymerase and ligase reactions may be done simultaneously. Preferentially covalently closed-circular double-stranded DNA (cccDNA) molecules can be selected before transformation by techniques which include alkaline sucrose gradient centrifugation, extraction with phenol under alkaline conditions, and incubation with S1 nuclease. The vector can now be transformed into an appropriate bacterial host cell. Virus particles from this initial infection are isolated and used to form plaques by infecting a lawn of bacteria. In cases where one is changing a restriction site, one may readily screen RFs by restriction enzyme analysis. One may also screen by hybridization under carefully selected conditions using the synthetic mutant oligonucleotide primer as a probe, or by DNA sequencing. When a clone containing the desired change has been isolated, one may manipulate the now mutant DNA as desired using techniques well known to those skilled in the art.

Example 11

This Example teaches isolation of a clone having the 3'-end of the insecticide gene carried by p123/58-10, and the reconstruction of a full-length HD-73 crystal protein gene.

11.1 Cloning of an insecticide gene 3'-end. Immunodetection of electrophoretically separated peptides on protein blots and DNA sequencing showed that p123/58-10 and p123/58-3 each contained a partial protoxin gene. To reconstruct a complete protoxin gene, flanking DNA restriction sites were identified by Southern blots of restriction digests, a well-known technique, and overlapping clones were selected from a PstI library made from 50 MD plasmid-enriched DNA as follows: 50 MD plasmid DNA, enriched by sucrose gradient centrifugation as above, was digested to completion with PstI, mixed with and ligated to PstI-linearized pBR322, and transformed into HB101. Tetracycline-resistant transformants were screened essentially as described by Benton, W. D., R. W. Davis (1977) *Science* 196:180-182, using a probe nick-translated from the 6.7 kbp HindIII insert of p123/58-10. Plasmid DNAs isolated from strains which bound the probe were characterized by restriction enzyme analysis. A strain chosen for further work harbored pBt73-161, which contains the 3'-end of a crystal protein gene.

11.2 Construction of a full-length insecticide gene. The 5'-and 3'-ends of the protoxin genes were fused together at the unique HindIII site to form a complete protoxin gene. p123/58-10 DNA was digested with BamHI, ligated to itself, and transformed into HB101. Plasmid DNAs from ampicillin-resistant transformants were characterized by restriction enzyme analysis, and a strain was identified that harbored a plasmid, designated pBt73-10(Bam), having single BamHI and HindIII sites due to deletion of a small HindIII site-bearing BamHI fragment. A 5 kbp HindIII fragment of pBt73-161, isolated by agarose gel electrophoresis, was mixed with and ligated to HindIII-digested dephosphorylated (by bacterial alkaline phosphatase) pBt73-10(Bam) DNA. After the ligation mixture was transformed into HB101, plasmid DNA isolated from ampicillin-resistant tetracycline-sensitive transformants was characterized by restriction enzyme analysis. A transformant was identified that harbored a plasmid, designated pBt73-16, carrying a complete protoxin gene. *E. coli* HB101 (pBt73-16) is on deposit at the Northern Regional Research Center, 1815 N. University Street, Peoria, Ill. 61604 USA, as NRRL B-15759.

Example 12

This Example teaches the insertion of the full-length *Bacillus thuringiensis* insecticide gene between a T-DNA gene promoter and a polyadenylation (poly(A) addition) signal, the transfer of the insecticide gene to tobacco via a sub-Ti plasmid, the regeneration of plants containing the gene, and the expression of this gene under control of the T-DNA promoter in plant cells.

12.1 Preparation of pH400, a sub-Ti plasmid. pH4-1 DNA can be isolated from *E. coli* K802 (pH4-1), which has been deposited as NRRL B-18009. pH4-1 is a sub-Ti plasmid based on pSUP106 (Preifer, U. B. et al. [1985] *J. Bacteriol.* 163:324-330; *E. coli* CSH52 (pSUP106) is deposited as NRRL B-15486). Inserted into pSUP106's HindIII site is pTi15955 DNA having border A (the left border of $T_L$), a plant-expressible selectable marker, the 5'-end of tml, a complete ocs gene, and border B (the right border of $T_L$). The plant-expressible marker is sutured to the adjoining pTi15955 sequences at BglII sites made up of a Tn5 neomycin phosphotransferase II (NPT2) structural gene capable of detoxifying kanamycin and related antibiotics (a kan gene). The NPT2 structural gene is transcribed in plant cells under control of a cauliflower mosaic virus (CaMV; for a review of CaMV see Hohn, T. et al., *Curr. Top. Microbiol. Immunol.* 96:193-236) 19S transcript promoter and a pTi15955 ORF26 (as defined by Barker, R. F. et al. [1983] *Plant Mol. Biol.* 2:335-350) polyadenylation site. The NPT2 structural gene is oriented so that it is transcribed in the same direction as the ocs gene. In other words, the T-DNA of pH4-1 is essentially identical to $T_L$-DNA of pTi15955 except for substitution of a CaMV 19S promoter NPT2 structural gene/ORF26 polyadenylation site combination for T-DNA between the position 1617 BglII site and the position 11207 SmaI site, T-DNA positions being defined by Barker et al., supra.

pH4-1 has two BglII sites, both of which flank the kan selectable marker. One of the BglII sites was removed, thereby leaving a unique BglII site useful for insertion of extraneous coding DNA pH4-1 DNA was linearized by being partially digested with BglII and full-length, linear DNA was electrophoretically isolated. The BglII sticky-ends were then removed by incubation with the Klenow fragment of *E. coli* DNA polymerase I. The resulting blunt-ended DNA was ligated to itself and transformed into *E. coli*. Plasmid DNAs isolated from transformants resistant to chloramphenicol were screened by restriction analysis and a colony was identified which harbored a plasmid designated pH400. pH400 is identical to pH4-1 except for the absence of the BglII site between the kan gene and the ORF1 promoter, the unique pH400 BglII site being located between the kan gene and the ocs gene. The single BglII site is a convenient place to insert DNA, in particular if that DNA has compatible 5'GATC . . . 3' sticky-ends resulting from the action of BglII, BclI, or BamHI.

12.2 Preparation of pDOB513. pDOB512, carrying cauliflower mosaic virus (CaMV) transcription controlling sequences (obtained from Dr. Ken Richards, Centre National de la Recherche Scientifique, Institute de Biologie Moleculaire et Cellulaire, 15, rue Descartes, F-67084 Strasbourg, France) was constructed as follows: AHind III fragment carrying the CaMV 19S RNA promoter region (CaMV nucleotides 5376-5851) was inserted into pBR322 and was trimmed back to within one base pair of the 19S transcript cap site. An adapter molecule having both a SmaI site and a BamHI site (the structure being 5'-CCCGGGGATC CGG-3':5'-CCGGATCCCC GGG-3', see below) was then ligated to the trimmed DNA. A HincII fragment carrying the CaMV 19S transcript terminator (CaMV nucleotides 7018-7794) to which BamHI linkers had been added was then inserted behind the 19S promoter, the promoter and terminator being separated by the SmaI/BamHI linker. The resulting plasmid is designated pDOB412. pDOB412 DNA was digested with BglII and SalI, filled in by incubation with the Klenow fragment of E. coli DNA polymerase I, and religated, thereby deleting DNA, which includes BamHI and HindIII sites, between the CaMV position 7644 BgI11 site and the pBR322 position 650 SalI site and regenerating a BglII site. The resultant plasmid was designated pDOB512.

The sticky-ends of HindIII-linearized pDOB512 DNA were converted to blunt-ends. The blunt-ended pDOB512 DNA was mixed with and ligated to commercially available BglII linkers. The ligation mix was transformed into E. coli K802 and an ampicillin-resistant transformant was isolated which harbored a plasmid, designated pDOB513 (FIG. 3). pDOB513 has CaMV 19S transcription controlling sequences on a BglII fragment. SmaI and BamHI sites are found between the DNA segments having the promoter and the polyadenylation site in both pDOB412, pDOB512, and pDOB513, thereby providing a convenient location for insertion of foreign DNA that is to be a template for a transcript. The sequence of this suture is as follows:

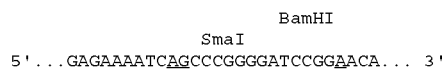

The first underlined base, an A, corresponds to the first base of the 19S mRNA, transcription being towards the right, and the second and third underlined bases, respectively a G and an A, are derived from CaMV sequences at positions 5765 and 7018, respectively, as defined by Hohn et al., supra.

12.3 Preparation of T-DNA ORF24 transcription controlling sequences. pKS-proI was prepared essentially as described in Example 2.2. pSK111 is a recombinant plasmid having Ti15955 T-DNA which spans the sequence between EcoRI sites at positions 16,202 and 21,631 (as defined by Barker et al., supra) inserted into the EcoRI site of pRK290 (Ditta, G. et al. [1980] Proc. Natl. Acad. Sci. USA 77:7347-7351). E. coli K802 (Wood, W. B. [1966] J. Mol. Biol. 16:118) methylates DNA at many, but not all, ClaI sites, thereby specifically protecting certain sites from the action of ClaI. The only susceptible ClaI sites of pKS111 are the sites at T-DNA positions 18,892 and 20,128. These sites define a DNA fragment which includes the ORF24 (as defined by Barker et al., supra) structural gene but does not include the ORF24 promoter or polyadenylation site. ORF24 is associated with mannopine synthesis. Plasmid DNA isolated from E. coli K802 (pKS111) was digested with ClaI, ligated to itself, and transformed into K802. A tetracycline-resistant transformant was identified by restriction analysis which harbored a plasmid, designated pKS-proI (or alternatively, pTR-proI), identical to pKS111 except for deletion of a fragment which spanned the ClaI sites at positions 18,892 and 20,128.

pTR-proI DNA was isolated and cleaved at its single ClaI site (the suture between the sites at positions 18,892 and 20,128) by incubation with ClaI. After the ClaI sticky-ends were then removed by incubation with the Klenow fragment of E. coli DNA polymerase I, the blunt-ended DNA was mixed with and ligated to commercially available BamHI linkers having the self-complementary sequence 5'-CG-GATCCG-3'. After digestion of the BamHI-linked DNA with BamHI, religation to itself, and transformation of the resulting DNA into K802, plasmid DNAs were isolated from transformants resistant to tetracycline and were characterized by restriction mapping. A colony was identified which harbored a plasmid, designated pTR-proI(Bam), lacking a ClaI site at the T-DNA positions 18,892/20,128 suture but, instead, having a BamHI site at the former location of that ClaI site.

pBR322 has a BamHI site which is inconvenient for later manipulations. Therefore, the T-DNA of the ClaI-deleted pKS111-derivative was transferred to a pBR325 derivative which was lacking a BamHI site. pBR325DNA, isolated from E. coli GM33 (pBR325), was digested with both BamHI and BclI, was ligated to itself, and was transformed into E. coli. GM33 (Marinus, M. G., R. N. Morris [1974] J. Mol. Biol. 85:309-322) does not methylate adenine residues of DNA. Plasmid DNA isolated from transformants sensitive to tetracycline and resistant to chloramphenicol and ampicillin were characterized by restriction mapping, and a colony was identified which harbored a plasmid, designated pBR325aBB, which could not be cleaved with either BamHI or BclI. pTR-proI DNA was digested with EcoRI and was mixed with and ligated to EcoRI-linearized, dephosphorylated pBR325aBB DNA After transformation into E. coli, plasmid DNAs isolated from transformants resistant to ampicillin and sensitive to both chloramphenicol and tetracycline were characterized by restriction mapping. A colony was identified which harbored a plasmid, designated p403B, having the ClaI-deleted T-DNA with BamHI linkers in the former ClaI site, recombined with the pBR325aBB vector.

pKS4.2 DNA (Example 2.3) was digested with ClaI, and a fragment carrying the kan gene was electrophoretically isolated. This fragment was mixed with and ligated to ClaI-linearized pBR322 and transformed into E. coli. Plasmid DNAs isolated from transformants resistant to ampicillin and kanamycin were screened by restriction analysis and a colony was identified which harbored a plasmid designated pKS4.3. The pKS4.3 kan gene was oriented with its 5'-end and 3'-end respectively proximal to the pBR322EcoRI and BamHI sites. In this orientation, the kan gene may be removed on a HindIII fragment.

BamHI-linearized pBR322 DNA was mixed with and ligated to BglII-digested bacteriophage lambda DNA. Transformation into E. coli cells was followed by selection for resistance to ampicillin and screening for sensitivity to tetracycline. Plasmid DNAs were then isolated and screened by restriction analysis and a colony was identified which harbored a plasmid, designated pBR322Bam⁻, which could not be cleaved with BamHI.

pKS4.3 DNA was digested with HindIII and the kan gene-bearing fragment was electrophoretically isolated. The kan fragment was then mixed with and ligated to HindIII-linearized pBR322Bam⁻DNA. The ligation mixture was then transformed into E. coli. Plasmid DNAs isolated from transformants resistant to both kanamycin and ampicillin were screened by restriction analysis and a colony was identified which harbored a plasmid, designated p11-83c, having the kan fragment inserted into pBR322Bam⁻'s HindIII site. In p11-83c the kan gene was oriented so that the kan gene was transcribed in the same direction as the ampicillin resistance (amp) gene.

pTR-proI(Bam) was digested with EcoRV and an approximately 2.26 kbp fragment bearing the ORF24 ("1.6" transcript) promoter and polyadenylation site, but lacking the ORF24 structural gene, was electrophoretically isolated. The EcoRV sticky-ends were then converted to blunt-ends by the action of the Klenow fragment of E. coli DNA polymerase I. The blunt-ended fragment was then mixed with and ligated to commercially available BglII linkers. After trimming off excess linkers by digestion with BglII, the fragment was mixed with and ligated to BglII-linearized p11-83c DNA. The ligation mixture was then transformed into E. coli. Plasmid DNAs isolated from ampicillin-resistant, kanamycin-sensitive transformants were restriction mapped and a colony was identified which harbored a plasmid, designated pCG116, having a BglII fragment bearing the ORF24 promoter and polyadenylation site inserted into Tn5 DNA between the kan promoter and kan structural gene.

pDOB513 DNA was digested with BglII, religated to itself, and transformed into K802. Colonies which harbored a plasmid, designated pDOB514, deleted for CaMV transcription controlling sequences were identified by restriction mapping of the harbored plasmids.

pCG116 DNA, which had, on a 2.26 kbp Bgm fragment, a BamHI site between the ORF24 promoter and transcript terminator, was then digested with BglII, which cleaves at sites which in T-DNA correspond to positions 18,027 and 21,522 EcoRI sites. The restriction digested DNA was mixed with and ligated to BglII-linearized pDOB514 DNA. Plasmid DNAs of ampicillin-resistant transformants were characterized by restriction mapping, and a colony was identified which harbored a plasmid, designated pMAN514, having a 2.29 kbp BglII fragment carrying an ORF24 promoter and polyadenylation site separated by a BamHI site.

12.4 Preparation of the insecticide gene. After pBt73-16 was digested with NdeI, resulting NdeI sticky-ends were filled in by incubating the mixture with T4 DNA polymerase and all four dNTPs. The blunt-ended Bacillus DNA was mixed with and ligated to double-stranded, SmaI-lineanzed, M13 mp19 RF DNA (Norrander, J. et al. [1983] Gene 26:101-106). The ligation mixture was transformed into E. coli JM105. DNAs isolated from plaques that were "clear" when plated on indicator plates were characterized by restriction analysis and a plaque was identified which harbored a vector, designated 1.6.4, having a 3.6 kbp Bacillus thuringiensis DNA oriented such that single-stranded form was complementary to crystal protein mRNA (i.e., the phage carried the antisense strand).

A BamHI site was introduced into the *Bacillus* DNA immediately 5' to the crystal protein translational start site essentially as described in Example 10. Sequences of the unmutated *Bacillus* DNA and the oligonucleotide primer are as follows:

```
                           TAA
Bacillus: 5'...GAGATGGAGG    CTTATGGATAAC...3'
Primer:       5'GAGATGGAGGGATCCTTATGGATAAC3'
                         BamHI   MetTyrHis
```

Putative mutant DNAs were screened for hybridization under stringent conditions to a $^{32}P$-label derivative of the oligonucleotide primer and for the presence of a novel BamHI site. A plaque was identified harboring a vector designated 1.6.4B-3.8.3, having a BamHI site immediately 5' to the translational start. Fidelity of the in vitro mutation was confirmed by DNA sequencing. The insecticidal protein structural gene may be removed from double-stranded 1.6.4B-3.8.3 RF DNA on a 3.75 kbp BamHI fragment resulting from cleavage at the novel site in the *Bacillus* sequence and a BamHI site which is 3' to the structural gene in the M13 mp19 polylinker.

12.5 Combination of an insecticidal protein structural gene with ORF24 transcription controlling sequences. Double-stranded 1.6.4B-3.8.3 RF DNA and pCG116 DNA, both having been digested with BamHI, were mixed with each other and ligated together. After the ligation mixture was transformed into *E. coli*, plasmid DNAs isolated from ampicillin-resistant transformants were characterized by restriction analysis. A colony was identified which harbored a plasmid, designated pCJ161, having a full-length insecticidal protein structural gene placed between the ORF24 promoter and ORF24 polyadenylation site in an orientation such that the mRNA transcribed under control of the ORF24 promoter encodes the insecticidal protein.

12.6 Insertion of a plant-expressible insecticide gene into a sub-Ti plasmid. pCJ161 and pH400 DNAs, having been digested with BglII, were mixed with each other and ligated together. After the ligation mixture was transformed into *E. coli*, plasmid DNAs isolated from ampicillin-resistant transformants were characterized by restriction analysis. A colony was identified which harbored a plasmid, designated pH450, having the ORF24 promoter/crystal protein structural gene/ORF24 polyadenylation site combination inserted into the pH400 BglII site, which is located between the ocs gene and the plant-expressible kan gene. The plant-expressible crystal protein gene of pH450 is oriented so that it is transcribed in the same direction, i.e., off of the same DNA strand, as both the ocs gene and the kan gene.

12.7 Plant transformation. pH450 was transferred into *A. tumefaciens* LBA4404 (Ooms, G., et al. [1981] *Gene* 14:33-50), a vir gene-bearing micro-Ti-mobilizing strain, by the triparental mating technique. Tobacco leaf tissues were inoculated using a modification of the method of Horsch, R. B. et al. (1985) *Science* 227:1229-1231. Leaf segments were dipped in the inoculating suspension of bacteria for 1-3 minutes. The inoculating bacterial suspensions had titres of $10^7$-$10^8$ $ml^{-1}$; the exact concentration was found to be unimportant. The medium was a tobacco regenerating medium having MS salts, a mixture well known to the art, supplemented with 0.1 mg/l p-chlorophenoxyacetic acid (pCPA), 7.5 mg/l &(2,2-dimethylallylamino)-purine (2iP), 300 mg/l kanamycin, and 125 mg/l cloxacillin, mefoxin and 500 mg/l carbenicillin. Generally 75-80% of the shoots were able to root in a kanamycin-containing medium and all were transformed. Some kanamycin-resistant shoots did not make measurable quantities of octopine.

12.8 Expression in plant tissues: immunoassays. Micro-ELISA double antibody sandwich assays were performed using a modification of the method of Example 7.

Antibodies were prepared by well-known methods. Coating antibody was partially purified mouse polyclonal antisera which was raised to *B. thunngiensis* HD-73 crystal protein. The mouse antisera was partially purified by precipitation with 50% (w/v) saturated ammonium sulfate at pH 7.4. The milky precipitate that forms during 30 minutes on ice was pelleted by centrifugation (20 minutes, 10,000 rpm). The pellet was then resuspended in phosphate buffered saline (PBS, pH 1.4) containing 137 mM NaCl, 1.5 mM $KH_2PO_4$, 2.7 mM KCl, and 8 mM $NaHPO_4$. The resulting coating antibody sample was then dialyzed overnight in PBS at 4° C.

Primary antibody was partially purified rabbit polyclonal antisera raised to *B. thuringiensis* HD-73 crystal protein. This antisera was cleared of antibodies that react with tobacco leaf protein. Tobacco leaf protein was bound to CNBr-activated "SEPHAROSE 4B" (Pharmacia, Upsalla, Sweden) (10 mg protein/ml gel). Rabbit serum was diluted 1:4 (v/v) with PBS and added to the swollen "SEPHAROSE" gel to which the leaf protein was bound. About 2-3 ml of gel was used for 4 ml of diluted serum. The serum-gel mixture was incubated with gentle shaking for about 1 hour at room temperature. Antibodies that react with leaf protein remain bound to the gel. The liquid containing unbound antibodies was removed from the gel matrix by aspiration. The antibody solution was then partially purified by precipitation with 50% saturated ammonium sulfate followed by overnight dialysis against PBS at 4° C.

Secondary antibody was commercial goat anti-rabbit IgG (H+L) labeled with alkaline phosphatase (Kirkegaard and Perry, Gaithersburg, Md.). Sterile, distilled water (1 ml) was added to 0.5 mg of lyophilized pellet. The wells of disposable flexible 96-well/flat bottom microtitration plates (Dynatech, Alexandria, Va.) were coated (100 μl/well) with coating antibody (1:2000 dilution of coating antibody in coating buffer). Coating buffer contained 5 mM $Na_2HCO_3$ and 35 mM $NaHCO_3$ at pH 9.6 After addition of the coating antibody solution, the plates were covered and stored at 4° C. for at least 12 hours. The contents of the wells were then discarded and the entire plate was rinsed about 3-4 times with a wash buffer of PBS containing 0.05% polyoxyethylenesorbitan monolaurate ("TWEEN-20"). Plates were then filled with wash buffer and placed on a shaker for 5 minutes followed by a final rinse. The plates were then drained for 30 seconds. It is important that at no point in the assay the wells dry for a prolonged period. In between assay steps the wells were filled with wash buffer.

The plates were next treated with blocking solution to prevent non-specific binding of proteins. Plate wells were filled with blocking solution containing 1% (w/v) bovine serum albumin (BSA); 1% (w/v) casein, acid hydrolysate, type 1; and 0.05% (v/v) polyoxyethylenesorbitan monolaurate ("TWEEN-20") and allowed to stand at room temperature for 30 minutes to 1 hour.

Tobacco plant tissue samples were prepared from leaf material. Generally, 1 or 2 leaves from the apex of the plant were combined with 4 or 5 leaf discs (7 mm) from the basal and marginal regions of the next youngest leaves. Tissue samples of about 100 mg were used. After weighing, tissue samples were quick-frozen in liquid nitrogen and ground in a tissue grinder. The sample was allowed to warm to room temperature during grinding. After the tissue was completely ground, PBS was added to make a solution containing 0.3 mg fresh weight/μl (for a 100 mg sample, 500 μl of PBS was added). Callus tissue samples were prepared in the same manner, except that PBS was added to ground tissue to give a solution of 0.5 mg fresh weight/μl. Samples were then mixed thoroughly and allowed to stand at 4° C. (about 20 minutes) for tissue to settle out. Samples (10-15 μl) of the supernatant were taken for total protein assays. Samples were then diluted with an equal volume of a 2× concentration of sample buffer. Sample buffer (1×) contained PBS (pH 7.4) with 2% (v/v) polyethylene glycol, 1% (v/v) polyvinyl pyrolidone, 0.1% (w/v) BSA, 0.1% (w/v) casein, acid hydrolysate, 10 μg/ml "APROTININ" (Sigma), a protease inhibitor, 0.05% (v/v) polyoxyethylenesorbitan monolaurate, and 0.006% (v/v) β-mercaptoethanol. Control tissue (non-transformed) samples were prepared in a similar manner. Samples were spun in a microfuge for 1 minute before loading into wells of the prepared microtiter plates. Sample supernatant was loaded (100 μl/well) in replicates (3 or 4). Plates containing samples are incubated for 2-3 hours at room temperature. For quantitation, standards of *B. thuringiensis* crystal protein can be included.

After incubation the contents of the wells were removed and the plate was rinsed carefully with wash buffer (4-5 times). The plate was filled with wash buffer and agitated for 5 minutes. Care should be taken in this step to avoid cross-contamination of samples, controls, and standards.

A 1:2000 dilution of the primary antibody in antibody buffer was then loaded into the wells (100 μl/well). Plates were covered and stored at 4° C. overnight (about 12 hours). Antibody buffer contained PBS (pH 7.4) with 1% (v/v) goat serum and 0.05% polyoxyethylenesorbitan monolaurate. Plates were then washed (3-4 times) with wash buffer (as above). Plates were then blotted dry.

A 1:2500 dilution of labeled secondary antibody (goat anti-rabbit IgG (H+L)-alkaline phosphatase-labeled) was then loaded into wells (100 μl/well). Plates were incubated for 1-2 hours at room temperature and thoroughly washed. Plates were washed 4-5 times with wash buffer. Plates were filled with wash buffer and placed on a shaker for at least 10 minutes. Plates were rinsed again and blotted dry.

An NADH substrate was then employed to detect bound labeled antibody. NADP (β-nicotinamide adenine dinucleotide phosphate) 0.25 mg/ml in 0.50 mM $MgCl_2$, 0.05 mM diethanolamine (pH 9.5) was loaded into the assay wells (100 μl/well). Plates were covered and stored at 4° C. for about 1½ hours.

Reagent solutions was prepared by dissolving p-Iodonitrotetrazolium violet (0.31 mg/ml) in 0.05 M sodium phosphate buffer (pH 7.2) containing 1.9% (v/v) ethanol. To this solution "DIAPHORASE" (NADH/dye oxidoreductase; Boehringer Mannheim, Mannheim, West Germany) to 0.035 mg/ml and alcohol dehydrogenase (baker's yeast) to 0.035 mg/ml were added. The reagent solution was incubated at 4° C. for 45 minutes, after which it was added to the NADP solution in each assay well (150 μl/well).

The color reaction (red) should begin immediately. Optical density measurements were read at 492 nm.

Adjusted ELISA values of crystal protein in leaf tissue, expressed as absorbance at 492 nm, are reported in Table 7. The values were adjusted by subtracting from each measurement the value obtained for a *Nicoliana tabacum* var. "Xanthi" control. Many plants were observed to contain measurable amounts of antigen which bound anti-crystal protein antibody.

12.9 Expression in plant tissues: bioassays. Tobacco tissue transformed by pH450 was cloned and maintained in a growth chamber. For bioassay, leaves were cut off with a razor blade and placed in a 9 cm Petri dish lined with moist filter paper. Newly-hatched tobacco hornworm larvae (*Manduca sexta*) were put on the leaves. Mortality was recorded.

In trial 1, three clones from each type were sampled with five larvae per dish (Table 8). The data can be summarized as follows:

| Clone | Total | Dead | % Dead |
|---|---|---|---|
| 100 | 14 | 5 | 36 |
| 103 | 15 | 1 | 7 |
| 106 | 15 | 0 | 0 |
| 109 | 15 | 5 | 33 |
| 111 | 15 | 3 | 20 |

Trial 2 was essentially done as described for trial 1, but here two larvae were placed in each dish. The data are reported in Table 9 and can be summarized as follows:

| Clone | Total | Dead | % Dead |
|---|---|---|---|
| 100 | 14 | 9 | 64 |
| 103 | 18 | 4 | 22 |
| 106 | 24 | 12 | 50 |
| 109 | 26 | 7 | 27 |
| 111 | 18 | 8 | 44 |

Leaves that had killed both larvae by day 2 were then reinfested with three newly hatched larvae. While the numbers were not large enough to make comparisons between treatments, it was clear that these leaves are still toxic. For example, three dishes from clone 100 received a total of 9 larvae, 6 of which were dead 2 days later.

As protein concentration is highest in small leaves, expression might vary with the size of the leaf, i.e., with the degree of expansion of the cells. Therefore in trial 3 leaves were measured before bioassay. For this test, only plants that had not been sampled before of clones 100 and 103 were sampled. The data were ranked from smallest to largest leaves, but the sizes for the two clones were not aligned. Different numbers of dishes were set up for each plant because the plant of clone 100 had fewer leaves. Three larvae were placed in each dish. Number of dead larvae per dish are reported below.

| Rank | Clone 100 | Clone 103 |
|---|---|---|
| 1 | 1 | 0 |
| 2 | 3 | 0 |
| 3 | 1 | 0 |
| 4 | 1 | 0 |
| 5 | 1 | 0 |
| 6 | 3 | 0 |
| 7 | 3 | 0 |
| 8 |   | 0 |
| 9 |   | 2 |
| 10 |   | 1 |

It is clear that both small and large leaves are able to kill the larvae. Furthermore, the difference between different plant clones, i.e., 100 and 103, is apparent: 62% vs. 10% mortality, at day 2.

In trial 4, randomly assigned labels were used to avoid biases. Five Petri dishes from each clone were prepared with three larvae per dish. In addition, a Xanthi plant that originated in tissue culture was used as a control. The data can be summarized as follows:

| Summary | Dead/Total | % Mortality |
|---|---|---|
| control | 2/15 | 13 |
| 100 | 11/15 | 73 |
| 103 | 8/15 | 53 |
| 106 | 2/15 | 13 |
| 109 | 1/15 | 7 |
| 111 | 3/15 | 20 |

Clone 100 gave consistently high mortality. Clone 103 also gave high mortality explained by the subsequently discovered fact that "clone" 103 was not in fact a clone; the original transformed plant has now been shown to have been a chimeric plant. It has not proven to be particularly insecticidal in any other of the five trials.

After the trial 4 leaves had been fed on for two days, ELISAs were performed on some of the lethal and nonlethal leaves. No crystal protein antigen was detected because of the low levels of protein in these leaves.

In trial 5, four plants were propagated from clone 100 and five from clone 103. Five leaves were sampled from each of these plants. Each leaf was placed in an individual Petri dish with three newly hatched larvae. The data can be summarized as follows:

| Summary | Dead/Total | % Mortality |
|---|---|---|
| 100 | 8/14 | 57 |
| 100 | 3/14 | 21 |
| 100 | 10/15 | 67 |
| 100 | 5/14 | 36 |
| 103 | 3/15 | 20 |
| 103 | 1/15 | 7 |
| 103 | 2/15 | 13 |
| 103 | 2/15 | 13 |

Thus, clone 100 is consistently more toxic than clone 103.

Southern blot analysis of DNA isolated from presumptive transformants showed that cloned plant tissue having insecticidal activity in bioassays and containing crystal protein antigen generally had pH450's T-DNA. Northern blot analysis of RNA generally demonstrated the presence of mRNA having crystal protein sequences. These mRNA molecules were not the expected size of about 3.8 kbp, but were about 1.7 kbp in size. This was sufficient to encode the toxic portion of the crystal protein. As predicted from the fact that crystal protein levels in leaves as estimated by ELISA were below the limit of detection on Western blots, Western blot analysis of proteins extracted from transformed tissues did not reveal any antigens that cross-reacted with anti-crystal protein antibodies. Polypeptides that bind anti-crystal protein antibodies have been detected by Western blot analysis of both transformed callus and young shoot tissues.

Example 13

This Example teaches more DNA constructions useful for transformation of a number of species of plants.

13.1 Plant transformation vectors. pH450 was described in Example 12.6. pH575 was disclosed by Sutton et al. (1987) European Patent Publication 0 223 417 (priority document: U.S. patent application Ser. No. 06/788,984, filed Oct. 21, 1985, which is hereby incorporated by reference). pH576, pH577, pH578, pH582, and pH585 are derivatives of pH575, having various promoter/insecticide structural gene/polyadenylation site combinations, all oriented parallel to the ocs gene and the plant-selectable kan gene and inserted into the BglII site of pH575 between those two genes.

13.2 Modification of an insecticide gene's 5'-end. Construction, isolation, and characterization of pNSBP544 were disclosed by Sekar et al. (1987) Proc. Natl. Acad. Sci. USA 84:7036-7040; and Sekar and Adang, U.S. patent application Ser. No. 07/108,285, which is hereby incorporated by reference. A 3.0 kbp HindIII fragment carrying the crystal protein gene of pNSBP544 was inserted into the HindIII site of pIC-20H (Marsh et al. [1984] Gene 32:481-485), thereby yielding a plasmid designated p544-HindIII, which is on deposit. 73 kDa crystal protein may be expressed in E. coli. The 73 kDa species is processed to form the 65 kDa species by removal of 49 amino acids at the amino-terminus of the 73 kDa species, leaving alanine at the amino-terminus of the 65 kDa species.

A 5.9 kbp BamHI fragment carrying the crystal protein gene was removed from pNSBP544 and inserted into BamHI-linearized pIC-20H DNA. The resulting plasmid, p405/44-7, was digested with BglII and religated, thereby removing Bacillus sequences flanking the 3'-end of the crystal protein gene. The resulting plasmid, p405/54-12, was digested with PstI and religated, thereby removing Bacillus sequences flanking the 5'-end of the crystal protein and about 150 bp from the 5'-end of the crystal protein structural gene. The resulting plasmid, p405/81-4, was digested with SphI and PstI and was mixed with and ligated to a synthetic linker having the following structure:

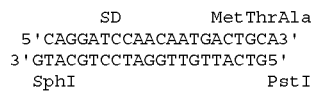

(SD Indicates the Location of a Shine-Dalgarno Prokaryotic Ribosome Binding Site.) The resulting plasmid, p544Pst-Met5, contains a structural gene encoding a protein identical to one encoded by pNSBP544 except for a deletion of the amino-terminal 47 amino acid residues. The protein encoded by p544Pst-Met5 is 2 amino acids longer than the 65 kDa toxic polypeptide processed from the 75 kDa crystal protein encoded by pNSBP544 (data not shown; see also McPherson et al. [1988] Biotechnol. 6:61-66). In bioassays, the proteins encoded by pNSBP544 and p544Pst-Met5 were shown to be equally toxic. All of the plasmids mentioned above have their crystal protein genes in the same orientation as the lacZ gene of the vector.

13.3 Modification of an insecticide gene's 3'-end. A HindIII site and a XmaI site were removed from the kanamycin resistance gene (kan), which encodes neomycin phosphotransferase I (NPTI), of pUC4K (Viera and Messing [1982] Gene 19:259-268) by the method of Merlo and Thompson (1987) Anal. Biochem. 163:79-87. The kan gene was removed from the resulting plasmid on a HincII fragment, and the ends were filled in by T4 DNA polymerase to make sure that they were blunt. pIC-20R (Marsh et al., supra) DNA was digested with NdeI and ScaI and the ends were filled in by T4 polymerase. The resulting DNA, lacking the 5'-end of the ampicillin-resistance gene (amp) was mixed with and ligated to the NPT1-encoding HincII fragment. A plasmid having kan in the same orientation as amp was identified and labeled pIC-20RXmn⁻Kan'.

A HindIII fragment carrying the crystal protein gene was removed from p544Pst-Met5 and inserted into the HindIII site of pIC-20RXmn⁻Kan'. A plasmid having the crystal protein gene oriented antiparallel to the pIC-20R lacZ gene was identified and designated p461/80-159. p461/80-159 DNA was digested with BglII and XmnI which opened it at the BglII site of the pIC-20R polylinker and just after nucleotide 1778 (XmnI) of the crystal protein gene. The opened plasmid was mixed with and ligated to a synthetic DNA linker having the following structure:

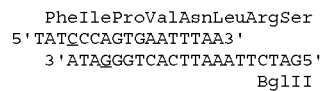

(The underlined base pair indicates a mutation that eliminates the XmnI site present in the wild-type gene.) The resulting plasmid was designated p461/97-14.

13.4 Fusion of an insecticide gene with NPT2 sequences. The kan gene of Tn5 was modified as follows (see Merlo et al., European Patent Application Publication No. 0 233 417, priority U.S. patent application Ser. No. 06/788,984, continued by Ser. No. 07/144,016). Coordinates refer to the sequences published by Beck et al. (1982) Gene 19:327-336. The G at position 144 was changed to a C, thereby introducing a BamHI site. The C at position 148 was changed to an A, thereby improving the efficiency of eukaryotic translational initiation at the AUG at position 151 to 153. The SmaI site that cuts after position 1118 was changed to a BglII site by digestion with SmaI followed by ligation to BglII linkers. The NPT2 gene is carried by a 0.98 kbp DNA fragment after digestion with BamHI and BglII.

The 0.98 kbp fragment was mixed with and ligated to BglII-digested p461-97-14 (Example 13.3). A plasmid, p461/151-174, was identified having the NPT2 sequence oriented with its 5'-end BamHI site fused with the BglII site proximal to the truncated Btt crystal protein gene of p461/97-14. The suture of p461/151-174 between the Tn5 and B. thuringiensis sequences was sequenced to confirm conservation of reading frame.

13.5 Construction of transcription vectors. An 833 base pair (bp) fragment was cut out of the pUC13 clone carrying the "−343" deletion (Odell et al. [1985] Nature 313:810-812) by digestion with SmaI and Hind III. This fragment carries a functional 35S promoter and the 5'-end of the CaMV 35S transcript, spanning from position −343 to position +9 relative to the transcriptional start site. This fragment was ligated into pIC19R (Marsh et al. [1984] Gene 32:481-485) which had been digested with NruI and HindIII. The ORF25 polyadenylation site was contributed by a pTi15955 fragment spanning HincII sites at positions 21,727 and 22,440, as disclosed by Barker et al. (1983) Plant Mol. Biol. 2:335-350, ligated into the SmaI site of pIC19H (Marsh et al., supra), the ORF25 polyadenylation site being proximal to the BamHI site in the pIC19H polylinker. The T-DNA was then removed from the pIC19H vector on a BamHI/BglII fragment which was then inserted into the BamHI site of the pIC19R/35S promoter combination, the T-DNA being oriented so that the ORF25 polyadenylation site was proximal to the 35S promoter, a functional BamHI site was between the CaMV and T-DNA sequences, and a BamHI/BglII fusion was between the T-DNA and pIC19R sequences. This plasmid was then opened at the SmaI site between the fused BamHI/BglII site and the pIC19R vector sequences. Plural BglII linkers were ligated into the SmaI site, resulting in formation of a PstI site between the linkers. The resulting plasmid was designated pIC35/A.

A DNA linker encoding the tobacco mosaic virus (TMV) 5'-leader sequence was synthesized. The linker had the structure of

```
       (BglII)                           Tth111II                                              (BamHI)
5' GATCTATTTTTACAACAATTACCAACAACAACAAACAA......CAAAACAACATTACAATTACTATTTACAATTACG    3'
3'     ATAAAAATGTTGTTAATGGTTGTTGTTGTTTGTT......GTTTTGTTGTAATGTTAATGATAAATGTTAATGCCTAG 5',
``` the horizontal lines indicating the location of sites recognized or partially recognized (partial recognition is indicated by parentheses) by the indicated restriction enzymes. This linker was inserted into pIC351A's BamHI site. The resulting plasmid, designated pIC35/A-TL4, had a BamHI site between the TMV leader and the ORF25 polyadenylation site.

An NPT2 expression vector was constructed having the same CaMV DNA fragment carrying the 35S promoter as pIC35, the same NPT2 structural gene as used in Example 14.2.2 to construct p461/151-174, and the same T-DNA ORF25 polyadenylation site as used in pIC35/A. A 3.0 kbp HindIII fragment carrying the truncated Btt crystal protein gene of pNBSP544 was inserted into pIC19R-Kan or p35S-Kan.

13.6 Assembly of direct transformation vectors. The insecticide structural gene/fusion linker combination of p461/97-14 was removed by digestion with BglII and BamHI and inserted into BamHI-linearized pIC35/A-TL4 DNA. A plasmid, designated p461:151-193, was identified which had the insecticide structural gene oriented so that the 5'-end of the insecticide structural gene was proximal to the 35× promoter and the 3'-end of the linker was proximal to the ORF25 polyadenylation site.

The insecticide structural gene/fusion linker/NPT2 structural gene combination of p461/151-174 was removed by digestion with BglII and BamHI and inserted into BamHI-linearized pIC35/A-TL4 DNA, A plasmid, designated p461:162-191, was identified which had the insecticide structural gene oriented so that the 5'-end of the insecticide structural gene was proximal to the 35S promoter, and the 3'-end of the NPT2 structural gene was proximal to the ORF25 polyadenylation site.

13.7 Fusion of an insecticide gene with hygromycin sequences. An insecticide structural gene was derived from a 5.3-class gene (Kronstad and Whiteley [1986] *Gene* 43:29-40) from *B. thuringiensis* HD-1 (pBT1-106A, disclosed by Adang et al. [1987] in *Biotechnology in Invertebrate Pathology and Cell Culture* [K. Maramorosch, ed.], pp. 85-99). The 3'-end of this gene was removed by digestion with Bal31 and a linker having the structure

```
5' TAATTGAATAGATCT 3'
   3' ATTAACTTATCTAGA
``` was ligated onto the end. This linker encoded stop codons in all three reading frames and a BglII site at its 3'-end. The resulting structural gene had 1820 bp from the 5'-end of the structural gene, encoding 607 amino acids and an extra asparagine residue, encoded by the linker at the carboxy terminus. The 3'-end of the structural gene, therefore, had the structure:

```
      IleAspArgIleGluPheValProAlaAsnEnd BglII
5'...ATAGATCGAATTGAATTTGTTCCGGCTAATTGAATAGATCT...3'
``` where the underlined sequence at the left indicates the sequence which in other experiments was shown to be insufficient to be insecticidal.

A hygromycin gene (hyg) (Gritz and Davies [1983] *Gene* 25:179-188) was modified by a G residue at position −3 relative to the translation start codon, and by insertion of a BamHI site 5' to the translational start codon. Having a G at −3 is though to enhance translational initiation in eukaryotes. This hyg gene was ligated to the BamHI site of the truncated HD-1 ("DIPEL") gene, thereby forming a DNA sequence which can encode a dicistronic mRNA, The polypeptide encoded by the truncated "DIPEL" gene was shown to be as toxic as the protein encoded by the full-length "DIPEL" gene.

13.8 Description of binary vectors. pH576 was a pH575 derivative carrying an ORF24 promoter/insecticide structural gene/ORF24 polyadenylation site combination identical to that carried by pH450.

pH577 was a pH575 derivative carrying a CaMV 19S promoter/insecticide structural gene/CaMV polyadenylation site combination, the promoter and polyadenylation site-being carried by the same fragments which contributed them to the plant-selectable kan genes of pH450 and pH575. pH577 had the same *Bacillus thuringiensis* HD-73 insecticide structural gene as pH450.

pH578 was a pH575 derivative carrying a CaMV 35S promoter/insecticide structural gene/T-DNA ORF25 polyadenylation site combination. pH578 had the same *Bacillus thuringiensis* HD-73 insecticide structural gene as pH450 and the same promoter and polyadenylation site as carried by pIC35/A.

pH582 was a pH575 derivative carrying a CaMV 35S promoter/insecticide structural gene/T-DNA ORF25 polyadenylation site combination. The promoter and polyadenylation site were the same used in pH578. The insecticide structural gene was derived from a 5.3-class gene (Kronstad and Whiteley [1986] *Gene* 43:29-40) from *B. thuringiensis* HD-1 and included about the 1.83 kbp 5' from the structural gene (pBT1-106A, disclosed by Adang et al. [1987] in *Biotechnology in Invertebrate Pathology and Cell Culture*, K. Maramorosch, ed., pp. 85-99). The portion utilized encodes essentially only the toxic region of the insecticidal protein.

pH585 was a pH575 derivative carrying an ORF24 promoter/insecticide structural gene/ORF24 polyadenylation site combination, the insecticide structural gene being the same as contained by PH582. The promoter and polyadenylation site were the same as used in pH450 and pH576.

pH591 was a pH575 derivative carrying an ORF24 promoter dicistronic gene/ORF24 polyadenylation site. The dicistronic gene was the truncated "DIPEL" structural gene/hyg structural gene combination described in Example 13.7.

pH610 was a binary vector based on a pTJS75 replicon (Klee et al. [1985] *Biotechnol.* 3:637-642), previously used herein to make pH450 and pH575. The tetracycline resistance gene (tet) of pTJS75 had been replaced with an erythromycin resistance gene (ery) derived from pR29 (Morrison et al. [1984] *J. Bacteriol.* 159:870-876). From "left" to "right," the T-DNA of pH610 consisted of a pTi15955 (number scheme as in Barker et al. [1983] *Plant Mol. Biol.* 2:334-350) fragment spanning positions 602 to 1186 and carrying the left $T_L$-DNA border repeat; a neomycin phosphotransferase I (NPT1) gene, expressed in bacteria, originally from Tn903 (excised on a 1.45 kbp BamHI fragment from pUC4K, Viera and Messing [1982] *Gene* 19:259-268), oriented to transcribe from left to right; a plant-expressible hygromycin-resistance gene, transcribed from right to left, under control of the CAMV 35S promoter and the T-DNA ORF25 polyadenylation site from pIC35/A, the hygromycin-resistant gene being derived from pLG62 (Gritz and Davies [1983] *Gene* 25:179-188); a dicistronic plant-expressible gene transcribed from right to left under control of the ORF24 promoter and either the ORF25 or ORF26 polyadenylation site (Barker et al., supra), the dicistronic gene having an insecticide structural gene from HD-1 ("DIPEL") (a 4.5 kb-class gene, Kronstad and Whiteley, supra) at its 5'-end and a NPT2 structural gene (kan) at its 3' end; and a T-DNA fragment spanning positions 12,070 to 14,710, carrying an octopine synthase gene (ocs) transcribed to the left and the right $T_L$-DNA border repeat.

pH615 was identical to pH610 with some exceptions. There was no NPT1 gene. In the plant-expressible selectable marker, a Tn5 NPT2 structural gene (the "double mutant" of Sutton et al., European Patent Publication No. 0 223 417) and an ORF26 polyadenylation site (from the same HincII fragment as contributed the ORF25 site) substituted from the hygromycin resistance structural gene and the ORF25 polyadenylation site of pH610. The plant-expressible insecticide gene was terminated by an ORF25 polyadenylation site. The insecticide structural gene was from HD-1 ("DIPEL"), and was preceded by a slightly modified alfalfa mosaic virus (AMV) RNA$_4$ 5'-leader sequence. This leader was encoded by a synthetic linker having a structure of

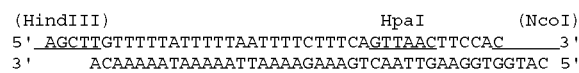

the horizontal lines indicating the location of sites recognized or partially recognized (partial recognition is indicated by parentheses) by the indicated restriction enzymes. This linker could be ligated to the HindIII site at the 3'-end of the 35S promoter, the resulting transcripts having 9 bp of the CaMV 35S transcript as its 5'-end. The NcoI sticky-end could be ligated to the 5'-end of a structural gene by use of appropriately-tailed linkers.

pH619 was essentially identical to pH615 except for the insecticide structural gene and the polyadenylation site 3' therefrom. The insecticidal structural gene of pH615 was the same as that carried by p544Pst-Met5, but lacking almost totally *Bacillus* sequences 3' from the translational stop codon. The polyadenylation site 3' from the structural gene was from T-DNA ORF25 and was carried, as described elsewhere herein, on a HincII fragment. Additionally, a TMV 5'-leader sequence (Example 13.5) was present between the 35S promoter and the p544Pst-Met5 structural gene.

pH623 was essentially identical to pH610 except for the presence of the TMV5'-leader (Example 13.5) at the 5'-end of the structural gene and for the substitution of the insecticide structural gene carried by p461/97-14 for the insecticide structural gene of pH610. The 3'-extension of the coding sequence beyond the natural position of the translational termination site did not affect toxicity of the encoded insecticidal protein.

pH624 was essentially identical to pH619 except for substitution of the insecticide/NPT2 structural gene of p461/151-174 for the insecticde structural gene of pH619.

pH627 was identical to: pH615 with the exception of the presence of an inserted phaseolin third intron in the AMV RNA$_4$ 5'-leader sequence. A fragment of a phaseolin gene, carrying the third intron and flanking coding sequences, and spanning from the XbaI site at position 904 to the Sau3AI site at position 1061 (as numbered by Slightom et al., supra). This fragment could be inserted into the HpaI site of the AMV RNA$_4$ leader linker with the aid of appropriate linkers to adapt XbaI and Sau3A sticky-ends to the blunt ends of HpaI.

13.8 Deposited strains. The following strains were deposited with the Patent Culture Collection, Northern Regional Research Center, 1815 N. University Street, Peoria, Ill. 61604:

| Strain | Deposit Date | Accession # |
|---|---|---|
| *E. coli* MC1061 (p544-HindIII) | Oct. 6, 1987 | NRRL B-18257 |
| *E. coli* MC1061 (p544Pst-Met5) | Oct. 6, 1987 | NRRL B-18258 |

The deposited strains are provided for the convenience of those in the art, and are not necessary to practice the present invention, which may be practiced with the present disclosure in combination with publicly available protocols, information, and materials. *E. coli* MC1061, a good host for plasmid transformations, was disclosed by Casadaban and Cohen (1980) *J. Mol. Biol.* 138:179-207.

Example 14

This Example teaches expression in *Zea mays* of a coleopteran-active insecticidal protein gene from *Bacillus thuringiensis* var. *tenebrionis*.

14.1 Maize protoplast transformation. A suspension culture of Black Mexican Sweet (BMS) corn cells was digested in 2% cellulase, 0.25% pectinase (both from Worthington Biochemical Corp., Freehold, N.J.), 0.2 M mannitol, and 80 mM CaCl$_2$ for about 4 hours at a concentration of about 1 g fr. wt. cells in 10 ml enzyme solution. The protoplast solution was filtered through a 46µ mesh sieve to remove undigested cell clumps. Protoplasts were obtained from 8.5 g fr. wt. of cells. After washing, the protoplasts were resuspended in MaMg (0.4 M mannitol, 15 mM MgCl$_2$, 0.1% MES, pH 5.6) at a concentration of 2.5×10$^6$ ml$^-$. Half ml aliquots of protoplasts were placed into 15 ml disposable round-bottom centrifuge tubes. Appropriate DNA solutions were added to each tube, followed by the addition of 300 µl of a 40% (w/v) polyethylene glycol (PEG) solution (avg. PEG molecular weight=6000-7500; source: EM Science, Gibbstown, N.J.; dissolved in NaMg; final pH about 6.0; filter-sterilized). DNA solutions were as follows:

| | BTT | Fusion-High | Fusion-Low | Control |
|---|---|---|---|---|
| µg p461:162-191 DNA | — | 10 | 2.5 | — |
| µg p461:151-193 DNA | 25 | — | — | — |
| µg pIC19R-35S-Kan DNA | 2.5 | — | — | — |
| µg salmon sperm carrier DNA | 22.5 | 40 | 47.5 | 50 |
| Total DNA conc. (µg/ml) | 100 | 100 | 100 | 100 |

The tubes were incubated for 30 minutes at room temperature with occasional gentle mixing. The incubations were then diluted by addition of and mixing with 1 ml of MS4D+8M (MS salts, 4 mg/l 2,4-D, 8% mannitol, 2% sucrose, 0.75 mg/l thiamine.HCl, 7.7 mg/l glycine, 1.3 mg/l nicotinic acid, 0.25 mg/l pyridoxine-HCl, 0.25 mg/l calcium pantothenate, and 1 mM asparagine). After a further 5 minutes, two further dilutions of 2 ml MS4D+8M were done at 5 minute intervals. The protoplasts were centrifuged at low speed, resuspended at a concentration of $2\times10^5$ m$^{-1}$ in CM+8% mannitol (CM=conditioned medium=filter-sterilized medium that BMS suspension cells had been growing in), poured into a 100×20 mm Petri plate, diluted with an equal volume of MS4D+8M, 2.4% SP (Sea Plaque agarose, FMC BioProducts, Rockland, Me.) at about 37° C., and swirled to evenly disperse protoplasts. After the medium had solidified, the Petri plates were sealed with parafilm, placed in plastic storage boxes, and incubated in very dim light at about 26° C.

After 12 days, 12.5 ml of MS4D+4% mannitol+100 mg/l kanamycin was added to the plates, resulting in a final selective kanamycin concentration of about 50 mg/l. Nine days later, agarose slabs containing developing protoplast-derived colonies were replated onto Gel-rite-solidified MS4D+100 mg/l kanamycin in 100×15 mm Petri plates. Kanamycin-resistant calli developed within 3 weeks from cell treatments except the "Control." The kanamycin-resistant calli were transferred individually to fresh Gel-rite solidified MS4D+100 mg/l kanamycin, and were subsequently maintained by transferring every 2 to 3 weeks onto medium of the same composition.

After selection on kanamycin, no "Control" calli remained, and three "Fusion-Low" caili, seven "Fusion-High" calli, and 169 "BTT" calli had survived.

14.2 Assay of insecticidal protein. Presence of the introduced DNA sequences was analyzed by Southern blot hybridization, using nick-translated NPT2 and insecticide gene DNA fragments (IG) as probes. Expression of the introduced genes was assayed by ELISA, using anti-NPT2 and anti-*B. thuringiensis* var. *tenebrionis* crystal protein antisera (CP). Separate tissue samples from each cell line were used for each assay. The results of the ELISA assays and Southern blots on the "Fusion" calli are summarized in Table 10.

ELISA positive were obtained only from calli whose DNA had regions of homology to both the NPT2 and IG probes. The lack of complete correspondence between the NPT2 and CP ELISAs could be due to reasons such as differential sensitivity of the assays, occasional problems with protein extraction or protein stability, or chimeric cell lines.

Twenty-eight of the 169 "BTT" calli were assayed by ELISA on two different days (separate tissue samples), using the anti-insecticidal protein antiserum. The results are shown in Table 11. Nine out of 28 (32%) of the calli tested positive in at least one of the two assays. There were only three discrepancies between the two assays (calli 6-21, 6-32, and 21-12). In each case, the callus tested positive in Experiment 1 and negative in Experiment 2. The most likely explanation is lower sensitivity of the Experiment 1 assay compared to the Experiment 2 assay.

Example 15

This Example teaches the expression in tomato (*Lycopersicum esculentum*) of the full-length *Bacillus thuringiensis* insecticide gene under control of both viral and T-DNA promoters.

15.1 Leaf tissue transformation. The leaf tissue transformation protocol combined and modified the procedures of Bevan, M. et al. (1985) *EMBO J.* 4:1921-1926, and Horsch, R. F. et al. (1985) *Science* 227:1229-1231. Leaves from three- to five-week-old greenhouse-grown seedlings were used. These leaves were washed, surface-sterilized, brushed, cut into 5 mm sections, and placed on agar-solidified regeneration medium (MS salts [Murashige, T., F. Skoog (1962) *Physiol. Plant.* 15:473-497], 30 g/l sucrose, 100 mg/l thiamine, 50 mg/l nicotinic acid, 50 mg/l pyridoxine, 5 μM zeatin riboside, 3 μM 3-indole-acetyl-DL-aspartic acid, 9 g/l agar, pH 5.65-5.8) or moistened filter paper for 1 day before bacterial inoculation. It was important to keep leaves moist. There were noticeable increases in survival with the 24-hour culture period prior to bacterial inoculation. Overnight cultures of bacteria were grown in L broth on selective antibiotics and diluted about 1/10 (an OD at 595 nm of about 250) prior to use. Bacteria were applied to each leaf disc with a sterile paintbrush and then plates were placed at 25° C. for 2-3 days. After the 2 days, leaf discs were rinsed in antibiotic-containing regeneration media and then placed on antibiotic-containing regeneration agar plates. (All plates had an antibiotic-containing medium, containing 50 mg/l cefotoxin, or 250 mg/l carbenicillin and 0.50 mg/l vancomycin.)

Leaves transformed by bacterial strains containing the kanamycin resistance genes were grown under selection pressure using three procedures (Colbere-Garapin, F. et al. [1981] *J. Mol. Biol.* 15:1-14): (1) placement of inoculated explant on antibiotic-containing medium with 20 mg/l G418; (2) placement of explants on antibiotic medium with 5 mg/l G418; and (3) placement of explants on antibiotic medium with no G418. All treatments were transferred to plates containing about 15 to 20 mg/l G418 after approximately 5-7 days. An additional transfer two weeks later helped to eliminate further escapes. Tissues were then tested for opines.

15.2 Hypocotyl transformation. The use of inverted stem segments for in vitro transformation of tobacco tissues was first developed by Braun, A. C. (1956) *Cancer Res.* 16:53-56. The key to success using this method appears to be the fact that wound cell divisions and callus formation occur at the basal end of the stem or hypocotyl segment. These divisions are important for two reasons. First, wound responses are a known requirement for transformation by *Agrobacterium tumefaciens*. Second, and more important, is that the subsequent cell divisions increase the numbers of transformed cells to a point where they can be screened for by opine analysis and survive heavy kanamycin selection pressure. The standard protocol used was to isolate hypocotyl segments (from sterile plants grown in growth incubator), to invert these so that the basal end was up, and then to inoculate with 2 μl bacteria applied with a micropipet (Pipetman). Bacteria were grown in L broth of MSSP medium supplemented with 50 μM acetosyrigone (Stachel, S. E., et al. [1985] *Nature* 318:624-629). After 1 to 2 days, the segment was washed thoroughly with liquid medium containing antibiotic and transferred to solidified antibiotic-containing medium. After visible callus was observed, it was excised, and cut into small pieces (about 3 mm) and subcultured on agar-solidified medium containing antibiotics. (These antibiotics included carbenicillin 260 mg/l and vancomycin 50 mg/l and G418 for selection pressure.) After tissues were grown to a large enough size (about 50 to 100 mg), they were subcultured and analyzed for opine content.

15.3 Transformations with *Agrobactetium* strains. Strains used for transformation of tomato were *A. tumefaciens* LBA4404 (Ooms, G. et al. [1981] *Gene* 41:33-50) containing the binary vectors pH450, pH575, pH576, pH578, pH582, and pH585. Transformations were made as described above on both leaf and hypocotyl tissues of UC82, LA14, V7 (LA14×LA159) and V7R (LA159×LA14) hybrids (carrying several marked genes in a heterozygous state), and proprietary hybrids 6-16, 6t1016, and 6t0045 M. Hypocotyl transformations generally yielded higher efficiency of transformation as detected by octopine production and kanamycin resistance. Efficiency of leaf transformations varied in the range of about 0.5% to about 5.0% depending on the particular *Agrobacterium* strains while hypocotyl transformations ranged in efficiency from about 5 to about 40% (Table 12).

Tomato plants were regenerated as described by Tatchell, S., A. Bins (1986) *Tomato Genet. Coop. Rept. No.* 36, pp. 35-36.

15.4 ELISAs. ELISA protocols were based on those described in Example 12.8. Techniques for preparing tissue samples were modified to enhance detection of insecticidal protein in plant tissues. Since in plant extracts, solubilization can be incomplete, this centrifugation step was eliminated. Leaf tissue was harvested from greenhouse plants, weighed, and placed in Eppendorf tubes on ice. Samples were quickly frozen in liquid nitrogen, thawed briefly, ground with a glass rod, and resuspended in 5×W/V PBS with 0.1 mM phenylmethylsulfonyl fluoride (PMSF). These samples are placed in the cold for about twenty minutes before taking aliquots for protein assays. Modified double antibody sandwich ELISAs with NADP-enhanced alkaline phosphatase were performed, tissue extracts containing 0.2 to 0.5 mg/ml protein (Clark, M. F., M. Bar-Joseph [1984] *Meth. Virol.* 7:51-85). Polystyrene microtiter plates were coated with mouse polyclonal antisera in 15 mM sodium carbonate buffer, 35 mM sodium bicarbonate, and pH 9.6 (0.1 ml/well) and stored at 4° C. for 1 day to 2 weeks. Between each step, plates were washed 3 times with PBS-Tween (PBS+0.05% "TWEEN"). Plates were blocked with blocking solution (PBS+"TWEEN"+1% bovine serum albumin (BSA) fraction V (Sigma) and 1% casein acid hydrolysate (Sigma)). Plates were washed again and 0.1 mlavell antigen solution was added and incubated for about 2 to 3 hours at 25° C. Primary rabbit antisera against *B. thuringiensis* insecticidal protein were added to washed plates and incubated overnight at 4° C. The following morning, plates were washed and a 1:2500 dilution of alkaline phosphatase-labeled goat anti-rabbit antibody (Kirkegaard Perry Laboratories, Inc.) was added for about 2 hours. Plates were developed with modified nicotinamide adenine dinucleotide phosphate (NADP) enhancement (Johansson, A et al. [1986] *J. Immun. Meth.* 87:7-11; Stanley, C. J. et al. [1985] *J. Immun. Meth.* 83:89-95; Self, C. H. [1985] *J. Immun. Meth.* 76:389-393). This involved addition of 0.1 ml/well of 300 mM NADP in diethanolamine substrate buffer (50 mM diethanolamine HCl pH 9.5, 1 mM $MgCl_2$) followed 25 minutes later by addition of amplifier buffer (0.05 M sodium phosphate buffer, pH 7.2, containing 5 mg/ml BSA and 4% ethanol) with 0.55 mM p-iodonitrotetrazolium (Sigma), 1.5 mg/ml "DIAPHORASE" (Boehringer Mannheim), and 2 mg/ml alcohol dehydrogenase (Sigma). The reaction was stopped by the addition of 0.2 M $H_2SO_4$. Absorbances were read at 492 nm. Alternate development used was conventional p-nitrophenyl phosphate development.

15.5 Western blots. *Bacillus thuringiensis* insecticidal protein was detected in transformed tomato plants using protein immunoblot procedures ("Westerns"). The basic protocol involved preparation of leaf tissue by freezing in liquid nitrogen, grinding with mortar and pestle, and precipitating protein with 10% trichloroacetic acid. The samples were incubated on ice for at least 30 minutes and then spun at approximately 9000 rpm for 10 minutes. The pellet was resuspended in phosphate-buffered saline (PBS: 10 mM sodium phosphate, 0.15 M NaCl, pH 7.4), and then insecticidal protein was precipitated in 20% ammonium sulfate, saturated ammonium sulfate being added slowly to samples at 4° C. Samples were then spun for 10 minutes at 9000 rpm, pellets were resuspended in modified PBS (PBS, 1% polyvinyl pyrrolidone, 0.006% 2-mercaptoethanol (2ME), 0.01% PMSF) and then dialyzed in PBS overnight at 4° C. Samples were cleared through glass wool and frozen at −20° C. in cracking buffer (5% SDS, 6 M urea, 20 mM $NaH_2PO_4$, 0.02% bromophenol blue, 20% glycerol, and 0.3% 2ME). Tissue samples were then loaded on 8.5% acrylamide stacking gel (Laemmli, U.K. [1970] *Nature* 227:680-685). The stacking gel was run at 60 volts for about 1 hour and the running gel at 120 volts for 2 hours. Proteins were transferred to nitrocellulose (BA85) in Towbin's buffer (Towbin, H. et al. [1979] *Proc. Natl. Acad. Sci. USA* 76:4350-4354) in an IDEA Scientific GENIE Blotter at about 1 A and about 24 V for about 1 to 2 hours at 4° C. The nitrocellulose Was briefly fixed in Towbin's buffer and then blocked for 1 hour at room temperature in Tris-buffered saline (TBS: 50 mM Tris-HCl, 0.15 M NaCl, pH 7.5) with 5% nonfat, dry mild (NFDM; Carnation). After blocking, it was washed 3 times (20 minutes each) with TBS+0.5% NFDM+0.5% Nonidet P-40 (detergent) before incubating overnight at 4° C. with anti-insecticidal protein antibodies. After primary antibody infection, the nitrocellulose was again washed 3 times (20 minutes each) with TBS+0.5% NFDM+0.5% sodium dodecyl sulfate (SDS). It was then incubated with goat anti-rabbit antibody alkaline phosphatase labeled (1:4000) for 2 hours at room temperature. Again, the nitrocellulose was washed for 20 minutes in TBS+0.5% NFDM+0.5% SDS, followed by 2 additional washes (10 minutes each) with TBS+0.5% NFDM+0.05% "TWEEN." The nitrocellulose was rinsed quickly three times in $MgCl_2$ buffer (0.1 M Tris HCl, pH 8.8, 0.1 M NaCl, and 5 mM $MgCl_2$) and then developed with 0.15 mg/ml 5-bromo-4-chloroinoxylphosphate/nitroblue tetrazolium substrate (Knecht, D. A., R. L. Dimond [1984] *Anal. Biochem.* 136:180-184; Blake, M. S. et al. [1984] *Anal. Biochem.* 136:175-179). Extracts of control tissues were spiked with protoxin and/or toxin during extraction to estimate recovery during the Western procedure. This showed that often insecticidal protein did not completely solubilize. As little as 0.01 ng of toxin was routinely detected on the blot. In 'spiked' samples, about 10 ng of standard was added to typical UC82 extract (from 100 mg tissue); the resultant signal on the blot represented about 30% recovery.

15.6 Bioassays. Bioassays were the most sensitive assay for the detection of *Bacillus thuringiensis* insecticidal protein. Two types of bioassays were conducted on putative transgenic plants. In the first, leaves were excised and placed in Petri plates containing moistened filter paper. A predetermined number of first instar *Manduca seta* (tobacco hornworm) larvae were then added. This assay facilitated observations on *Manduca* and enabled larger numbers of samples to be tested. Substantial differences were observed between some varieties. However, results on a given $R_0$ or $R_1$ plant were not always consistent, due to either instability or insecticidal protein in excised leaves, or possible feeding of worms on moistened filter paper. In the second type of bioassay, first instar or, preferably, neonatal hornworms just hatched from eggs (eggs from Carolina Biological Supply) were placed on plants in the greenhouse, and checked daily for growth and mortality after 7 to 9 days. Problems with this assay included worms leaving tomato plants and dying of desiccation due to high greenhouse temperatures ("wandering worms") and difficulties in finding hornworms on the tomato plants. These problems were adjusted for with control plant data, in which less than 20% mortality was consistently observed. "Wandering worms" were further controlled by placing the plants and worms in netted cages.

15.7 Nucleic acid analysis. Southern and Northern blot analyses were done using standard techniques well known to the art.

15.8 Results. $R_0$ plants were regenerated from pH450, pH576, pH577, pH578, pH582, and pH585 transformations and $R_1$ plants from pH450, pH576, and pH578 transformations (see Table 13). Kanamycin-resistant tissues were obtained from all transformations. Bud initials existed on transformations of most vectors (Table 12). $R_0$ plants from both pH578 and pH577 transformations that have been selected on 40 mg/l geneticin (equivalent to 400 mg/l kanamycin) gave high octopine signals.

Initially, many $R_0$ plants from transformations with pH450 were infertile due to long-term tissue culture. This was evident from increased flowering, and fruit set was observed in $R_0$ plants from pH578 and pH577 transformations, which were cultured for less time. In addition, cuttings from some older $R_0$ plants from pH450 transformations also showed improved fruit set. This improvement may also be in response to improved greenhouse conditions.

Two independent pH450 hypocotyl transformants yielded octopine-positive, G418-resistant tissues that regenerated plants containing octopine and *B. thuringiensis* insecticidal protein. Results from ELISA assays indicated insecticidal protein at levels ranging from 0.6 µg/ml to 2.1 µg/g total protein. A substantial decrease in both total protein in the leaf and in insecticidal protein (µg/g total protein) was associated with plant age. Substantial degradation occurred, and in Western blots all ELISA-positive samples show smearing starting at about 110 kD.

ELISAs were used to screen putative transformants for high expression of *Bacillus thuringiensis* insecticidal protein. Detectable levels (greater than 5 ng insecticidal protein per g leaf tissue) were observed in transformed plants from pH450, pH577, and pH578, and in $R_1$ plants of pH577 and pH582 transformations. All ELISA-positive plants tested killed some *Manduca sexta* larvae in bioassays (Table 13).

Western blots were used to determine the form of insecticidal protein expressed (protoxin or toxin) and to quantify the level of expression more precisely. In pH450 transformants, which contain the full-length *Bacillus thuringiensis* insecticidal protein structural gene, both protoxin and toxin were observed in leaf tissues. Tissues from pH577 and pH578 transformed plants also had both forms of the insecticidal protein. Different forms of insecticidal protein (protoxin and toxin) were also observed in different regenerated plants from what initially appeared to be a single transformation event.

Results for many of the plants assayed by bioassay are listed in Table 13. Further analysis (not shown) by analysis of variance (ANOV) and Duncan's multiple range test showed significant differences at the 1% level. Transformed plants from pH450 and pH577 gave the best biological activity. Decreases in biological activity of transformed plants as a function of plant and leaf age were also observed. Control plants (UC82 Ro plants and UC82 plants grown from seed) all gave low rates of mortality (less than 25%). It was significant that on several of the $R_1$ plants with lower *Manduca* mortality, the worm weights were significantly lower than controls. In addition, *M. sexta* larvae that failed to die immediately on *B. thuringiensis* insecticidal protein-containing plants also failed to grow at normal growth rates. These differences were clearly apparent after 2 weeks.

Southern analysis showed that insertions of T-DNA containing the plant-expressible insecticide gene were present in the expected organization, and are usually present in low copy number (about 1 to 2 copies/haploid genome). In all plants positive for protein and in bioassay positive plants tested, insecticidal protein sequences were observed in Northern blots of polyadenylated RNA. However, most of this RNA was shorter than expected.

The $R_0$ regenerated plants transformed by pH450 were marginally fertile. Southern, Northern, octopine (Aeerts, M. et al. [1979] *Plant Sci. Lett.* 17:43-50), and protein analysis indicated that the insecticide gene and flanking vector sequences were inherited in Mendelian fashion. Moreover, $R_1$ progeny plants gave positive results in bioassay, demonstrating that the capacity of the transformed plants to affect *Manduca sexta* is not restricted to regenerated plants.

Both bioassays and ELISAs of kanamycin-resistant pH577 and pH578 transformants indicated presence of insecticidal protein (Table 11). The pH578 regenerates were clearly transgenic plants, as indicated by octopine assays as well as kanamycin or G418 resistance. However, the inability to detect insecticidal protein in some transformants could be due to several reasons, e.g., a lack of assay sensitivity.

Example 16

Potato Transformation Procedure 16.1 Plant material. Virus-free in vitro potato (*Solanum tuberosum*) plantlets of cultivars Kennebec, Superior, Atlantic, centennial Russet and Russet Norkotah were obtained from the University of Wisconsin, Department of Plant Pathology, Madison, Wis. Russet Burbank Virus-free plantlets were obtained from the Potato Virus Research Laboratory at Colorado State University, Ft. Collins, Colo. Hybrid Homestead seeds were purchased from Park Seed Company, Greenwood, S.C. Russet Norkotah tubers were purchased from Deircks and Sons Inc., White Lake, Wis.

16.2 Bacterial strains. *Agrobacterium tumefaciens* LBA4404, EHA101s, and Z707s strains were used for potato tissue infection. Gene constructs in these strains were pH615, pH619, pH623, pH624, and pH627. Bacteria was grown on YEP media with 250 mg/l streptomycin and 200 mg/l erythromycin for 24 hours at 28° C. then suspended in MS liquid media prior to tissue inoculation.

16.3 Tissue culture media. Shoot induction medium consisted of MS salts (Murashige and Skoog, supra), 1.0 mg/l thiamine, 0.5 mg/l nicotinic acid, 0.5 mg/l pyridoxine, 100 mg/l myo-inositol and 3% sucrose supplemented with 0.87 mg/l IAA aspartic acid (Research Organics) and 1.76 mg/l zeatin riboside (Sigma). Hormones were added prior to autoclaving. The pH was adjusted to 5.8 with 0.1 M KOH and the medium was solidified with 7 g/l Tonomeko agar. Shoot induction medium containing carbenicillin at 500 mg/l and kanamycin at 25 mg/A was used for selection of transformed shoots. Stock plantlets were grown on MS basal medium without hormones in magenta GA7 containers (Magenta Corp.) and subcultured every 4 weeks. Shoot elongation and rooting medium consisted of MS basal medium with 25 mg/l kanamycin.

16.4 Procedure. Both stem and tuber tissue were used for transformation. Tubers were peeled and surface-sterilized in 10% liquid bleach for 15 minutes under constant agitation. A 0.7 cm diameter cork borer was used to make cores through the tuber. These cores were then sectioned into 2 to 3 mm thick discs and then inoculated (Sheerman, S., M. B. Bevan [1988] *Plant Cell Rep.* 7:13-16). Stem sections approximately 0.5 cm were made from in vitro grown stock plants 2 to 3 weeks after subculture. All sections containing axiliary buds were discarded. Stem or tuber tissues were immediately soaked in $10^6$, $10^7$, or $10^8$ ml$^{-1}$ *Agrobacterium tumefaciens* cells for 5 to 10 minutes. They were then placed on sterile filter paper discs over *Nicotiana tabacum* feeder layers (Horsch, R. B. et al. [1985] *Science* 227:1229-1231) over shoot induction medium without antibiotics. They were cocultivated for 2 days then rinsed in liquid MS media containing 500 mg/l carbenicllin, blotted on sterile cardboard, and transferred to shoot induction media with carbenicillin 500 mg/l. After 4 to 5 days the stem segments or tuber discs were placed on shoot induction media containing 25 mg/l kanamycin and 500 mg/l carbenicillin. Cultures were transferred every 3 weeks. Buds began to appear in 4 to 6 weeks and continued to form for several weeks thereafter. Shoots were excised and rooted on MS media with 25 mg/l kanamycin, then tested for gene expression.

16.5 Results. Thirty-three Russet Burbank plants regenerated from tissues inoculated with *A. tumefaciens* (pH615) were selected on 25 mg/l kanamycin. Three of these plants were tested for expression of *B. thuringiensis* insecticidal protein by ELISA; two were negative and one was positive. The insecticidal protein was expressed at a level of 5 ng/mg total protein. This plant also tested positive for NPT2 by ELISA. The plant DNA was then assayed by Southern analysis and tested positive for both insecticidal protein and NPT2. The DNA was also probed with a small section of the bacterial DNA (vir) to test for *Agrobacterium* contamination; none was present. A total of 7 Hybrid Homestead plants resulting from inoculations with pH624 and 4 Russet Burbank plants from inoculations with the pH627 have now been selected on kanamycin. Nine Kennebec plants regenerated after inoculations with the pH623 construct have also been selected.

Example 17

Cotton Transformation

*Agrobacterium tumefaciens* strain LBA4404 (Hoekema, A. et al. [1983] *Nature* 303:179-180) carrying a binary vector (either pH576, pH577, pH578, pH582, or pH585) was cultured on YEP (10 m/l yeast extract, 10 g/l peptone, 5 g/l NaCl) medium containing 250 µg/ml streptomycin and 25 µg/ml kanamycin (both from Sigma) for selection and solidified with agar. Bacteria were scraped off the agar medium, suspended in a $G_2$ medium (MS salts (Bibco); Murashige and Skoog, supra, 100 mg/l myo-inositol, 0.4 mg/l thiamine.HCl, 5 mg/l 2iP, 0.1 mg/l NAA (all from Sigma), 30 g/l glucose, pH 5.9) to a concentration of about $10^8$ cells/ml and were used for inoculation of cotyledon segments.

Cotton was transformed essentially as disclosed by Firoozabody, E. et al. (1987) *Plant Mol. Biol.* 10:105-116, and Firoozabady, E. U.S. patent application Ser. No. 07/076, 339, filed Jun. 22, 1987, now abandoned. The Firoozabady application reads, in pertinent part: Cotton (genus *Gossypium*) is an important commercial crop. Fiber-producing members of this genus are *G. arboreum*, G. herbaceum, *G. hirsutum, G. barbadense, G. lanceolatum*, all the foregoing being cultivated species, and *G. tomentosum, G. mustelinum* and *G. darwini* which are wild-type species. "Cotton," R. J. Kohel et al. eds. (1984), American Society of Agronomy, Inc., p. 52. In the United States, *G. hirsutum* is the major cultivated species. A number of different varieties are cultivated in different parts of the country, classified into Acala, Delta, Plains and Eastern. The Acala varieties grown in the Southwest are predominantly Acala 17's, and in California are the SJ series. Delta varieties include Stoneville and Deltapine. Plains varieties include Lankart and Paymaster, and Eastern varieties include Coker and McNair. Cotton, supra, p. 203-205. Southwestern varieties also include the GSA varieties.

Despite success in regenerating a number of plants such as tobacco and petunia, investigators have had substantial difficulties with regeneration of cotton (*Gossypium hirsutum* L.). Methods of regenerating this valuable crop plant from somatic tissue are desirable so as to enable transformation of cotton with foreign DNA conveying valuable agronomic traits. Limited success has been obtained in the regeneration of easily regenerable Class 1 genotypes of cotton such as the Coker varieties grown primarily in the eastern United States, but to date no methods have been available for the regeneration and transformation of Class 2 agronomic genotypes such as those of the Acala, Delta and Plains types which make up the important crop varieties of the remainder of the United States. The methods by which this invention achieves regeneration involve adjustments of auxin/cytokinin ratios in somatic embryogenesis induction media. No prior disclosures teach or suggest such adjustments for the regeneration of any variety of cotton.

A practical, reproducible, efficient method for regenerating fiber-producing species of cotton as provided herein is useful in rapid multiplication of plants produced by conventional breeding methods and in genetic engineering of plants wherein foreign genes are introduced into plant cells and the cells are regenerated to form whole fertile plants.

Ammirato, P. V. (1983) "Embryogenesis," in Handbook of Plant Cell Culture, Evans, D. A., et al., eds. 1:82-123 provides a general discussion of somatic embryogenesis as a method of plant regeneration. This article at page 84 describes the basic somatic embryogenesis protocol as involving a primary medium with an auxin source and a second medium devoid of growth regulators. During the primary culture the tissue underwent differentiation to produce a mass of unorganized cells and cell clusters, and transfer to a second medium prompted either initiation of embryonic development, or as it was later thought, embryo maturation. At page 99, auxins or auxins in combination with cytokinins are said to be essential to the onset of growth and the induction of embryogenesis. At page 100, cytokinins are characterized as important in fostering somatic embryo maturation and cotyledon development. This article indicates that embryogenesis protocols have a high degree of specificity for the type of plant being regenerated. No reports of cotton regeneration are described in this article, nor is a callus initiation medium having a high cytokinin/auxin ratio followed by an embryo induction medium having a high auxin/cytokinin ratio as used in this invention suggested or disclosed.

The only prior report of cotton transformation producing whole plants known to applicant is disclosed by P. Umbeck, et al. (1987), in "Genetically Transformed Cotton (*Gossypium hirsutum* L.) Plants," Bio/Technology 5:263-266, describing regeneration of Coker varieties 310, 312 and 5110 from hypocotyl sections transformed with a kanamycin resistance gene (nptII) and a chloramphenicol acetyltransferase (cat) gene. After incubation with *Agrobacteria*, the hypocotyl sections were placed on a medium containing equal amounts of auxin and cytokinin (0.1 µg/ml each of 2,4-dichlorophenoxyacetic acid (2,4-D) and 6-furfurylaminopurine (kinetin) as well as 5-50 µg/ml kanamycin sulfate. After tissue amplification, embryogenic tissues were transferred to a regeneration medium without phytohormones. Mature embryos (4 mm or more with cotyledon and radicle structures) were transferred to Stewart and Hsu medium (J. Stewart et al. (1977), "In-ovulo embryo culture and seedling development of cotton (*Gossypium hirsutum* L.)" *Planta* 137:113-117) with indole acetic acid (IAA), 6-benzylaminopurine (BA) and gibberellic acid (GA) all at 0.1 µg/ml. Tissue incubation was done at 30 degrees C. No regeneration of genotypes other than Coker was reported. This article characterizes the inability to regenerate plants as a major obstacle to practical application of transformation techniques. The discussion of this article does not constitute any representation that it constitutes prior art which may be properly applied against the claims hereof.

Prior reports of cotton regeneration include the following:

J. Stewart et al. (1977) supra, disclose the culture of zygotic embryos of *Gossypium hirsutum* L. cv. Hancock on the high-salt media BT and BTP (the latter containing phytohormones) of C. A. Beasley, et al. (1973) *Amer. J. Bot.* 60:130 modified by the addition of ammonium ion. No regeneration from somatic tissue was reported.

The first report of regeneration of a domestic cotton variety was that of G. H. Davidonis, et al. (1983), "Plant Regeneration from Callus Tissue of *Gossypium hirsutum* L.," Plant Science Letters 32:89-93, reporting the regeneration of plants from Coker 310 genotype callus derived from culture of seedling cotyledon. Callus initiation was done on LS medium (E. M. Linsmaier et al. (1965) Physiol. Plant., 18:100) containing 2 mg/l α-naphthalene acetic acid (NAA) and 1 mg/l kinetin. After three months callus tissue was subcultured on modified LS medium containing 30 g/l glucose, 1 mg/l NAA and 0.5 mg/l kinetin. Over a three-year period a few pro-embryoids were formed. This article reports increased embryogenic potential of callus tissue after growth on media without hormones, and that embryoid growth was slower in media lacking hormones than containing NAA and kinetin. The three-year embryo induction period and low efficiency of embryo formation indicate that this article is describing an adventitious observation. This article does not provide a teaching or protocol enabling practical, usable somatic embryogenesis and regeneration of cotton and discusses only the Coker 310 genotype.

Prior difficulties in regeneration of cotton varieties other than Coker are illustrated by the disclosure of R. C. Shoemaker, et al. (1986), "Characterization of somatic embryogenesis and plant regeneration in cotton (*Gossypium hirsutum* L.)," Plant Cell Reports 3:178-181. This article reports evaluation of seventeen cultivars on three callus initiation and three callus maintenance media. Seedling hypocotyl sections were used. The best initiation medium was a medium containing MS salts with 2 mg/l indole-3-acetic acid (IAA), and 1 mg/l kinetin. The best maintenance medium was one containing MS salts with 10 mg/l N6-(isopentenyl)-adenine (2iP) and 1 mg/l NAA. This medium produced the most vigorous and healthy calli but was not embryogenic. The maintenance medium was found not to be necessary for induction of embryogenic callus, and callus was initiated directly on MS medium with 3% glucose and 2 mg/l NAA and 1 mg/l kinetin, then switched to the same medium using 3% sucrose instead of 3% glucose for induction. Only Coker 201 and 315 varieties could be regenerated.

H. J. Price, et al. (1979), "Somatic Embryogenesis in Suspension Cultures of *Gossypium klotzchianum* Anderss," *Planta* 145:305-307, purports to comprise the first report of reproducible somatic embryogenesis in a species of the genus *Gossypium*. The species, however, is a wild-type, nonfiber-producing species rather than a domestic cotton species. The explants used were seedling hypocotyls. The use of a "pre-culture" containing a high cytokinin concentration (2iP($N^6$-(2-isopentyl)-adenine) at a concentration of 10 mg/l was disclosed as useful prior to making a suspension culture of the callus in media containing 0.1 mg/l 2,4-D and 20 g/l sucrose, but no cytokinin. This "pre-culture" was done following culture on an MS medium containing 2.0 mg/l IAA, and 1.0 mg/l kinetin. It was found that it was essential to somatic embryo formation that after suspension culture, the cells be transferred to a B5 medium containing glutamine (a medium also containing 0.5 mg/l 2,4-D was used), and that when the "pre-culture" with high 2-iP was not used prior to the suspension culture somatic embryos did not form. The authors stated that further testing would be required to determine if other cytokinins than 2-iP or lower concentrations would be effective in "pre-cultures". This article does not disclose the regeneration of domestic varieties of cotton, nor does it disclose a protocol involving a high cytokinin/auxin callus initiation medium followed by a high auxin/cytokinin embryo induction medium.

J. J. Finer et al. (1984), "Initiation of callus and somatic embryos from explants of mature cotton (*Gossypium klotzchianum* Anderss," Plant Cell Reports 3:41-43 describes unsuccessful attempts to regenerate plants from embryos produced from stem and petiole sections of the above wild species. High 2iP media were used followed by suspension culture in a medium containing glutamine and 2,4-D in which embryos were induced. Embryo development took place in auxin-free media. Embryos were abnormal, and efficiencies were low.

R. H. Smith, et al. (1977), "Defined Conditions for the Initiation and Growth of Cotton Callus in Vitro In *Gossypium arboreum*," In Vitro 13:329-334 describes nutrient media useful for callus proliferation and subsequent growth of subcultures. Seedling hypocotyl explants were found superior to cotyledon or leaf explants. MS media containing IAA (2 mg/l) and kinetin (1 mg/l) were found best of the combinations of auxins and cytokinins tested for callus proliferation, and media containing 2 mg/l NAA and 0.5 mg/l BA, or 1 mg/l NAA and 5-10 mg/l 2iP were found to be best for subculture. The authors report one adventitious case of plantlet regeneration (no further details available) which they did not pursue. This disclosure was not directed to somatic embryo production.

Reproducible regeneration protocols with respect to fiber-producing cotton species have thus been limited to Coker varieties of *G. hirsutum*.

T. L. Reynolds (1986), "Somatic Embryogenesis and Organogenesis from Callus Cultures of *Solanum Carolinense*," Amer. J. Bot. 73:914-918 describes culture of stem segments of a species of horse-nettle on a medium supplemented with 10 mg/l 2,4-D and 1 mg/l kinetin for callus initiation, with subculture on a medium lacking 2,4-D but containing a cytokinin for embryo production and regeneration. These protocols directly teach against the protocols used by applicant herein involving a callus initiation medium having a high cytokinin/auxin ratio and an embryo induction medium having a high auxin/cytokinin ratio.

Applicant co-authored a poster displayed at a conference at the University of California at Davis, Calif. Aug. 24-29, 1986 on "Tailoring Genes for Crop Improvement" entitled "Transformation and Regeneration of Cotton, *Gossypium hirsutum* L." This poster described transformation and regeneration of cotton.

In a nonenabling abstract for the Thirty-eighth Annual Meeting of the Tissue Culture Association held May 27-30, 1987, entitled "Transformation of Cotton (*Gossypium hirsutum* L.) by *Agrobacterium tumefaciens* and Regeneration of Transgenic Plants," applicant and others report transformation and regeneration of cotton. An oral presentation on the subject was made by applicant.

Zhou, G.-Y. et al. (1983), "Introduction of Exogenous DNA into Cotton Embryos," Meth. Enzymol. 101:433-481 discloses a method for injection of DNA from *G. barbadense* into *G. hirsutum* ovaries. Mutations were observed in progeny, however, this method does not allow for the transformation of plants with selected foreign genes governing particular desired traits as do the methods of this invention.

Figure 4:
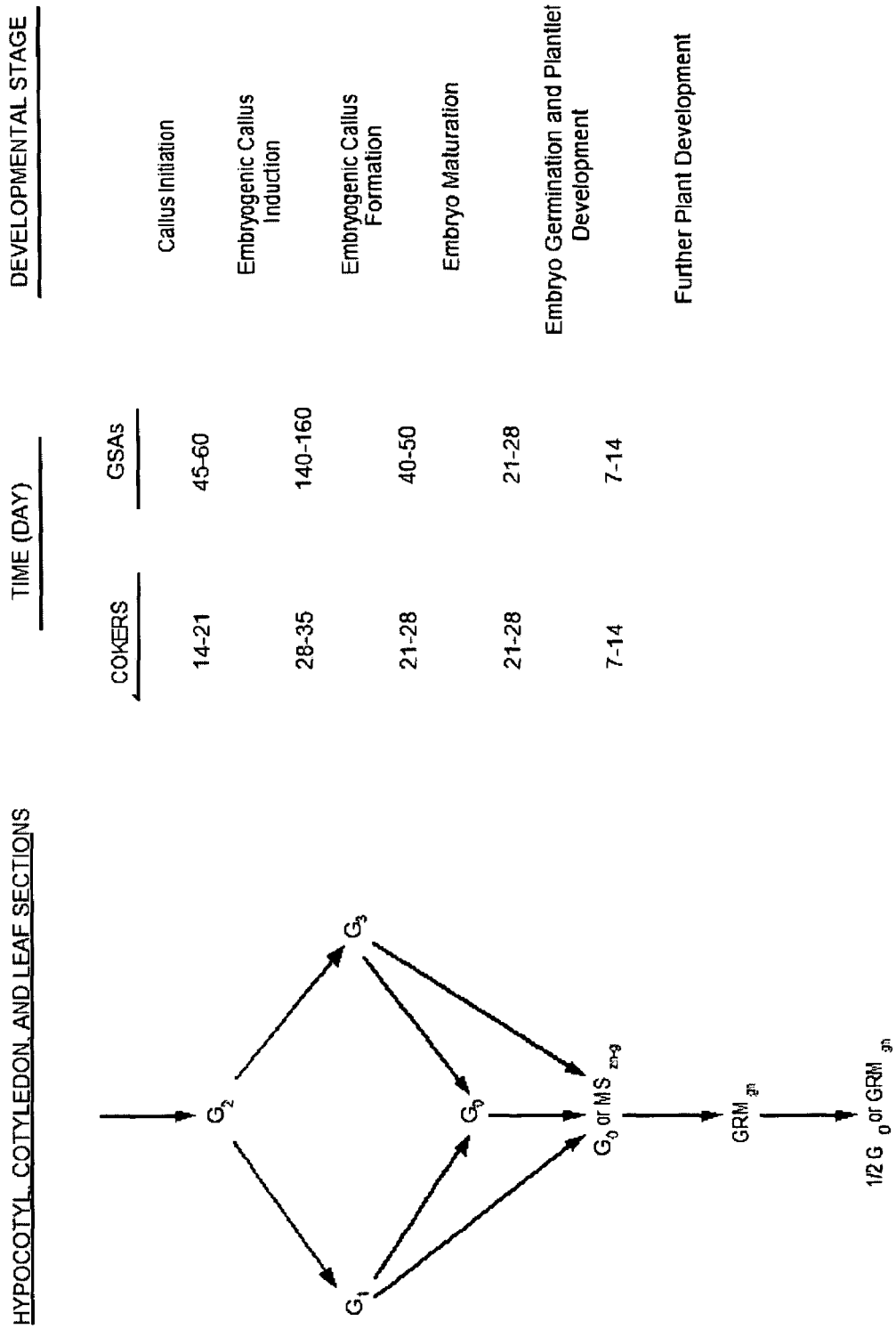
FIG. 4 is a diagram illustrating a regeneration scheme for cotton of this invention.

FIG. 4 is a diagram illustrating a regeneration scheme for cotton of this invention. The abbreviations G0 through G3' $MS_{zn-g}$, $1/2G_0$ and $GRM_{gn}$ are described in Table 14 hereof.

A process is provided for regenerating a whole plant of the genus *Gossypium*. Preferably the plant is of a fiber-producing species selected from the group consisting of *G. arboreum, G. herbaceum, G. hirsutum, G. barbadense, G. lanceolatum, G. tomentosum, G. mustelinum*, and *G. darwini*. More preferably, the species is a cultivated fiber-producing species selected from the group consisting of the first five above-named species. Of these, *G. hirsutum* is the most useful for cultivation in the United States and regeneration of this species is a preferred embodiment of this invention.

As discussed above, the Coker varieties in general, and in particular, Cokers 310,312, 5110, 201, and 315 are regenerable by means of prior art techniques, i.e. the use of a primary medium for callus initiation containing low concentrations of auxins (0.1 mg/l to 10 mg/l and equal or lower concentrations of cytokinin, and a secondary medium containing the same hormones or no hormones for embryo induction or maturation). Other varieties of *G. hirsutum* were not responsive to these techniques. Easily regenerable varieties such as Coker are termed "Class 1 varieties" herein. A "Class 1 variety" is one regenerable by means of a basic somatic embryogenesis protocol as described by Ammirato, P. V., supra involving a primary medium with an auxin source and a secondary medium devoid of growth regulator or having cytokinins. Class 1 varieties respond to the callus initiation, embryogenic callus induction and embryogenic callus formation steps of the protocol of this invention much sooner than other, more hard to regenerate cotton varieties which are designated as "Class 2 varieties". Class 2 varieties are not regenerable by prior art methods and respond more slowly to the protocol of this invention than Class 1 varieties, all as described below.

Tissue from the plant to be regenerated is first placed on a callus initiation medium. Tissue explants useful in practicing this invention include hypocotyl, cotyledon and leaf sections, preferably taken from precociously germinated seedlings. Hypocotyl segments were especially useful in obtaining regeneration of Class 2 varieties; however, cotyledon sections are also useful. Immature embryos, or portions thereof may also be used. Immature embryos are fully developed but not yet hardened.

The preferred embodiment of this invention involves the use of a callus initiation medium having a high cytokinin to auxin ratio to proliferate callus. A number of cytokinins are well known to the art, and more fully described below. The most preferred cytokinin of this invention is 2iP. Auxins are well known to the skilled worker and described in the prior art as well. The preferred auxin for use in this invention is NAA. A high cytokinin auxin ratio is defined herein to be greater than about 10:1; preferably the ratio is at least about 30:1 to 50:1 and can be as high as 100:1. The cytokinin concentration may be as high as about 10 mg/l, but not less than about 1 mg/l, and the auxin concentration should not be more than about 1 mg/l and may be as low as about 0.01 mg/l.

The callus initiation culture is continued until the callus has proliferated to about 5-10 times its original size, and until the calli are sufficiently mature that the auxins will not be toxic to the cells, generally about two to three weeks for the Class 1 varieties and about four to five weeks for the Class 2 varieties.

After the callus initiation step, the callus is transferred to an embryogenic callus induction medium having high auxin to cytokinin ratio. A "high" ratio of auxin to cytokinin for this purpose is defined as being at least about 1:1. Preferably this ratio is at least about 3:1 and more preferably about 50:1 to about 100:1. The auxin concentration should not be more than about 5 mg/l or less than about 1 mg/l, and the cytokinin concentration should not be more than about 1 mg/l and can be as low as 0.0 mg/l. The tissues are maintained on this medium until embryogenic callus is induced, characterized by production of proembryoids having globular and heart-shaped structures—generally about two to three weeks for Class 1 varieties and about five to six months for Class 2 varieties.

The calli are then transferred to suitable media for embryogenic callus formation, embryo maturation, embryo germination, and plant regeneration.

In a preferred embodiment of this invention utilizing the above preferred protocol, the regenerated plant is a Class 2 cultivar.

Also in a preferred embodiment of this invention, following the embryogenic callus induction stage, the calli are transferred to an embryogenic callus formation medium without phytohormones for maximum embryogenic callus production.

Culturing on the hormone-free medium is preferably continued until embryo maturation occurs, i.e. somatic embryos have a pair of cotyledons, green color and are about three to about 12 mm in size. The calli can be maintained on this medium for as long as desired. Preferably, however, after about three to four weeks for Class 1 varieties and about six to seven weeks for Class 2 varieties, the calli are transferred to a new medium for another two to three weeks. This new medium is preferably hormone-free medium, but optionally, may be medium containing small amounts of auxin, preferably NAA at about 0.1 mg/l, a cytokinin, preferably zeatin at about 1 mg/l, and reduced carbohydrate concentration, preferably about 1.5% glucose. The preferred hormonal medium for this purpose is $MS_{zn-g}$ as shown in Table 14.

Embryo germination media for use following the embryo maturation step described above are known to the art. A preferred embryo germination medium is a low ionic strength medium such as Stewart and Hsu medium without the added ammonium. Preferably this medium is supplemented with a gibberellin and an auxin, preferably about 0.1 mg/l gibberellic acid and about 0.01 mg/l NAA, and preferably glucose (0.5%) is used instead of sucrose.

As shown in FIG. 4, in a preferred embodiment hereof, after about two to three weeks on the preferred embryo germination and plantlet development medium, $GRM_gn$, the plantlet is transferred to a plant development medium such as a phytohormone-free medium containing reduced salts and carbohydrate (preferably about ½ MS salts and about 1.5% glucose) or culture may be renewed on a germination medium, preferably GRMg.

Growth to a whole fertile plant is continued under greenhouse conditions.

The regeneration protocol provided herein is particularly valuable for use in genetic engineering to produce whole, fertile transformed cotton plants. Transformation (incorporation of foreign DNA into the plant genome) may be accomplished by any means known to the art, preferably by infection with *Agrobacterium tumefaciens* containing the desired foreign DNA. The transformed tissues are cultured as above for regeneration into whole plants. "Foreign" refers to any DNA or genes which do not occur naturally at their new location in the host plant's genome. Foreign genes may be genes with their own promoters or chimeric genes derived from *Gossypium* or other organisms. Preferably, the foreign DNA or genes confer an identifiable phenotype on the regenerated host plant and/or its progeny by which the plant is distinguishable from naturally occurring plants. Such phenotypes conferred by foreign DNA include performance on laboratory tests such as Southern, northern and western blot procedures. Also preferably the transformation method allows for the insertion of selected genes or DNA into the cotton genome. A "selected gene" is a gene governing a particular trait which it is desired to confer on the recipient plant (as distinguished from unselected genes which may be transferred by methods such as injection of DNA extracted from other organisms and containing an unknown type and quantity of genes). Other types of "selected" foreign DNA might be particular isolated promoters or enhancers transferred to the recipient genome to perform their known functions.

By means of this invention, whole transformed cotton plants, preferably Class 2 varieties, are obtained which can express the foreign DNA or genes contained therein, e.g. foreign promoters and enhancers can be expressed to operate to turn on or enhance the activities of other genes, and foreign genes can be expressed to produce RNA and protein.

By means of this invention a regenerated plant preferably of a Class 2 *Gossypium* genotype transformed to contain foreign DNA and having a phenotype conferred by said foreign DNA by which said plant can be distinguished from a natural occurring plant is produced. Progeny of these plants may also be produced, as well as seeds of said plants and progeny plants. Any plant produced by the methods of this invention which is not phenotypically distinguishable from a naturally-occurring plant, is nevertheless considered to be within the scope of equivalents of plants claimed herein which are phenotypically distinguishable.

This invention has provided an important improvement in methods for regenerating cotton plants, which methods involve culturing somatic tissue of said plants on suitable media to cause callus formation and whole plant regeneration, the improvement of this invention comprising using somatic tissue of a Class 2 genotype of a *Gossypium* species.

Cotton Regeneration Example

Tissue from a plant of genus *Gossypium*, preferably a fiber-producing species thereof, and more preferably, a species of *G. hirsutum*, is regenerated to produce a whole plant. In the preferred embodiment hereof, the genotype used is a Class 2, difficult-to-regenerate genotype, preferably a genotype of *G. hirsutum*, and more preferably a GSA genotype.

The tissue is preferably obtained from seedlings about seven to about 10 days old, and preferably the seedlings are grown from immature seeds taken from cotton bolls which are about three to about five centimeters in diameter, about 40 to about 60 days after pollination. Incubation procedures for growing up seedlings are known to the art, for example as described in Firoozabady, E., et al. (1986), IC "Isolation, Culture, and Cell Division in Cotyledon Protoplasts of Cotton (*Gossypium hirsutum* and *G. barbadense*)," Plant Cell Rep. 5:127-131. The medium used for production of seedlings is preferably a G0 medium not containing hormones as described in the Cotton Regeneration and Transformation Examples hereof.

The explants used for tissue culture are preferably cotyledon pieces, preferably approximately 0.6 $cm^2$ in surface area, or hypocotyl sections, preferably about 5-8 mm in length, or leaf pieces approximately 0.6 $cm^2$ in surface area, taken from seedlings. These explants are taken when the seedlings are large enough to provide tissue of sufficient size, and preferably the seedlings are approximately three weeks old when the explants are taken.

Seedlings may be grown from immature seeds or germinated by culturing dry seeds. Tissue from immature (fully developed but not hardened) embryos may also be used.

The initial culture medium (callus initiation medium) is a medium containing a high cytokinin/auxin ratio. The cytokinin concentration must not be so high that it is toxic to plant cells, but must be sufficiently high that it stimulates growth of plant cells, and the auxin concentration must not be so high that it is toxic, but must be sufficiently high that it induces cell proliferation. Preferably the cytokinin concentration is between about 1.0 and about 10.0 mg/l, and more preferably between about 3 and about 5 mg/l. The auxin concentration is preferably between about 1 and about 0.01 mg/l, and more preferably between about 0.1 and about 0.2 mg/l. The cytokinin to auxin ratio is preferably between about 10:1 and about 100:1, and more preferably between about 30:1 and about 50:1. The most preferred callus initiation medium is the $G_2$ medium described in Table 14 containing mg/l 2iP and 0.1 mg/l NAA along with MS salts (Gibco, Grand Island, N.Y.), and glucose at 3.0% (w/v), along with 100 mg/l myo-inositol, 0.4 mg/l thiamine HCl, 0.2% Gel-rite (Kelco, San Diego, Calif.), at pH 5.9. As will be understood by those skilled in the art, other basal media and carbohydrate sources may be substituted for those specifically described herein. Other basal media known to the art as useful for regeneration are SL, V5 and L2. Preferably the auxin is from the NAA family, defined herein to include IAA (indole-3-acetic acid), IBA (indole-3-butyric acid), and NAA (alpha-naphthaleneacetic acid). Other auxins known to the art are 2,4-D and related auxins of the 2,4-D family, defined herein to include 2,4-D (2,4-dichlorophenoxyacetic acid), Picloram (4,amino-3,5-6-trichloropicolinic acid), pCPA (parachlorophenoxyacetic acid), 2,4,5-T(2,4,5-trichlorophenoxyacetic acid), and Dicamba (2-methoxy,3-6-dichloro-o-anisic acid). Many cytokinins are known to the art. Examples of useful cytokinins are ADE (adenine sulfate), kinetin (6-furfurylaminopurine), BA (6-benzylaminopurine), and zeatin. Concentrations of 2,4-D higher than about 0.1 mg/l, however, have been found to be toxic to cotton cells, and 2,4-D is thus not a preferred auxin.

This initial high cytokinin culture is essential to achieving the efficiency of embryo induction in later culture stages required for a practical cotton regeneration method.

The callus produced on the callus initiation medium should be midfriable, rather than extremely hard (nonfriable) or extremely friable, as midfriable callus gives the best production of embryogenic callus in subsequent culture steps.

For callus initiation, a high temperature, preferably around 30° C. is preferred, but is not critical. Light intensity during this phase of regeneration does not appear to be critical, and may vary from complete darkness up to high intensities, such as 90 µE/m²/s.

After about two to about three weeks of callus initiation for Class 1 varieties (e.g. Cokers), or about seven to about nine weeks for Class 2 varieties (e.g. GSA'S), the calli are transferred to an embryogenic callus induction medium. This step is essential for regeneration of Class 2 varieties but may be omitted for Class 1 varieties. This medium contains a high auxin/cytokinin ratio. The auxin concentration should be high enough so that it stimulates the process of embryogenesis, but not so high that it is toxic to plant cells; preferably the auxin concentration is between about 1 and about 5 mg/l, and more preferably between about 3 and about 5 mg/l. The cytokinin concentration should be high enough so that it induces embryogenesis, but not so high that it prevents embryogenesis. Preferably the cytokinin concentration is between about 0 and about 1 mg/l and more preferably between about 0.05 and about 0.1 mg/l. In the preferred embodiment described in the Example, media containing NAA at 5 mg/l and 2iP at either 1 or 0.1 mg/l, and also containing the additional components described above in connection with the $G_2$ medium are used. These two media are respectively $G_1$ and $G_3$. Again, as will be understood by those skilled in the art, equivalent components may be used, but it is necessary to maintain a high auxin/cytokinin ratio in this medium. Glucose is the preferred carbohydrate for use in the embryogenic callus induction medium, as well as for all the culture media used in this invention, as sucrose promotes production of phenolics and calli cultured on this medium have been observed to turn brown, and eventually to die. $G_3$, described in Table 14, is the preferred embryogenic callus induction medium.

Embryogenic callus formation may be observed on the embryogenic callus induction medium when the culture is kept on the medium long enough to exhaust the hormones. Preferably, however, the callus is transferred to hormone-free medium for embryogenic callus formation.

In the preferred embodiment after about three to four weeks on the embryogenic induction medium for the Class 1 genotypes, or about four to five months for the Class 2 genotypes, the callus is transferred to a phytohormone-free medium for embryogenic callus formation. Stages of somatic embryo development are well defined in the art, e.g. by Shoemaker, R. C., et al. (1986), supra, and Finer, J. J., et al. (1984), supra. Immature somatic embryos lack well defined organs, whereas normal, mature somatic embryos are those with a pair of cotyledons and normal morphology (i.e., green color and about three to about 12 mm in size). The hormone-free medium used for embryogenic callus formation is preferably the medium used for callus initiation or for embryogenic callus induction without the phytohormones, preferably $G_1$, $G_2$ or $G_3$ medium without the hormones. As will be apparent to those skilled in the art, however, other hormone-free nutrient medium may be used.

Embryogenic calli are recovered at a frequency of about 10% to about 85% depending upon the genotype used, the Class 1 genotypes producing calli faster and at higher frequencies. Embryogenic calli are characterized as midfriable, creamy, granular tissues. They are generally observed first as sections of calli or sometimes whole brown, midfriable calli become embryogenic. This embryogenic callus contains proembryoids (globular and heart-shaped structures).

For embryogenic callus formation, high temperature (e.g. around 30° C.), and low light, for example, about 9 µm²/s, are preferred.

The embryogenic callus after about two to three weeks on the embryogenic callus formation medium for a Class 1 variety or about four to six weeks for the Class 2 varieties, is subcultured on the same medium, or on a medium containing a cytokinin, preferably zeatin, an auxin, preferably NAA, and reduced carbohydrate. Preferably the auxin is present at between about 0 and about 0.2 mg/l, more preferably between about 0.01 and about 0.1 mg/l, and preferably the cytokinin is present at between about 0.5 and about 3.0 mg/l, and more preferably at a concentration between about 0.5 and about 1 mg/l. The medium $MS_{zn-g}$ as described in the Examples hereof is the most preferred of such supplemented media. This medium contains 0.1 mg/l NAA and 1 mg/l zeatin together with MS salts, 1.5% (w/v) glucose, and the other nonhormone components of the G1, G2 and G3 media. For this final embryo maturation step, however, the nonsupplemented medium $G_0$ is most preferred. The use of 2,4-D or pCPA as the auxin in the supplemented medium, or reduction of the MS salts to one-half strength in either medium reduced the capacity of the medium for embryo production and maturation.

Mature embryos vary in size from about 2 to about 12 mm, have between about one and about four cotyledons, have variable hypocotyl lengths and vary in color from pale yellow to light green to dark green and occasionally albino most likely due to tissue culture art (but this albinism is not a heritable character).

After about two to three weeks on the embryo maturation medium for both Class 1 and Class 2 genotypes, mature embryos are transferred to an embryo germination and plant development medium. Germination media are known to the art, for example as described by Stewart, J. M. et al. 1977), supra. The germination medium may be modified by the addition of gibberellic acid ($GA_3$) at a concentration of between about 0 and about 1.0 mg/l, and preferably at a concentration of between about 0.05 and about 0.2 mg/l. The germination medium may also be modified to contain an auxin, preferably NAA, at a concentration of between about 0.0 and about 0.1 mg/l, and preferably not more than about 0.05 mg/l. Also preferably the medium uses glucose rather than sucrose, preferably at a concentration of between about 0.2 and about 1.5% (w/v), and more preferably at a concentration at between about 0.5 and about 1.0%. The most preferred medium is the medium described herein as GRMgn, containing about 0.1 mg/l gibberellic acid, about 0.01 mg/l NAA and about 0.5% glucose. The preferred medium is a low ionic strength medium. Ionic strength equal to the use of MS salts at a concentration of about 1×MS salts caused burning and senescence of the tissues and caused problems in balancing root and shoot formation. The preferred medium will allow germination of at least about half of the mature somatic embryos. Iron at a concentration of between about 10 µm and about 25 µm is an important component of the germination medium. Embryo germination or "conversion" is defined as the development of the apical area of the somatic embryo resulting in shoot production (true leaves).

Embryos developed well on the $GRM_gn$ medium, as they do not tolerate higher salt concentrations well. If desired, a compound such as asparagine or ancymidol may be added to the $GRM_gn$ medium. Plantlets grown on media containing these compounds have a dark green color and good root systems. These compounds may be added in concentrations which will be apparent to the skilled worker, preferably about 5 ppm ancymidol or about 100 mg/l asparagine.

High light intensity, (e.g. about 90 µE/m²/s) are helpful for germination and plantlet development. During the embryo germination and plantlet development phase, it is also preferable to initially incubate mature embryos at high temperatures, e.g. about 30° C., for a few days to produce rapid germination, then lower the temperature to normal, about 25° C., for plantlet development.

After about one to two weeks on the embryonic germination and plantlet development medium, the plantlets, defined herein as germinated embryos having roots as well as shoots, may be transferred to media known to the art for further plant development. Preferably the plantlets and germinated embryos are transferred to Magenta cubes, such as GA7 Magenta cubes (Magenta Corporation, Chicago, Ill.), containing a phytohormone-free medium with reduced salts and carbohydrates, preferably about one-half MS salts and about 1.5% glucose. When plants are partially developed, e.g., about 8 to about 10 cm tall, having about 4 to about 6 leaves, they may be transferred to soil for maturation. Preferably the plants in soil are grown under initial high relative humidity for a gradual hardening off, and then under normal greenhouse conditions.

The foregoing procedure allows regeneration of full plants within about 14 to about 16 weeks for Class 1 varieties and about 8 to about 10 months for Class 2 varieties.

A well-defined, reproducible, and highly efficient plant regeneration scheme such as that defined above, is a prerequisite for transformation of cotton. Transformation may be performed by means known to the art for introduction of foreign DNA into plant cells and tissues. Once transformation of cells and/or tissues has been done, the transformed cells and tissues can be regenerated according to the above-described methods.

A preferred method of transformation involves the use of *Agrobacteria* to introduce foreign DNA into plant cells via infection. Means for inserting foreign DNA for transfer to plant tissues into *Agrobacteria* are well known to the art, and many vectors carrying such genes are known and readily available to the skilled worker. In a preferred embodiment, a coding region for the insecticidal crystal protein (Bt) from *Bacillus thuringiensis* is used. Vectors containing Bt are described, for example, in U.S. Patent Application Number 06/848,733, incorporated herein by reference, and in Patent Application Number 06/617,321, also incorporated herein by reference.

The vector preferably contains a "marker" gene such as the neomycinphosphotransferase II (npt II) gene conferring kanamycin resistance. Other suitable markers are known to the art.

The *Agrobacteria* containing the vector to be used to insert foreign DNA into the plant tissue is cultured by means known to the art, preferably by growing on appropriate media such as agar media containing selection agents corresponding to the marker genes present on the vector, e.g., streptomycin and chloramphenicol. Other media, such as YEP medium, may also be used.

The *Agrobacterium* colonies are scraped off the selection medium and suspended in an appropriate liquid medium, such as YEP broth or minimal medium. Preferably, however, the bacteria are suspended in a liquid medium for cotton callus culture, preferably a callus initiation medium such as $G_2$ medium as described above, preferably used at a concentration of about $2$-$4 \times 10^8$/ml. The tissues are submerged in the bacterial suspension to assure adequate contact of the tissue to be transformed with the *Agrobacteria*. Concentrations are preferably less than $10^9$ or $10^{10}$, as such high concentrations tend to kill the tissue.

The tissue to be transformed may be any regenerable cotton tissue. Preferably cotyledon, hypocotyl and leaf sections from seedlings developed from immature embryos or germinated seedlings as described above are used. The tissue pieces may be of any manipulable size, and preferably are about ½ cm².

The tissue pieces are contacted with the *Agrobacterium* suspension, preferably by dipping in the liquid culture medium and shaking to ensure contact of all edges with the culture. To minimize *Agrobacterium* on the tissue, blotting dry, preferably with filter paper, is recommended. This reduces bacterial overgrowth on the plant tissues.

The tissue are co-cultivated with the *Agrobacterium*, preferably at about 25° C., and preferably under low light (10 µE/m²/s), on a suitable medium, preferably a callus initiation medium such as G2 for long enough to ensure infection, preferably about two to three days. Preferably the tissue is plated on filter paper placed on the medium for co-cultivation to reduce bacterial overgrowth.

The infected tissues after co-cultivation are then placed on a medium to kill the *Agrobacteria*, for example by containing antibiotics known to the art. Examples of such antibiotics include carbenicillin, cloxacillin, and cefoxitin and preferably about 500 mg/l carbenicillin is used. The medium should also contain a selection agent to select for transformed tissue, corresponding to the marker gene present in the vector. The selection agent should be present at a concentration high enough that untransformed cells do not grow, but not so high as to kill the transformed tissue. The selection agent used in the Examples is kanamycin sulfate, at a concentration of between about 15 and about 40 mg/l, preferably about 25 mg/l. Concentrations above about 50 mg/l, especially in the 100 to 150 mg/l range nonselectively kill the cells. Other selection agents known to the art, such as G418, hygromycin, bleomycin, and methotrexate are also useful. It is important that all cells have contact with the medium so as to ensure selection.

After a sufficient period of time to ensure selection and initiation of transformed microcalli, generally about one to about three weeks, the tissue is regenerated as described above. Preferably when microcallus grows to about 3 to about 4 mm, it is excised from the original explant and transferred to fresh medium. The time required for regeneration of transgenic plants, that is, the plants that contain the foreign DNA, is longer than for nontransferred plants due to inoculation of tissues with *Agrobacteria*, the selection pressures and effects of antibiotics.

All regenerable cotton varieties as described above may be transformed by the above methods, and by other methods known to the art, for example as described in S. H. Mantell, et al. (1985), Principles of Biotechnology, particularly chapter 4 thereof and the references referred to therein.

Dry seeds of *G. hirsutum* cultivars (Coker 201, 310, 315 and 4360; GSA 71, 75 and 78; GSC 25 (GSA and GSC are cultivars developed by GroAgri Seed Company (a subsidiary of Agrigenetics Corporation), Lubbock, Tex.); G8160 (a breeding line from US Cotton Research Station, Shafter, Calif.); GSA-Acala hybrids No. 21 and No. 22 (No. 21 is Acala SJ-C1×GSC 20 and No. 22 is Acala SJ-C1×GSA 74-7, 127 hybrid); and Acala SJ-2) were surface sterilized as described (Firoozabady, E. and DeBoer, D. L. (1986) *Plant Cell Reports* 5:127-131, except that seeds were exposed to bleach for only 8-10 minutes, and germinated on $G_O$ medium. Composition of media used in cotton regeneration is presented in Table 14 unless published elsewhere or modifications are mentioned in the text. Immature seeds were obtained from cotton bolls (3-5 cm diam., 40-60 days after pollination) of Coker 201 and 315 and GSA cultivars. Bolls were surface sterilized 20 minutes in 33% commercial bleach and rinsed twice in sterile distilled water. Immature seeds were manually delinted, seed coats were removed, and the embryos (7-10 mm) were germinated on G0 medium and incubated as described in Firoozabady and DeBoer, (1986), supra.

Cotyledon pieces (approximately 0.6 cm² surface area) and hypocotyl sections (5-8 mm length) of 7- to 10-day-old seedlings and leaf pieces (approximately 0.6 cm² surface area) of 21-day-old plants were placed on callus initiation medium, $G_2$. Only hypocotyl sections were cultured from precociously germinated seedlings. After two to three weeks for Cokers or seven to nine weeks for GSA's, calli were transferred onto embryogenic callus induction media ($G_1'G_3$). Embryogenic calli were transferred to G0 or $MS_{zn-g}$ medium to produce mature somatic embryos. These were germinated on the medium suggested by Stewart and Hsu (1977), supra, modified by addition of 0.1 mg/l $GA_3$ (filter-sterilized), 0.01 mg/l NAA and 0.5% glucose instead of sucrose ($GRM_gn$). After one to two weeks, the germinated embryos were transferred to ½G0 or $GRM_gn$ in GA7 Magenta cubes (Magenta Corp., Chicago, Ill.) to develop further. The plants (10-12 cm tall, 5-10 leaves) were transferred to soil under high relative humidity, gradually hardened off, and transferred to normal greenhouse conditions.

To study the effects of temperature and light intensity on different stages of tissue culture, tissues were incubated at 25±1° C. or 30±1° C. under high light intensity (90 μE/m²/s) or low light intensity (9 μE/m²/s) provided with cool white fluorescent lamps (GTE, Salem, Mass.). Also, the effects on embryo quality and germination of different media containing additives such as ancymidol (Elanco Products, Co., Indianapolis, Ind.), asparagine, or different glucose concentrations were examined.

Immature somatic embryos were characterized by lack of well-defined organs. Normal somatic embryos are those with a pair of cotyledons and normal morphology (i.e., green color and 3-12 mm in size).

Results were as follows:

Callus initiation and proliferation. A range of media were tested for callus initiation from several cultivars. Medium G2 (5 mg/l 2iP and 0.1 mg/l NAA, Table 14) was best for callus initiation and growth in many cultivars tested. Medium G2 was superior to G1, G3, EF18 (2 mg/l NAA and 1 mg/l kinetin, Shoemaker, R. C. et al. (1986) supra.), and the medium containing 2 mg/l IAA and 1 mg/l kinetin used by Smith R. H. et al. (1977) supra. for *G. arboreum* callus initiation. Including MS vitamins and/or 5% (v/v) coconut milk in some media such as EF18 were helpful in overall callus growth, but still these were inferior to $G_2$ medium.

SMpi medium (7.5 mg/l 2iP and 0.1 mg/l pCPA, Firoozabady, E. (1986), supra and SMgpi (SMpi with glucose instead of sucrose) were good for callus proliferation and maintenance, but still inferior to G2. Relatively hard, creamy granular calli were produced on media SMpi and SMgpi. Rapid callus initiation on G2 medium and proliferation on SMpi or SMgpi media indicating high level of 2iP or high 2iP/auxin ratio is important in these processes.

A range of gross morphology of the initiated calli was observed and varied from hard (nonfriable) to extremely friable, midfriable being the desired morphology. The degree of friability was highly dependent on the hormones used. For example, less friable tissues were obtained with higher levels of 2iP and higher 2iP/auxin ratios. Friability generally increased with higher NAA concentrations. Inclusion of 2,4-D in the media resulted in production of hard, compact calli. When no hormone was included in the subculture medium, midfriable tissues were obtained.

Embryopenic callus induction. Embryogenic calli were characterized as midfriable creamy granular tissues. Embryogenic calli were observed first as sections of calli or sometimes whole brown midfriable calli became embryogenic. These contained proembryoids (globular and heart-shaped structures). Transferring calli from EF18 to EFs18 (EF18 containing sucrose instead of glucose) was predicted by Shoemaker, R. C. et al. (1986) supra. to induce embryogenic callus formation. With Coker 201 and 315, this was possible at a very low frequency (2-3%, Table 15), but other cultivars did not respond to this exchange of carbohydrates. Calli on EFs18 (and other sucrose containing-media) generally produced a lot of phenolics, turned brown arid eventually died. With the subculture medium used by Davidonis, G. H., et al. (1983) supra., only Coker 201 and 310 produced embryogenic calli (data not shown). In this work, media G1 and G3 containing 5 mg/l NAA produced massive amounts of embryogenic calli over several cultivars tested (Table 15), indicating that NAA is important for embryogenic callus induction. The fact that G3 was better than G1 also indicates that a high NAA/2iP ratio is beneficial for embryogenic callus induction in cotton.

Use of germinated immature seeds as the source of explants resulted in a higher rate of embryogenic callus formation in GSA lines but not in Coker 201 and 315.

Maturation and germination of somatic embryos and plant regeneration. After three to four weeks (Cokers) or approximately four months (GSA'S) on embryogenic callus induction medium (G I or $G_3$), embryogenic calli containing globular through torpedo stage somatic embryos were transferred to hormone-free ($G_O$) medium or sometimes to zeatin/NAA ($MS_{zn-g}$) containing medium. This subculture resulted in maximum embryogenic callus production (Table 15) and within two to three weeks, numerous tulip-shaped and mature embryos developed. Medium $G_0$ was best for somatic embryo maturation with several cultivars (Coker 201, 310, and 4360); GSA 78; and hybrid No. 21) tested. $MS_{zn-g}$ was the second best in this regard. Replacing NAA with 2,4-D or pCPA in $MS_{zn-g}$ media, greatly reduced their capacity for embryo production and maturation.

Embryos were very different in size (2-12 mm range) and morphology. They had different numbers of cotyledons (1-4), hypocotyl length, and colors (dark green, light green, and pale yellow).

Somatic embryos were transferred onto a lower ionic strength medium ($GRM_{gn}$) to germinate. $GRM_{gn}$ was the best medium for embryo germination and plantlet development (Tables 16 and 17). Eliminating $GA_3$ and NAA reduced germination frequencies of the somatic embryos (GRM, Table 16). Generally, approximately 50% mature somatic embryos (normal or abnormal) germinated on $GRM_{gn}$ (Tables 16 and 17). Larger embryos (8-12 mm, mature) germinated more frequently (approximately 90%) than small embryos (2-4 mm, immature). Usually $G_1/G_3$-$G_0$-$GRM_{gn}$ resulted in higher frequencies of embryos germination and plantlet development than $G_1$-$GRM_{gn}$, $G_3$-$GRM_{gn}$, or any other transfer regimes (Table 17). This was probably due to higher frequencies of normal embryos developed on $G_0$ medium. Most germinated embryos produced both roots and leaves (plantlets). At the time of this writing in Coker 201, 255; Coker 310, 2; Coker 315, 6; Coker 4360,7; No. 21,4; No. 22,3; GSA 71, 12; GSA 75,20; GSA 78,26 and GSC 30 plants have been regenerated and successfully transferred to soil and green house conditions.

Most of the regenerated plants have normal morphology, are fertile and have set seed.

Effects of light and temperature on different phases of cotton tissue culture. Different phases of cotton tissue culture were affected both by light and temperature, although these factors had less influence than medium composition. For callus initiation, a high temperature (30° C.) was preferred and light intensity did not play an important role. Calli have been initiated and maintained at the same rate in complete darkness and in different light intensities (9-90 μE/m$^2$/s). For embryogenic callus formation and proliferation, high temperature and low light (9 gE/m$^2$/s) were preferred in the varieties tested: Coker 201 and 315 and GSA 78. After somatic embryos were formed, high light intensity (90 μE/m$^2$/s) proved to be very helpful for germination and plantlet development. It was also very helpful to incubate mature embryos at 30° C. for a few days to rapidly germinate, then at 25° C. for plantlet development. At high temperatures, the embryos and plantlets often grew slowly and callused.

Other observations on cotton regeneration. Embryogenic calli proliferated on $G_6$ medium (same as $G_0$ but with 6% glucose and 100 mg/l asparagine) with little mature embryo production, indicating the effects of high glucose and asparagine on embryogenic callus proliferation. Somatic embryos and plantlets in Coker 201 and 4360 have been induced to form callus (on $G_2$ medium) or embryogenic callus (on $G_6$ medium) and to undergo a second cycle of plant regeneration (FIG. 4). Inclusion of 5 rpm ancymidol or 100 mg/l asparagine in GRM medium resulted in healthier plantlets; the plantlets had dark green leaves and a better root system.

Some somatic embryos and plantlets developed abnormally. For example, occasionally, embryos were formed on previously matured embryos, some plantlets produced callus on top or on the stem, and some produced many slim shoots. However, these abnormal tissues could be induced to form callus and subsequently regenerate normally.

Some calli from GSA 78 and GSA-Acala hybrid No 21 have spontaneously regenerated shoots via organogenesis. However, to date we have only been able to regenerate plants from these shoots at frequencies of approximately 25% because of difficulties in inducing root formation.

Summary of results. A highly efficient and general method for plant regeneration in cotton, *G. hirsutum* has been developed. The method is very rapid for Class 1 cultivars (Cokers—14-18 weeks) and relatively slow for Class 2 cultivars (GSA's—8-10 months). For Class 2 cultivars developmental stages progressed more slowly than for Class 1 cultivars, and with lower efficiency of regeneration. Use of precociously germinated seedlings as the source of explants increased frequencies of embryogenic calli formation with Class 2 but not with Class 1 cultivars. Embryogenic cultures are very stable, and upon monthly subculture on $G_0$ medium, numerous somatic embryos are produced; at this writing plants are still being regenerated from 15-month-old Coker 201 and GSA 78 embryogenic callus lines.

In comparing different media formulations, it is clear that a high 2iP/auxin ratio is best for callus initiation and proliferation but must be exchanged for a high NAA/cytokinin ratio before embryogenic calli will form. Interestingly, in *G. hirsutum* the ability to form embryogenic calli appears to be influenced by NAA (this study, Davidonis, G. H., et al., supra Shoemaker, R. C. et al., supra). We have found that continuous subculture on high levels of 2iP suppresses morphogenesis. However, upon two subcultures each on induction medium ($G_1$ or $G_3$ and embryo formation medium ($G_0$) embryos are formed.

For maximum somatic embryo formation, it was essential to subculture calli hormone-free medium. The length of time on hormone-containing medium (i.e., $G_1$ or $G_3$), however, had an effect on embryo formation.

In the present study, since over 100 embryos were formed per dish, an ample number was readily obtained to test the effects of various cultural conditions on embryo germination and plant development. Germination of somatic embryos was highly dependent on frequency of normal embryos and ionic strength of the medium. Abnormal embryos rarely germinated under any condition and had a long lag period. Small embryos also germinated infrequently and slowly. Normal and large embryos (greater than 5 mm), however, germinated well on appropriate media. Embryos placed on BT medium (Beasley, C. A., et al., supra.) either developed callus or their growth stopped and all tissues became necrotic. Embryos were unable to tolerate high-salt (Table 16, EG) or high-sugar (Table 16, EG, $EG_1$) media, and myo-inositol was partially inhibitory to root development (Table 16, EG1, EG3). Often root or shoot development was a problem, and callusing was very common. The embryos performed best on modifications of a medium recommended by Stewart, J. N., et al., supra., GRMg. Addition of compounds such as asparagine and ancymidol to $GRM_{gn}$ proved helpful in embryo development. Balanced root and shoot growth was obtained using the medium $GRM_{gn}$. Embryo growth was slower in the medium lacking hormones (GRM). Embryo germination frequencies were higher on $GRM_{gn}$ medium in cases where embryos matured on hormone-free medium, $G_0$, due to production of higher frequencies of normal embryos on $G_0$ medium (Table 17). On hormone-containing media, $G_1$ and $G_3$, proembryoids grew slowly and many callused and proliferated instead of undergoing maturation.

Cotton Transformation Example

The neomycinphosphotransferase II (npt II) gene confers kanamycin resistance in eukaryotes when inserted behind eukaryotic promoters. The npt II coding sequence from bacterial transposon Tn5 was inserted behind the cauliflower mosaic virus (CaMV) 19S promoter and was terminated by addition of T-DNA ORF26. This chimeric gene, T-DNA OCS gene, npt II gene, and A and B borders of T-DNA was inserted into the broad host range replicon pTJS75 to create pH575. The construction of this vector is more fully described in U.S. Patent Applications No. 06/788,984 filed Oct. 21, 1985, and incorporated herein by reference.

*Agrobacterium tumefaciens* strain LBA4404 carrying pH575, and LBA4404 without the vector were cultured on Luria broth agar medium containing 250 μg/ml streptomycin and 25 μg/ml kanamycin (both from Sigma) for selection. Strain LBA4404 is described in Hoekema, et al. (1983) Nature 303:179. This is a widely available strain also freely available from the authors. Bacteria were scraped off the agar medium, suspended in a liquid medium for cotton callus culture ($G_2$) to a concentration of 2-4×10$^8$ cells/ml and were used for inoculation of cotyledon segments.

To transform cotton tissues, cotyledon pieces (approximately 0.5 cm$^2$ surface area) from sterile 12- to 14-day-old Coker 201 seedlings were dipped in *A. tumefaciens* liquid cultures in Petri dishes and gently shaken for a few seconds to ensure contact of all cotyledon edges with the bacterial cultures. The cotyledon pieces were then blotted dry and plated on Whatman #1 filter paper on a callus initiation medium ($G_2$) containing MS salts (Gibco), 100 mg/l myo-inositol, 0.4 mg/l thiamine HCL, 5 mg/l 2iP, 0.1 mg/l NAA (all from Sigma), 3% (w/v) glucose, 0.2% Gel-rite (Kelco), pH5.9. Filter paper was not necessary for transformation, but greatly reduced bacterial overgrowth on plant tissues. After three days cultivation at low temperature (25° C.) and low light, cotyledon pieces were transferred to Petri plates containing the same medium, without the filter paper, and containing 500 mg/l carbenicillin and 25 mg/l kanamycin sulphate (both from U.S. Biochemicals).

After 7-10 days of incubation, cotyledon pieces initiated transformed kanamycin-resistant microcalli (0.5 mm) at wound sites, while no callus from control untreated tissues or from tissues treated with LBA4404 grew on kanamycin. Two to three weeks later, 2-4 mm calli were excised from original explants and transferred to fresh medium. All the calli were kanamycin-resistant and 80-100% of the kanamycin-resistant calli were positive when tested for octopine (Table 18). Two to three weeks later, the calli were placed and maintained on embryogenic medium $G_O$(same as $G_2$ with no hormones) under selection. Mature somatic embryos were transferred to lower ionic strength medium, $GRM_{gn}$ described above. Plants were shown to be transformed by their resistance to kanamycin in leaf callus assay, production of octopine, enzyme-linked immunoassay (ELISA) for NPT II (Table 19) and by DNA, and western blot hybridization analyses. Plants were transferred to soil for further analysis. The whole process from infection until transgenic plants were transferred to soil took about six months. Similar results were obtained in replicate experiments.

Transgenic cotton plants are readily obtained with the transformation-regeneration system described here. The system is very efficient and has been modified to be applicable for plant regeneration of a number of commercial cultivars of cotton, although the efficiency and time period for regeneration of other cultivars are not as short as for Coker 201. The use of a selectable kanamycin-resistance marker was necessary. Kanamycin-resistant microcalli developed at the wound sites. In the absence of selection, barely detectable octopine-positive calli were obtained in frequencies of 10-20% indicating transformation frequencies were reasonably high among the cell populations of some calli.

Generally, 150-200 calli per 100 cotyledon sections were produced on kanamycin; 100% of these survived during subculture and remained to be resistant to kanamycin; about 80-100% of these were octopine-positive and in Coker 201 more than 80% became embryogenic and regenerated into plants. At this writing, approximately 86 octopine-positive plantlets have been produced using different constructs. About 30% of these regenerated into normal plants. Six of the octopine-positive plants tested showed the DNA fragments of appropriate size showing ocs, NPT II, and bt genes. In another experiment eight octopine-positive plants and 10 octopine-positive calli tested were positive for NPT II protein in western blot and in ELISA. All octopine-positive plantlets so far tested were kanamycin-resistant in leaf callus assay. The efficiency of this transformation-regeneration system permits the introduction of desirable genes such as insect-resistance, herbicide-resistance and virus-resistance to cotton. Cotyledon pieces (approximately 0.5 cm² surface area) from sterile 12 to 14 day old coker 201 seedlings were dipped in *A. tumefaciens* liquid cultures in Petri dishes and gently shaken for a few seconds to ensure contact of all cotyledon edges with the bacterial cultures. the cotyledon pieces were then blotted dry and plated on Whatman #1 filter paper on a callus initiation $G_2$ medium containing 0.2% "GEL-RITE" (Kelco). After three days cocultivation at low temperature (25° C.) and 16 h/day photoperiod at 90 µE·m⁻¹·s⁻¹ light, cotyledon pieces were transferred to Petri plates without the filter paper containing the same medium supplanted with 500 mg/l carbenicillin and 25 mg/l kanamycin sulfate (both from U.S. Biochemicals).

TABLE 1

Insects susceptible to *B. thuringiensis* insecticidal protein

COLEOPTERA

*Popillia japonica* (Japanese beetle)
*Sitophilus granarius* (granary weevil)

DIPTERA

*Aedes aegypti* (yellow-fever mosquito)
*A. atlanticus*
*A. cantans*
*A. capsius*
*A. cinereus*
*A. communis*
*A. detritus*
*A. dorsalis*
*A. dupreei*
*A. melanimon*
*A. nigromaculis* (pasture mosquito)
*A. punctor*
*A. sierrensis* (western treehole mosquito)
*A. sollicitans* (brown salt marsh mosquito)
*Aedes* sp.
*A. taeniorhynchus* (black salt marsh mosquito)
*A. tarsalis*
*A. tormentor*
*A. triseriatus*
*A. vexans* (inland floodwater mosquito)
*Anopheles crucians*
*A. freeborni*
*A. quadrimaculatus* (common malaria mosquito)
*A. sergentii*
*A. stephensi*
*Anopheles* sp.
*Chironomus plumosus* (*Chironomus*: midges, biting)
*Chironomus* sp.
*C. tummi*
*Culex erraticus*
*C. inornata*
*C. nigripalus*
*C. peus*
*C. pipiens* (northern house mosquito)
*C. quinquefasciatus* (*C. pipiens fatigans*) (southern house mosquito)
*C. restuans*
*Culex* sp.
*C. tritaeniorhynchus*
*C. tarsalis* (western encephalitis mosquito)
*C. territans*
*C. univittatus*
*Culiseta incidens* (*Culiseta*: mosquitos)
*C. inornata*
*Diamessa* sp.
*Dixa* sp. (*Dixa*: midges)
*Eusimulium* (*Simulium*) *latipes* (*Eusimulium*: gnats)
*Goeldichironomus holoprasinus*
*Haematobia irritans* (horn fly)
*Hippelates collusor*
*Odagmia ornata*
*Pales pavida*
*Polpomyla* sp. (*Polpomyia*: midges, biting)
*Polypedilum* sp. (*Polypedilum*: midges)
*Psorophora ciliata*
*P. columiae* (*confinnis*) (Florida glades mosquito, dark rice field mosquito)
*P. ferox*
*Simulium alcocki* (*Simulium*: black flies)
*S. argus*
*S. cervicomatum*
*S. damnosum*
*S. jenningsi*
*S. piperi*
*S. tescorum*
*S. tuberosum*
*S. unicornatum*
*S. venustum*

TABLE 1-continued

Insects susceptible to *B. thuringiensis* insecticidal protein

*S. verecundum*
*S. vittatum*
*Uranotaenia inguiculata*
*U. lowii*
*Wyeomyia mitchellii* (*Wyeomyia*: mosquitos)
*W. vanduzeei*
HYMENOPTERA

*Athalia rosae* (as *colibri*)
*Nematus* (*Pteronidea*) *ribesii* (imported currantworm)
*Neodiprion banksianae* (jack-pine sawfly)
*Priophorus tristis*
*Pristiphora erichsonii* (larch sawfly)
LEPIDOPTERA

*Achaea janata*
*Achroia griseila* (lesser wax moth)
*Achyra rantalis*
*Acleris variana* (black-headed budworm)
*Acrobasis* sp.
*Acrolepia alliella*
*Acrolepiopsis* (*Acrolepia*) *assectella*
*Adoxophyes orana* (apple leaf roller)
*Aegeria* (*Sanninoidea*) *exitiosa* (peach tree borer)
*Aglais urticae*
*Agriopsis* (*Erannis*) *aurantiaria* (*Erannis*: loopers)
*A.* (*E.*) *leucophaeria*
*A. marginaria*
*Agrotis ipsilon* (as *ypsilon*) (black cutworm)
*A. segetum*
*Alabama argillacea* (cotton leafworm)
*Alsophila aescularia*
*A. pometaria* (fall cankerworm)
*Amorbia essigana*
*Anadevidia* (*Plusia*) *peponis*
*Anisota senatoria* (orange-striped oakworm)
*Anomis flava*
*A.* (*Cosmophila*) *sabulifera*
*Antheraea pernyi*
*Anticarsia gemmatalis* (velvetbean caterpillar)
*Apocheima* (*Biston*) *hispidaria*
*A. pilosaria* (*pedaria*)
*Aporia crataegi* (black-veined whitemoth)
*Archips argyrospilus* (fruit-tree leaf roller)
*A. cerasivorana* (ugly-nest caterpillar)
*A. crataegana*
*A. podana*
*A.* (*Cacoecia*) *rosana*
*A. xylosteana*
*Arctia caja*
*Argyrotaenia mariana* (gray-banded leaf roller)
*A. velutinana* (red-banded leaf roller)
*Ascia* (*Pieris*) *monuste orseis*
*Ascotis selenaria*
*Atteva aurea* (alianthus webworm)
*Autographa californica* (alfalfa looper)
*A.* (*Plusia*) *gamma*
*A. nigrisigna*
*Autoplusia egena* (bean leaf skeletonizer)
*Azochis gripusalis*
*Bissetia steniella*
*Bombyx mori* (silkworm)
*Brachionycha sphinx*
*Bucculatrix thurberiella* (cotton leaf perforator)
*Bupolus pinarius* (*Bupolus*: looper)
*Cacoecimorpha pronubana*
*Cactoblastis cactorum*
*Caloptilia* (*Gracillaria*) *invariabilis*
*C.* (*G.*) *syringella* (lilac leaf miner)
*C.* (*G.*) *theivora*
*Canephora asiatica*
*Carposina niponensis*
*Ceramidia* sp.
*Cerapteyx graminis*
*Chilo auricilius*
*C. sacchariphagus indicus*
*C. suppressalis* (rice stem borer)

*Choristoneura fumiferana* (spruce budworm)
*C. murinana* (fir-shoot roller)
*Chrysodeixis* (*Plusia*) *chalcites*
*Clepsis spectrana*
*Cnaphalocrocis medinalis*
*Coleotechnites* (*Recurvia*) *milleri* (lodgepole needle miner)
*C. nanella*
*Colias eurytheme* (alfalfa caterpillar)
*C. lesbia*
*Colotois pennaria*
*Crambus bonifatellus* (fawn-colored lawn moth, sod webworm)
*C. sperryellus*
*Crambus* sp.
*Cryptoblabes gnidiella*
*Cydia funebrana*
*C.* (*Grapholitha*) *molesta* (oriental fruit moth)
*C.* (*Laspeyresta*) *pomonella* (codling moth)
*Datana integerrima* (walnut caterpillar)
*D. ministra* (yellow-necked caterpillar)
*Dendrolimus pini*
*D. sibiricus*
*Depressaria marcella* (a webworm)
*Desmia funeralis* (grape leaf folder)
*Diachrysia* (*Plusia*) *orichalcea* (a semilooper)
*Diacrisia virginica* (yellow woolybear)
*Diaphania* (*Margaronia*) *indica*
*D. nitidalis* (pickleworm)
*Diaphora mendica*
*Diatraea grandiosella* (southwestern corn borer)
*D. saccharalis* (sugarcane borer)
*Dichomeris marginella* (juniper webworm)
*Drymonia ruficornis* (as *chaonia*)
*Drymonia* sp.
*Dryocampa rubicunda*
*Earias insulana*
*Ectropis* (*Boarmia*) *crepuscularia*
*Ennomos subsignaria* (elm spanworm)
*Elphestia* (*Cardra*) *cautella* (almond moth)
*E. elutella* (tobacco moth)
*E.* (*Anagasia*) *kuehniella* (Mediterranean flour moth)
*Elpinotia tsugana* (a skeletonizer)
*Epiphyas postvittana*
*Erannis defoliaria* (mottled umber moth)
*E. tiliaria* (linden looper)
*Erinnysis ello*
*Eriogaster henkei*
*E. lanestris*
*Estigmene acrea* (salt marsh caterpillar)
*Eublemma amabilis*
*Euphydryas chalcedona*
*Eupoecilia ambiguella*
*Euproctis chrysorrhoea* (*Nygmi phaeorrhoea*) (browntail moth)
*E. fraterna*
*E. pseudoconspersa*
*Eupterote fabia*
*Eutroula* (*Simaethis*) *pariana*
*Euxoa messoria* (dark-sided cutworm)
*Galleria mellonella* (greater wax moths)
*Gastropacha quercifolia*
*Halysidota argentata*
*H. calyae* (hickory tussock moth)
*Harrisina brillians* (western grape skeletonizer)
*Hedya nubiferana* (fruit tree tortrix moth)
*Heliothis* (*Helicoverpa*) *armigera* (*Heliothis* = *Chloridea*) (gram pod borer)
*H.* (*H.*) *assulta*
*Heliothis petigera*
*H. virescens* (tobacco budworm)
*H. viriplaca*
*H. zea* (cotton bollworm, corn earworm, soybean podworm, tomato fruitworm, sorghum headworm etc.)
*Hellula undalis* (cabbage webworm)
*Herpetogramma phaeopteralis*
*Heterocampa guttivitti* (saddled prominent)
*H. manteo* (variable oak leaf caterpillar)
*Holcocera pulverea*
*Homoeosoma electellum* (sunflower moth)

TABLE 1-continued

Insects susceptible to *B. thuringiensis* insecticidal protein

*Homona magnanima*
*Hyloicus pinastri*
*Hypeuryntis coricopa*
*Hyphantria cunea* (fall webworm)
*Hypogymna mono*
*Itame* (*Thamnonoma*) *wauria* (a spanworm)
*Junonia coenia* (buckeye caterpillars)
*Kakivoria flavofasciata*
*Keiferia* (*Gnorimoschema*) *lycopersicella* (tomato pinworm)
*Lacanobia* (*Polia*) *oleracea*
*Lambdina athasaria pellucidaria*
*L. fiscellaria fiscellaria* (hemlock looper)
*L. fiscellaria lugubrosa*
*L. fiscelleria somniaria*
*Lampides boeticus*
*Leucoma* (*Stilpnotia*) *salicis* (satin moth)
*L. wiltshirei*
*Lobesia* (= Polychrosis) *botrana*
*Loxostege commixtalis* (alfalfa webworm)
*L. sticticallis* (beet webworm)
*Lymantria* (*Porthetria*) *divpar* (gypsy moth) (*Lymantria*: tussock moth)
*L. monacha* (nun-moth caterpillar)
*Malacosoma americanum* (eastern tent caterpillar)
*M. disstria* (forest tent caterpillar)
*M. fragilis* (= *fragile*) (Great Basin tent caterpillar)
*M. neustria* (tent caterpillar, lackey moth)
*M. neustria* var. *testacea*
*M. pluviale* (western tent caterpillar)
*Mamestra brassicae* (cabbage moth)
*Manduca* (*Intoparce*) *quinquemaculata* (tomato hornworm)
*M* (*I.*) *sexta* (tobacco hornworm)
*Maruca testulalis*
*Melanolophia imitata*
*Mesographe forficalis*
*Mocis repanda* (*Mocis*: semilooper)
*Molippa sabina*
*Monema flavescens*
*Mythimna* (*Pseudaletia*) *unipuncta* (armyworm)
*Nephantis serinopa*
*Noctua* (*Triphaena*) *pronuba*
*Nomophila noctuella* (lucerne moth)
*Nymphalis antiopa* (mourning-cloak butterfly)
*Oiketicus moyanoi*
*Ommatopteryx texana*
*Operophtera brumata* (winter moth)
*Opsophanes* sp.
*O. fagata*
*Orgyia* (*Hemerocampa*) *antiqua*
*O. leucostigma* (white-marked tussock moth)
*O.* (*H.*) *pseudotsugata* (Douglas-fir tussock moth)
*O. thyellina*
*Orthosia gothica*
*Ostrinia* (*Pyrausta*) *nubialis* (European corn borer)
*Paleacrita vernata* (spring cankerworm)
*Pammene juliana*
*Pandemis dumetana*
*P. pyrusana*
*Panolis flammea*
*Papilio cresphontes* (orangedog)
*P. demoleus*
*P. philenor*
*Paralipsa* (*Aphemia*) *gularis*
*Paralobesia viteana*
*Paramyelosis transitella*
*Parnara guttata*
*Pectinophora gossypiella* (pink bollworm)
*Pericallia ricini*
*Peridroma saucia* (variegated cutworm)
*Phalera bucephala*
*Phlogophora meticulosa*
*Phryganidia californica* (California oakworm)
*Phthorimaea* (= *Gnorimoschema*) *operculella* (potato tuberworms)
*Phyllonotycter* (*Lithocolletis*) *blancardella*
*Pieris brassicae* (large white butterfly)
*P. canidia sordida*
*P. rapae* (imported cabbageworm, small white butterfly)
*Plathypena scabra* (green cloverworm)

TABLE 1-continued

Insects susceptible to *B. thuringiensis* insecticidal protein

*Platynota* sp.
*P. stultana*
*Platyptilia carduidactyla* (artichoke plume moth)
*Plodia interpunctella* (Indian-meal moth)
*Plutella xylostella* as *maculipennis* (diamondback moth)
*Prays citri* (citrus flower moth)
*P. oleae* (olive moth)
*Pseudoplusia includens* (soybean looper)
*Pygaera anastomosis*
*Rachiplusia ou*
*Rhyacionia buoliana* (European pine shoot moth)
*Sabulodes caberata*
*Samia cynthia*
*Saturnia pavonia*
*Schizura concinna* (red-humped caterpillar)
*Schoenobius bipunctifer*
*Selenephera lunigera*
*Sesamia inferens*
*Sibine apicalis*
*Sitotroga cerealella* (Angoumois grain moth)
*Sparganothis pilleriana*
*Spionota* (*Tmetocera*) *ocellana* (eye-spotted budmoth)
*Spilosoma lubricipeda* (as *menthastri*)
*S. virginica*
*Spilosoma* sp.
*Spodoptera* (*Prodenia*) *eridania* (southern armyworm)
*S. exigua* (beet armyworm, lucerne caterpillar)
*S. frugiperda*
*S. littoralis*
*S. litura*
*S. mauritia*
*S.* (*P.*) *ornithogalli* (yellow-striped armyworm)
*S.* (*P.*) *praefica*
*Syllepte derogata*
*S. silicalis*
*Symmerista canicosta*
*Thaumetopoea pilyocampa* (pine processionary caterpillar)
*T. processionea*
*T. wauaria* (currant webworm)
*T. wilkinsoni*
*Thymelicus lineola* (European skipper)
*Thyridopteryx ephemeraeformis* (bagworm)
*Tineola bisselliella* (webbing clothes moth)
*Tortrix viridana* (oak tortricid)
*Trichoplusia ni* (cabbage looper)
*Udea profundalis* (celery leaf tier)
*U. rubigalis*
*Vanessa cardui* (painted-lady)
*V. io*
*Xanthopastis timais*
*Xestia* (*Amathes, Agrotis*) *c-nigrum* (spotted cutworm)
*Yponomeuta cognatella* (= *Y. evonymi*) (*Yponomeuta = Hyponomeuta*)
*Y. evonymella*
*Y. mahalebella*
*Y. malinella* (small ermine moth)
*Y. padella* (small ermine moth)
*Y. rorrella*
*Zeiraphera diniana*
MALLOPHAGA

*Bovicola bovis* (cattle biting louse)
*B. crassipes*
*B. limbata*
*B. ovis*
*Liperus caponis* (wing louse)
*Menacanthus stramineus*
*Menopon gallinae* (shaft louse)
TRICHOPTERA

*Hydropsyche pellucida*
*Potamophylax rotundipennis*

TABLE 2

Plants recommended for protection by *B. thuringiensis* insecticidal protein

| | | |
|---|---|---|
| alfalfa | escarole | pomegranate |
| almonds | field corn | potatoes |
| apples | filberts | radishes |
| artichokes | flowers | rangeland |
| avocados | forage crops | raspberries |
| bananas | forest trees | safflower |
| beans | fruit trees | shade trees |
| beets | garlic | shingiku |
| blackberries | grapes | small grains |
| blueberries | hay | soybeans |
| broccoli | kale | spinach |
| brussels sprouts | kiwi | squash |
| cabbage | kohlrabi | stonefruits |
| caneberries | lentils | stored corn |
| carrots | lettuce | stored grains |
| cauliflower | melons | stored oilseeds |
| celery | mint | stored peanuts |
| chard | mustard greens | stored soybeans |
| cherries | nectarines | stored tobacco |
| Chinese cabbage | onions | strawberries |
| chrysanthemums | oranges | sugarbeets |
| citrus | ornamental trees | sugar maple |
| collards | parsley | sunflower |
| cos lettuce | pasture | sweet corn |
| cotton | peaches | sweet potatoes |
| cranberries | peanuts | tobacco |
| crop seed | pears | tomatoes |
| cucumbers | peas | turf |
| currants | pecans | turnip greens |
| dewberries | peppers | walnuts |
| eggplant | pome fruit | watermelons |
| endive | | |

TABLE 3

Varieties of *B. thuringiensis*

*alesti*
*aizawai*
*canadensis*
*dakota*
*darmstadiensis*
*dendrolimus*
*entomocidus*
*finitimus*
*fowleri*
*galleriae*
*indiana*
*israelensis*
*kenyae*
*kurstaki*
*kyushuensis*
*morrisoni*
*ostriniae*
*pakistani*
*sotto*
*thompsoni*
*thuringiensis*
*tolworthi*
*toumanoffi*
*wuhanensis*

TABLE 4

Index of plasmid and strains

| Strain or Plasmid | Constructed or used in Example | See FIG. | Made From (α comments) |
|---|---|---|---|
| *A. tumefaciens* | 6 | | (ubiquitous) |
| *A. rhizogenes* | 5 | | (also see background) |

TABLE 4-continued

Index of plasmid and strains

| Strain or Plasmid | Constructed or used in Example | See FIG. | Made From (α comments) |
|---|---|---|---|
| *B. thuringiensis* var. kurstaki HD-73 | 1.1 | 1 | |
| ColE1 | 2.5 | | |
| *E. coli* GM33 | 2.3 | | |
| *E. coli* HB101 | 1.1 | | |
| *E. coli* JM103 | 2.1 | | |
| *E. coli* K802 | 2.2 | | |
| MBT3 | 3.3 | | M13mp8, p123/58-10 |
| MBT3 (Nco) | 3.4 | | MBT3 |
| MBT14 | 3.3 | | M13mp8, p123/58-10 |
| mWB2344 | 2.1 | | |
| M13-Bt-A | 2.1 | | mWB2344, p123/58-10 |
| M13-Bt-A(Bam) | 2.1 | | M13-Bt-A |
| M13-Bt-S | 2.1 | | mWB2344, p123/58-10 |
| M13mp7 | 3.1 | | |
| M13mp8 | 3.3 | | |
| M13-PpBt | 4.4 | | MBT3 (Nco), M13-3.8Ab |
| M13-1 | 3.1 | | M13mp7, pNS5 |
| M13-3 | 3.1 | | M13mp7, pNS5 |
| M13-3A/B18a | 3.2 | | M13-3 |
| M13-3.8A | 4.1 | | M13mp7, 177.4 |
| M13-3.8Aa | 4.2 | | M-13-3.8Ac |
| M13-3.8Ab | 4.3 | | M13-3.8Aa |
| M13-3.8Ac | 4.2 | | M-13-3.8A |
| M13-3.8S | 4.1 | | M13mp7, 177.4 |
| pBR322 | 1.1 | | M13mp7, 177.4 |
| pCF44 | 3.1 | | pBR322, pTiC58 |
| pCF44A | 3.1 | | pCF44 |
| pKS-proI | 2.2 | 3 | pKS111, = pTR-proI |
| pKS-proI(Bam) | 2.2 | 2.2 | pKS-proI |
| pKS-4 | 2.5 | 2 | pBR322, pRZ102 |
| pKS111 | 2.2, 12.3 | 2, 3 | pRK290, pTi15955 |
| pKS111-K | 4.5 | | pKS4 (prZ102), pKS111 |
| pKS111-N | 3.5 | | pCF44, pKS111-K |
| pKS111-NpBt | 3.5 | | MBT3(Nco), M13-3A/B18a |
| pKS111-PpBt | 4.5 | | M13-PpBt, pKS111-K |
| pNS5 | 3.1 | | pBR322, pCF44A |
| pPH1J1 | 9 | | |
| pRK290 | 2.2, 9 | | |
| pRK2013 | 9 | | |
| pRZ102 | 2.5 | | ColE1, Tn5 |
| pTiA66 | 2.4 | | |
| pTi15955 | 2.4 | 2 | |
| p8.8 | 4.1 | | pBR322, 177.4 |
| p11-83a | 2.3 | 3 | pKS-proI(Bam), pKS-4 |
| p11-83b | 2.3 | 3 | p11-83a, M13-Bt-A(Bam) |
| p123/58-3 | 1.1 | 1 | *B. thuringiensis* var. kurstaki HD-73, pBR322 |
| p123/58-10 | 1.1 | 1 | *B. thuringiensis* var. kurstaki HD-73, pBR322 |
| p403 | 2.2 | 2 | pBR322, pTi15955 |
| "1.6" | 2.2 | 2 | (= transcript 24, see also Detailed Description) |
| 177.4 | 4.1 | | Charon 24A, *P. vulgaris* cv. Tendergreen |
| pBt73-161 | 11.1 | | *B. thuringiensis* var. kurstaki HD-73, pBR322 |
| pBt73-10(Bam) | 11.2 | | p123/58-10 |
| pBt73-16 | 11.2 | 4 | pBt73-10(Bam), pBt73-161 |
| pTR-proI | 12.1 | 4 | = pKS-proI |
| pTR-proI(Bam) | 12.1 | 4 | pTR-proI |
| pBR325 | 12.3 | 4 | |
| pBR325aBB | 12.3 | 4 | pBR325 |
| p403B | 12.1 | 4 | pBR325aBB, pTR-proI(Bam) |

TABLE 4-continued

Index of plasmid and strains

| Strain or Plasmid | Constructed or used in Example | See FIG. | Made From (α comments) |
|---|---|---|---|
| M13mp19 | 12.4 | 4 | |
| 1.6.4 | 12.4 | 4 | M13mp19, pBt73-16 |
| 1.6.4B-3.8.3 | 12.4 | 4 | 1.6.4 |
| p403B/BTBΔ3 | 12.3 | 4 | 1.6.4B-3.8.3, p403B |
| pH4-1 | 12.1 | | pSUP106, pTi15955, GaMV, Tn5 |
| pH400 | 12.1 | | pH4-1 |
| pDOB412 | 12.2 | | CaMV, pBR322 |
| pDOB512 | 12.2 | | pDOB412 |
| p403BRL1 | 12.3 | | p403B |
| pDOB514 | 12.3 | | pDOB513 |
| pMAN514 | 12.3 | | p403BRL1, pDOB514 |
| pKS4.2 | 12.3 | | pKS4 |
| pKS4.3 | 12.3 | | pKS4.2 |
| pBR322Bam | 12.3 | | pBR322, lambda |
| p11-83c | 12.3 | | pKS4.3, pBR322Bam⁻ |
| pCJ161 | 12.5 | | 1.6.4B-3.8.3, pCG116 |
| pH450 | 12.6 | | pCJ161, pH400 |
| pCG116 | 12.3 | | p11-83c, pTR-proI(Bam) |

TABLE 5

Deposited strains

| | |
|---|---|
| NRRL B-4488 | *B. thuringiensis* var. *kurstaki* HD-73 |
| NRRL B-15394 | *E. coli* C600 (pKS-4) |
| NRRL B-11371 | *E. coli* HB101 |
| NRRL B-12014 | *E. coli* RR1 (pBR322) |
| ATCC 37017 | pBR322 |
| ATCC 15955 | *A. tumefaciens* (pTi15955) |
| NRRL B-15393 | *E. coli* HB101 (p8.8) |
| NRRL B-15612 | *E. coli* HB101 (p123/58-10) |
| NRRL B-15759 | *E. coli* HB101 (pBt73-16) |
| NRRL B-18009 | *E. coli* K802 (pH4-1) |
| NRRL B-15486 | *E. coli* CSH52 (pSUP106) |

TABLE 6

MS Medium

| | | |
|---|---|---|
| $NH_4NO_3$ | 1.65 | g/l |
| $KNO_3$ | 1.9 | g/l |
| $CaCl_2 \cdot 2H_2O$ | 440 | mg/l |
| $MgSO_4 \cdot 7H_2O$ | 370 | mg/l |
| $KH_2PO_4$ | 170 | mg/l |
| KI | 0.83 | mg/l |
| $H_3BO_3$ | 6.2 | mg/l |
| $MnSO_4 \cdot 4H_2O$ | 22.3 | mg/l |
| $ZnSO_4 \cdot 7H_2O$ | 8.6 | mg/l |
| $Na_2MoO_4 \cdot 2H_2O$ | 0.25 | mg/l |
| $CuSO_4 \cdot 5H_2O$ | 0.025 | mg/l |
| $CoCl_2 \cdot 6H_2O$ | 0.025 | mg/l |
| $Na_2 \cdot EDTA$ | 37.23 | mg/l |
| $FeSO_4 \cdot 7H_2O$ | 27.85 | mg/l |
| Inositol | 1 | g/l |
| Nicotinic acid | 50 | mg/l |
| Pyroxidine•HCl | 50 | mg/l |
| Thiamine•HCl | 50 | mg/l |
| Sucrose | 30 | g/l |
| Agar | 8 | g/l |

TABLE 7

| | Experiment 1[5] | | Experiment 2[6] | |
|---|---|---|---|---|
| Clone | $A_{492}$[1] | CP[2] | $A_{492}$ | CP |
| 100 | 0.17 ± 0.03[7] | + | 0.14 | + |
| 101 | 0.02 ± 0.01 | − | 0.07 | ± |
| 102 | 0.06 ± 0.02 | + | 0.21 | + |
| 103 | 0.00 ± 0.00 | − | ND | ND |
| 104 | ND[3] | ND | 0.11 | + |
| 105 | 0.00 ± 0.00 | − | 0.10 | + |
| 106 | 0.10 ± 0.02 | + | 0.01 | − |
| 107 | 0.06 ± 0.03 | ± | 0.06 | − |
| 109 | 0.11 ± 0.05 | + | 0.03 | − |
| 110 | 0.06 ± 0.01 | + | 0.13 | + |
| 111 | 0.12 ± 0.02 | + | 0.00 | − |
| NX[4] | 0 | | 0 | |

[1]Average of three ELISA determinations. Absorbance at 492 nm, corrected by subtracting the value for the NX control.
[2]Rated as having (+) or not having (−) crystal protein. ± indicates a marginal rating.
[3]Not determined.
[4]Untransformed *Nicodana tabacum* var. "Xanthi" control. In experiments 1 and 2, repectively, 18 and 19 control leaves obtained from different plants were averaged.
[5]Experiment 1 was standardized for equal tissue wet weight.
[6]Experiment 2 was standardized for equal plant protein concentrations.
[7]± standard error of the mean.

TABLE 8

| Clone number | Replicate number | Total larvae | Dead larvae |
|---|---|---|---|
| 100 | 1 | 4 | 1 |
| | 2 | 5 | 0 |
| | 3 | 5 | 4 |
| 103 | 1 | 5 | 0 |
| | 2 | 5 | 0 |
| | 3 | 5 | 0 |
| 106 | 1 | 5 | 0 |
| | 2 | 5 | 0 |
| | 3 | 5 | 0 |
| 109 | 1 | 5 | 2 |
| | 2 | 5 | 0 |
| | 3 | 5 | 3 |
| 111 | 1 | 5 | 2 |
| | 2 | 5 | 1 |
| | 3 | 5 | 0 |

TABLE 9

| Clone number | Replicate number | Total larvae | Dead larvae |
|---|---|---|---|
| 100 | 1 | 4 | 2 |
| | 2 | 4 | 3 |
| | 3 | 6 | 3 |
| 103 | 1 | 6 | 0 |
| | 2 | 6 | 2 |
| | 3 | 6 | 2 |
| 106 | 1 | 6 | 2 |
| | 2 | 8 | 3 |
| | 3 | 10 | 6 |
| 109 | 1 | 14 | 2 |
| | 2 | 6 | 1 |
| | 3 | 6 | 4 |
| 111 | 1 | 6 | 3 |
| | 2 | 6 | 2 |
| | 3 | 6 | 3 |

TABLE 10

| Callus #* | Treatment | ELISA Assays NPT2 | | Southern Blots IG | |
|---|---|---|---|---|---|
| | | NPT2 | Btt | Probe | Probe |
| 5-1 | Fusion-High | − | − | − | − |
| 5-2 | Fusion-High | + | + | + | + |
| 5-3 | Fusion-High | − | ND | ND | ND |
| 19-1 | Fusion-Low | − | + | ND | ND |
| 20-1 | Fusion-High | − | + | + | + |
| 20-2 | Fusion-High | − | − | + | + |
| 20-3 | Fusion-High | − | + | + | + |
| 34-1 | Fusion-Low | − | ND | + | + |
| 35-1 | Fusion-High | + | + | + | + |
| EG5 | Neg. Control | − | − | − | − |

ND = not determined

*Only 9 of the 10 kanamycin resistant "Fusion" calli produced sufficient callus tissue for these analyses.

TABLE 11

| Callus # | Exp. 1 | Exp. 2 |
|---|---|---|
| 6-1 | + | + |
| 6-3 | − | − |
| 6-4 | ND | − |
| 6-9 | + | ND |
| 6-11 | − | − |
| 6-12 | + | + |
| 6-18 | + | + |
| 6-19 | + | + |
| 6-21 | + | − |
| 6-23 | + | + |
| 6-32 | + | − |
| 21-3 | − | − |
| 21-4 | − | − |
| 21-5 | − | − |
| 21-8 | − | − |
| 21-9 | − | − |
| 21-12 | + | − |
| 21-13 | − | − |
| 21-16 | − | − |
| 21-19 | − | − |
| 21-26 | − | − |
| 36-1 | − | − |
| 36-3 | − | − |
| 36-4 | − | − |
| 36-12 | − | − |
| 36-14 | − | − |
| 36-17 | − | − |
| 36-25 | − | − |

ND = not determined

TABLE 12

Transformation of *Lycopersicum esculentum* hypocotyl and leaf disc tissues with various binary vectors

| Transforming Plasmid | Hypocotyl Tissue | | Leaf Tissue | |
|---|---|---|---|---|
| | Percent Transformed | Percent Transformed w/buds | Percent Transformed | Percent Transformed w/buds |
| pH450 | 19 (178)[a] | 9 (34) | 0.17 (1189) | 100 (2) |
| pH575 | 9 (180) | 28 (17) | 5 (640) | 0 |
| pH576 | 21 (123) | 19 (26) | 5 (1993) | 0 |
| pH577 | 11 (282) | 22 (32) | 1 (1430) | 42 (12) |
| pH578 | 9 (136) | 58 (12) | 4 (820) | 23 (31) |
| pH582 | 9 (97) | 0 | | |
| pH585 | 11.5 (104) | 25 (12) | | |

[a](number)

TABLE 13

Summary of bioassays and ELISAs on tomato

| Plant* | Gen | Plant age months | Percent mortality (n) | % worm weight | ELISA |
|---|---|---|---|---|---|
| UC82 | ($F_1$) | <6 | 13 (385) | 100 | − |
| UC82 | ($R_0$) | <6 | 17 (50) | 91 | − |
| V7R | ($F_1$) | <6 | 23 (30) | 118 | − |
| V7R | ($R_0$) | <6 | 19 (11) | 78 | − |
| pH450-7 | ($R_0$) | <6 | 73 (55) | 77 | + |
| | | >6 | 39 (36) | 86 | + |
| pH450-13 | ($R_0$) | <6 | 35 (20) | 29 | + |
| pH450-19 | ($R_0$) | <6 | 70 (20) | 32 | + |
| pH450-1-1a | ($R_1$) | <6 | 50 (38) | 20 | + |
| pH450-2-3a | ($R_1$) | <6 | 17 (18) | 91 | − |
| pH450-2-5a | ($R_1$) | <6 | 10 (10) | 55 | − |
| pH450-2-5b | ($R_1$) | <6 | 22 (9) | 38 | − |
| pH450-4-1c | ($R_1$) | <6 | 78 (9) | 69 | + |
| pH450-4-2e | ($R_1$) | <6 | 78 (18) | 40 | + |
| | | >6 | 46 (13) | 120 | + |
| pH450-4-2f | ($R_1$) | <6 | 50 (14) | 32 | + |
| pH577-3a | ($R_0$) | <6 | 74 (46) | 19 | + |
| pH577-3c | ($R_0$) | <6 | 80 (20) | 15 | + |
| pH577-3d | ($R_0$) | <6 | 40 (10) | 39 | NA |
| pH577-3g-1 | ($R_0$) | <6 | 85 (20) | 8 | + |
| pH577-3g-2 | ($R_0$) | <6 | 65 (30) | 19 | + |
| pH577-3g-4 | ($R_0$) | <6 | 19 (16) | 43 | NA |
| pH577-3g-7 | ($R_0$) | <6 | 60 (20) | 20 | NA |
| pH577-17-5 | ($R_0$) | <6 | 38 (32) | 61 | + |
| pH577-17-6 | ($R_0$) | <6 | 0 (10) | 80 | − |
| pH577-21b | ($R_0$) | <6 | 30 (10) | 60 | NA |
| pH578-6-1b | ($R_0$) | <6 | 65 (23) | 89 | + |
| pH578-6-2c | ($R_0$) | <6 | 0 (14) | 65 | − |
| pH578-15-10 | ($R_0$) | <6 | 67 (30) | 47 | + |

*All plants except UC82 and V7R are octopine positive and kanamycin resistant.

NA = not assayed.

TABLE 14

Media Composition Used for Cotton Regeneration[1]

| Medium | NAA (mg/l) | 2iP (mg/l) | IAA (mg/l) | kinetin (mg/l) | zeatin (mg/l) | MS salts | % (w/v) glucose (g) or sucrose (s) |
|---|---|---|---|---|---|---|---|
| ½G$_0$ | | | | | | ½X | 1.5 g |
| G$_0$ | | | | | | 1X | 3.0 g |
| G$_1$ | 5 | 1 | | | | 1X | 3.0 g |
| G$_2$ | 0.1 | 5 | | | | 1X | 3.0 g |
| G$_3$ | 5 | 0.1 | | | | 1X | 3.0 g |
| G$_4$ | | | 0.1 | 1 | | 1X | 3.0 g |
| G$_5$ | | | 2 | 1 | | 1X | 3.0 g |
| EF$_1$8 | 2 | | | 1 | | 1X | 3.0 g |
| MS$_{zn-g}$ | 0.1 | | | | 1 | 1X | 1.5 g |
| EG$_1$ | | | | 1 | | ½X | 1.5 s |
| EG$_3$ | 0.01 | | | | | ½X | 0.5 g |

[1]All media were prepared with MS salts (Gibco, Grand Island, NY), 100 mg/l myo-inositol, 0.4 mg/l thiamine HCl, 0.2% Gel-rite (Kelco, San Diego, CA), pH 5.9. The remaining media used have already been published or are mentioned in the text. All chemicals (unless indicated) were purchased from Sigma Co. (St. Louis, MO). IAA and zeatin were filter sterilized, and the rest were autoclaved.

TABLE 15

Effects of different media on cotton embryogenic callus frequency of Cokers 10 weeks and GSA's 8 months after explantation. A total of 30-40 calli per cultivar were tested.

| Initiation & induction media | Embryogenic calli formation medium | % Embryogenic calli[1] Coker | | | | (% Embryogenic mass)[2] GSA | | | |
|---|---|---|---|---|---|---|---|---|---|
| | | 201 | 208 | 310 | 315 | 25 | 71 | 75 | 78 |
| EF18 | EFs18 | 3(1) | 0 | 0 | 2(1) | 0 | — | — | 0 |
| G$_2$-G$_3$ | ½ G$_0$ | — | — | — | — | 0 | 3(1) | 2(1) | — |
| G$_2$-G$_3$ | G$_0$ | 85(75) | 49(38) | 61(52) | 80(68) | (4) | 10(4) | 12(4) | 20(15) |
| G$_2$-G$_1$ | G$_1$ | 50(41) | (17) | (18) | (12) | (3) | 0 | — | — |
| G$_2$-G$_3$ | G$_3$ | 54(45) | (31) | (32) | (15) | (3) | (6) | (4) | — |
| G$_2$-G$_4$ | G$_4$ | (26) | (16) | (1) | (8) | — | — | — | — |
| G$_2$-G$_5$ | G$_5$ | (14) | — | (1) | (10) | — | — | — | — |

[1]Based on numbers of calli.

[2]% Embryogenic mass was estimatated as $\frac{\text{mass of embryogenic calli}}{\text{total mass of calli}} \times 100$

TABLE 16

Effects of different media on cotton somatic embryo[1] germination and plantlet formation. (Total number embryos are shown with percentage of embryos germinated and formed plantlets, respectively.)

| Medium | Coker 201 | Coker 310 | Coker 315 | Coker 4360 | GSA78 |
|---|---|---|---|---|---|
| GRM$_{gn}$ | 650 (75, 55) | 30 (80, 20) | 41 (46, 24) | 28 (36, 25) | 152 (72, 56) |
| EG$_1$ | 83 (30, 16) | 24 (67, 17) | 23 (52, 4) | 26 (38, 15) | — |
| EG$_3$ | 175 (48, 25) | 25 (68, 4) | 16 (50, 6) | 44 (41, 2) | — |
| GRM | 71 (51, 30) | — | — | — | — |
| EG$_2$ | 43 (47, 12) | — | — | — | — |

[1]Somatic embryos were selected randomly so they consisted of normal, abnormal, small and large embryos, and they were distributed randomly over different media.
[2]Embryo germination medium used by Shoemaker, R. C. et al., supra. containing MS salts, 1 mg/l kinetin and 1.5% sucrose.

TABLE 17

Effects of embryo formation and embryo germination media on Coker 201 embryo germination and plantlet development.[1]

| Induction medium | Embryo Formation Medium | % Normal Embryos | Embryo Germination Medium | Total Number Embryos Plated (% Germinated, % Formed Plantlets) |
|---|---|---|---|---|
| $G_1, G_3$ | $G_0$ | 44 | $G_0$ | 25 (24, 24) |
| | | | $G_1$ | 16 (44, 33) |
| | | | $EG_3$ | 25 (40, 32) |
| | | | $GRM_{gn}$ | 46 (63, 54) |
| $G_1$ | $G_1$ | 14 | $G_1$ | 23 (22, 13) |
| | | | $GRM_{gn}$ | 30 (27, 23) |
| $G_3$ | $G_3$ | 32 | $G_0$ | 26 (38, 19) |
| | | | $G_1$ | 16 (19, 17) |
| | | | $EG_3$ | 35 (31, 23) |
| | | | $GRM_{gn}$ | 35 (37, 37) |

[1] Calli were initiated from hypocotyl sections on $G_2$, after three weeks transferred to $G_1$ or $G_3$, and after another three weeks were transferred to embryo formation media.

TABLE 18

Transformation Frequencies of Cotton Cotyledon Segments.

| | | Transformation Frequencies (%) | | | |
|---|---|---|---|---|---|
| | | Growing callus in the presence of kanamycin at (μg/ml) | | | Octopine |
| Construct | Cultivar | 25 | 50 | 100 | Positive |
| pH575 | Coker 201 | 75 | 78 | 85 | 33 |
| | GSA 75 | 40 | 54 | 43 | 32 |
| LBA4404 | Coker 201 | 20 | 13 | 2 | 0 |
| | GSA 75 | 14 | 11 | 0 | 0 |

TABLE 19

| Sample | NPTII ng/ml | protein g/ml | ngNPT/mg protein % expression |
|---|---|---|---|
| 1 | 325.9 | 8926 | 36.6 |
| 2 | 209.7 | 11744 | 17.9 |
| 3 | 714.7 | 14336 | 49.9 |
| 4 | 238.2 | 14673 | 16.2 |
| 5 | 318.4 | 10470 | 30.4 |
| 6 | 349.4 | 9489 | 36.8 |
| 7 | 253.5 | 9151 | 27.6 |
| 8 | 144.1 | 14335 | 13.4 |
| 9 (neg. cntrl) | 0.0 | 10770 | 0.0 |

We claim:

1. A regenerated cotton plant selected from the group consisting of (1) a plant of a Class 2 *Gossypium* genotype transformed to contain selected foreign DNA and having a phenotype conferred by said foreign DNA by which said cotton plant can be distinguished from naturally-occurring cotton plants, and (2) descendants of said cotton plant having said distinguishing phenotype; wherein said distinguishing phenotype is insect resistance conferred by expression of an insecticidal *Bacillus thuringiensis* crystal protein.

2. A transgenic cotton plant according to claim 1 comprising an insecticide structural gene under control of a plant-expressible promoter wherein said insecticide structural gene encodes the amino acid sequence of FIG. 1 and is expressed under control of said promoter such that tissues of said plant are toxic to insects.

\* \* \* \* \*

UNITED STATES PATENT AND TRADEMARK OFFICE
CERTIFICATE OF CORRECTION

| | | |
|---|---|---|
| PATENT NO. | : 7,345,229 B1 | |
| APPLICATION NO. | : 08/478153 | |
| DATED | : March 18, 2008 | |
| INVENTOR(S) | : Michael J. Adang, John D. Kemp and Ebrahim Firoozabady | |

It is certified that error appears in the above-identified patent and that said Letters Patent is hereby corrected as shown below:

Column 1,
Line 10, "Oct. 21, 1988" should read -- October 20, 1988 --.

Column 3,
Line 30, "Ruvidn" should read -- Ruvkin --.

Column 4,
Line 19, "market" should read -- marker --.

Column 8,
Line 39, "Aidyoshi" should read -- Akiyoshi --.

Column 9,
Line 32, "one" should read -- *onc* --.
Line 34, "one" should read -- *onc* --.

Column 10,
Line 10, "one genes), and nine (having one" should read -- *onc* genes), and nine (having *onc* --.
Line 28, "one" should read -- *onc* --.

Column 13,
Line 28, "one" should read -- *onc* --.

Column 39,
Line 22, "BgI11" should read -- *Bgl*II --.

Column 41,
Line 31, "Bgm" should read -- *Bgl*II --.
Lines 47-48, "SmaI-lineanzed, M13 mp19 RF DNA" should read -- *Sma*I-linearized, M13mp19 RF DNA --.

Column 42,
Line 54, "7.5 mg/1 &" should read -- 7.5 mg/16- --.
Line 65, "*B. thunngiensis*" should read -- *B. thuringiensis* --.

UNITED STATES PATENT AND TRADEMARK OFFICE
CERTIFICATE OF CORRECTION

PATENT NO. : 7,345,229 B1
APPLICATION NO. : 08/478153
DATED : March 18, 2008
INVENTOR(S) : Michael J. Adang, John D. Kemp and Ebrahim Firoozabady It is certified that error appears in the above-identified patent and that said Letters Patent is hereby corrected as shown below:

Column 44,
Line 57, "*Nicoliana tabacum*" should read -- *Nicotiana tabacum* --.

Column 47,
Line 38, "(SD Indicates the Location of a Shine-Dalgarno Prokaryotic Ribosome Binding Site.)" should read -- SD indicates the location of a Shine-Dalgarno prokaryotic ribosome binding site.) --.

Column 48,
Line 48, "Hind III" should read -- *Hind*III --.

Column 49,
Line 12, "pIC351A's" should read -- pIC35/A's --.

Column 51,
Line 3, "transcnbed" should read -- transcribed --.
Line 4, "CAMV" should read -- CaMV --.

Column 52,
Line 46, "$2.5 \times 10^6$ ml." should read -- $2.5 \times 10^6$ ml$^{-1}$. --.

Column 53,
Line 2, "thiamine. HC1" should read -- thiamine · HC1 --.
Line 30, "caili" should read -- calli --.

Column 54,
Line 22, "0.50 mg/l" should read -- 50 mg/l --.
Line 63, "*Agrobactetium*" should read -- *Agrobacterium* --.

Column 55,
Line 4, "6t1016" should read -- 6t0016 --.
Line 38, "0.1 mlavell" should read -- 0.1 ml/well --.

Column 56,
Line 21, "Was" should read -- was --.
Line 55, "*Manduca seta*" should read -- *Manduca sexta* --.

UNITED STATES PATENT AND TRADEMARK OFFICE
CERTIFICATE OF CORRECTION

PATENT NO.        : 7,345,229 B1
APPLICATION NO.   : 08/478153
DATED             : March 18, 2008
INVENTOR(S)       : Michael J. Adang, John D. Kemp and Ebrahim Firoozabady It is certified that error appears in the above-identified patent and that said Letters Patent is hereby corrected as shown below:

Column 57,
Line 62, "(UC82 Ro plants" should read -- (UC82 $R_0$ plants --.

Column 58,
Line 57, "25 mg/A" should read -- 25 mg/l --.

Column 59,
Line 5, "axiliary" should read -- axillary --.
Line 12, "carbenicllin" should read -- carbenicillin --.

Column 65,
Line 3, "GRMg" should read -- $GRM_{gn}$ --.

Column 68,
Line 2, "9 $\mu m^2/s$" should read -- 9 $\mu Em^2/s$ --.

Column 71,
Line 8, "G0" should read -- $G_0$ --.

Column 72,
Line 6, "Embryopenic" should read -- embryogenic --.
Line 34, "(G I or $G_3$)" should read -- ($G_1$ or $G_3$) --.

Column 73,
Line 14, "(9 $gE/m^2/s$)" should read -- (9 $\mu E/m^2/s$) --.

Column 76,
Line 55, "Polpomyla sp." should read -- Polpomyia sp. --.

Column 79,
Line 62, "Phyllonotycter" should read -- Phyllonorycter --.

Column 80,
Line 23, "Spionota" should read -- Spilonota --.
Line 36, "Thaumetopoea pilyocampa" should read -- Thaumetopoea pityocampa --.

UNITED STATES PATENT AND TRADEMARK OFFICE
CERTIFICATE OF CORRECTION

PATENT NO. : 7,345,229 B1
APPLICATION NO. : 08/478153
DATED : March 18, 2008
INVENTOR(S) : Michael J. Adang, John D. Kemp and Ebrahim Firoozabady It is certified that error appears in the above-identified patent and that said Letters Patent is hereby corrected as shown below:

Column 83,
Line 16, "GaMV, Tn5" should read -- CaMV, Tn5 --.

Column 84,
Table 7, Experiment $1^5$, Column $CP^2$, Row 102, "+" should read -- ± --.
Table 7, Experiment $1^5$, Column $CP^2$, Row 110, "+" should read -- ± --.

Column 87,
Table 14 foot note, lines 1-2, "myo-inosi-tol" should read -- myo-inositol --.

Signed and Sealed this

Sixteenth Day of December, 2008

JON W. DUDAS
*Director of the United States Patent and Trademark Office*